United States Patent [19]

Matsueda et al.

[11] Patent Number: 4,698,329

[45] Date of Patent: * Oct. 6, 1987

[54] NEW RENIN-INHIBITORY PEPTIDES AND THEIR USE

[75] Inventors: Rei Matsueda; Yuichiro Yabe; Mitsuo Yamazaki, all of Tokyo; Tatsuo Kokubu; Kunio Hiwada, both of Ehime, all of Japan

[73] Assignee: Sankyo Company, Limited, Tokyo, Japan

[*] Notice: The portion of the term of this patent subsequent to Oct. 22, 2002 has been disclaimed.

[21] Appl. No.: 696,334

[22] Filed: Jan. 30, 1985

[30] Foreign Application Priority Data

Feb. 3, 1984 [JP] Japan ................................. 59-19100

[51] Int. Cl.$^4$ ........................ A61K 37/64; C07K 5/08
[52] U.S. Cl. ..................................... 514/18; 530/331
[58] Field of Search .................... 260/112.5 R; 514/18; 530/331

[56] References Cited

U.S. PATENT DOCUMENTS 4,548,926 10/1985 Matsueda et al. ........... 260/112.5 R

OTHER PUBLICATIONS

Chem. Abstr. vol. 78, (1973) 119129z.
Chem. Abstr. vol. 92, (1980) 52413f.
Chem. Abstr. vol. 102, (1985) 46253n.
Chem. Abstr. vol. 103, (1985) 6692u.
Chem. Abstr. vol. 103, (1985) 50255c.
Chem. Abstr. vol. 103, (1985) 192067s.
Chem. Abstr. vol. 101, (1984) 192479m.
Chem. Abstr. vol. 101, (1984) 231034j.
Chem. Abstr. vol. 103, (1985) 142365s.
Rich et al., Synthesis of Analogues of the Carboxyl Protease Inhibitor Pepstatin$_1$. Effect of Structure on Inhibition of Pepsin and Renin, J. Med. Chem. (1980) 23, 27-33.
Aoyagi et al., Biological Activity of Pepstatins, Pepstanone A and Partial Peptides on Pepsin, Cathepsin D and Renin, J. of Antibiotics, vol. 25 (Dec., 1972) pp. 689-694.

Primary Examiner—Delbert R. Phillips
Attorney, Agent, or Firm—Frishauf, Holtz, Goodman & Woodward

[57] ABSTRACT

Compounds of formula

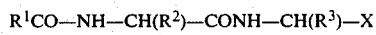

$R^1CO-NH-CH(R^2)-CONH-CH(R^3)-X$

[wherein:

$R^1$ represents alkyl having an α-amino or protected α-amino substituent and an aryl, heterocyclic or heterocyclic-dithio substituent;

$R^2$ represents a variety of aliphatic and cycloaliphatic hydrocarbon groups, which may be substituted;

$R^3$ represents isobutyl, sec-butyl, benzyl or ($C_3$–$C_8$ cycloalkyl)methyl; and X represents a group of formula —CH(—A—$R^4$)—Y (in which: A represents a single bond or an alkylene group; $R^4$ represents a carboxy group; a protected carboxy group, a carbamoyl group, an N-substituted carbamoyl group, a carbazoyl group, an N-substituted carbazoyl group or an acyl group; and Y represents a hydroxy group, a mercapto group or a formyl group), or a group of formula —P(O) ($R^5$)—OH (in which $R^5$ represents a substituted alkyl group having at least one substituent selected from carboxy groups, protected carboxy groups, N-substituted carbamoyl groups, carbazoyl groups, N-substituted carbazoyl groups, $C_2$–$C_7$ aliphatic carboxylic acyl groups and aromatic carboxylic acyl groups)];

and their salts are renin inhibitors, which may be used in the treatment of angiotensin-induced hypertension.

23 Claims, No Drawings

NEW RENIN-INHIBITORY PEPTIDES AND THEIR USE

BACKGROUND OF THE INVENTION

The present invention relates to a series of new hypotensive peptides which are of particular value in the treatment of hypertension induced by failures in the renin-angiotensin system, and to their use in such treatment.

There is considerable evidence that reduction of elevated blood pressure reduces the risks of morbidity and mortality. Elevated blood pressure (hypertension) can be caused by a variety of factors and a large number of drugs are available for the treatment of hypertension, the drug of choice being dictated in large measure by the cause of the hypertension. Angiotensin I is a polypeptide formed by the action of renin upon a plasma protein and is converted to angiotensin II by the action of ACE. Angiotensin II causes constriction of the arterioles and can produce hypertension. Hypertension of this type can be reduced by reducing the plasma concentration of angiotensin which, in turn, can be achieved by inhibiting the activity of renin. The number of available drugs having this type of inhibitory activity is very limited.

Certain peptide derivatives having this type of activity are disclosed in Japanese Patent Application Kokai No. 151166/77 and may be represented by the formula $R^aCO-X-His-NH-CH(CH_2R^b)-CHO$, in which $R^a$ and $R^b$ represent various organic groups and His represents the L-histidyl group.

Other polypeptides which have been proposed for use as renin inhibitors are the angiotensinogen fragments described by Szelke et al. [Nature, 299, 555 (1982)] and the statine derivatives described by Boger et al. [Nature, 303, 81 (1983)].

Certain hypotensive peptides closely related to the compounds of the present invention are disclosed in copending U.S. patent application Ser. No. 618,127, filed on 7th June 1984 by the present inventors, now U.S. Pat. No. 4,548,926.

We have now discovered a series of peptide derivatives having a very marked ability to inhibit the activity of renin.

BRIEF SUMMARY OF INVENTION

The compounds of the invention are peptides having the general formula (I):

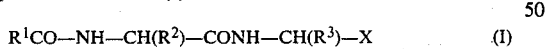

$$R^1CO-NH-CH(R^2)-CONH-CH(R^3)-X \quad (I)$$

[wherein:
$R^1$ represents a $C_1$–$C_4$ alkyl group having:
(a) an amino or protected amino substituent on its α-carbon atom and
(b) a carbocyclic aromatic substituent, a heterocyclic substituent or a heterocyclic-dithio substituent wherein the aromatic or heterocyclic ring is unsubstituted or has at least one substituent selected from the group consisting of amino groups, alkyl groups, hydroxy groups, alkoxy groups, halogen atoms, nitro groups, mercapto groups and alkylthio groups;
$R^2$ represents hydrogen, a $C_1$–$C_{18}$ alkyl group, a $C_2$–$C_5$ alkenyl group, a $C_2$–$C_5$ alkenyl group having at least one halogen substituent, a $C_2$–$C_5$ alkynyl group, a $C_3$–$C_7$ cycloalkyl group, a $C_5$–$C_8$ cycloalkenyl group, a $C_1$–$C_4$ alkyl group having one substituent selected from the group consisting of:
(c) $C_3$–$C_7$ cycloalkyl groups, $C_5$–$C_8$ cycloalkenyl groups, aryl groups and 5- and 6-membered heterocyclic groups having at least one hetero-atom selected from the group consisting of sulfur, nitrogen and oxygen atoms
or a $C_1$–$C_4$ alkyl group having one substituent selected from the group consisting of:
(c) $C_3$–$C_7$ cycloalkyl groups, $C_5$–$C_8$ cycloalkenyl groups, aryl groups and 5- and 6-membered heterocyclic groups having at least one hetero-atom selected from the group consisting of sulfur, nitrogen and oxygen atoms and
at least one substituent selected from the group consisting of:
(d) halogen atoms, hydroxy groups, alkoxy groups, aryloxy groups, aralkyloxy groups, aliphatic carboxylic acyloxy groups, mercapto groups, alkylthio groups, aliphatic carboxylic acylaminoalkylthio groups, arylthio groups, aralkylthio groups, alkylsulfinyl groups, alkylsulfonyl groups, arylsulfinyl groups, arylsulfonyl groups, amino groups, mono- and di-alkylamino groups, arylamino groups, aliphatic carboxylic acylamino groups, aromatic carboxylic acylamino groups, alkoxycarbonylamino groups, aralkyloxycarbonylamino groups, aliphatic carboxylic acyl groups, aromatic carboxylic acyl groups, carboxy groups, alkoxycarbonyl groups, aralkyloxycarbonyl groups, carbamoyl groups, mono- and di-alkylcarbamoyl groups, ureido groups, thioureido groups and guanidyl groups;
$R^3$ represents an isobutyl, sec-butyl, benzyl or ($C_3$–$C_8$ cycloalkyl)methyl group;
X represents a group of formula $-CH(-A-R^4)-Y$ (in which: A represents a single bond or an alkylene group; $R^4$ represents a carboxy group; a protected carboxy group, a carbamoyl group, an N-substituted carbamoyl group, a carbazoyl group, an N-substituted carbazoyl group or an acyl group; and Y represents a hydroxy group, a mercapto group or a formyl group), or
a group of formula $-P(O)(R^5)-OH$ (in which $R^5$ represents a substituted alkyl group having at least one substituent selected from carboxy groups, protected carboxy groups, N-substituted carbamoyl groups, carbazoyl groups, N-substituted carbazoyl groups, $C_2$–$C_7$ aliphatic carboxylic acyl groups and aromatic carboxylic acyl groups);

provided that, where A represents an alkylene group and
$R^2$ represents a 4-imidazolylmethyl group, $R^4$ does not represent a carbamoyl group or a formyl group];
and pharmaceutically acceptable salts thereof.

The invention also provides a method of treating angiotensin-induced hypertension in a mammal, which may be human or non-human, by administering to said mammal an effective amount of a renin inhibitor, wherein said renin inhibitor is selected from the group consisting of compounds of formula (I) and pharmaceutically acceptable salts thereof.

DETAILED DESCRIPTION OF INVENTION

In the compounds of the invention, where $R^1$ represents an alkyl group having an aryl substituent, the aryl substituent is preferably a phenyl or 1- or 2-naphthyl group and the alkyl group is a $C_1$–$C_4$ alkyl group, preferably a $C_1$ or $C_2$ alkyl group. Preferred such groups represented by $R^1$ are the α-aminobenzyl, α-aminophenethyl, 1-amino-3-phenylpropyl, 1-amino-2-(1-naphthyl)ethyl and 1-amino-2-(2-naphthyl)ethyl groups, in which the amino groups are free or protected, and in which the aryl groups may be substituted or unsubstituted, e.g. by hydroxy, $C_1$–$C_4$ alkyl, $C_1$–$C_4$ alkoxy, nitro, halo (e.g. chloro) or amino groups.

Where $R^1$ is an alkyl group (having from 1 to 4 and preferably 1 or 2 carbon atoms) having a heterocyclic substituent, the heterocyclic substituent preferably has from 4 to 8, more preferably 5, 6, 7 or 8, ring atoms, and has one or more hetero-atoms selected from the group consisting of nitrogen, oxygen and sulfur, preferably nitrogen. Particularly preferred heterocyclic groups are: the pyridyl groups, especially the 2-, 3- and 4-pyridyl groups; the quinolyl groups, especially the 3-, 4-, 5- and 8-quinolyl groups; the indolyl groups, especially the 2- and 3-indolyl groups; and the isoquinolyl groups. These heterocyclic groups may be unsubstituted or may have one or more substituents. Where they are substituted, preferred substituents are hydroxy groups, $C_1$–$C_4$ alkyl groups, halogen atoms, amino groups and nitro groups. Preferred substituted heterocyclic groups are the nitropyridyl groups.

Where $R^1$ is an alkyl group having a heterocyclic-dithio substituent, the heterocyclic group may be any one of those listed above, but is preferably a pyridyl group (2-, 3- or 4-pyridyl) optionally having one of the substituents mentioned above, preferably a nitro substituent.

The $C_1$–$C_4$ alkyl group represented by $R^1$ has, in addition to the aromatic or heterocyclic substituent, also a substituent (a) which is an amino group or a protected amino group. The amino group or protected amino group is on the α-carbon atom of the alkanoyl group represented by $R^1CO$—. The nature of the protecting group is not critical to the present invention and any protecting group commonly used in this field may be employed. Non-limiting examples of such protecting groups include the following:

alkoxycarbonyl groups, preferably ($C_1$–$C_6$ alkoxy)-carbonyl groups and more preferably ($C_3$–$C_5$ alkoxy)-carbonyl groups, most preferably ($C_4$ or $C_5$ alkoxy)carbonyl groups, for example the methoxycarbonyl, ethoxycarbonyl, propoxycarbonyl, isopropoxycarbonyl, butoxycarbonyl, sec-butoxycarbonyl, isobutoxycarbonyl or t-butoxycarbonyl or t-amyloxycarbonyl groups, of which the t-butoxycarbonyl or t-amyloxycarbonyl groups are the most preferred;

substituted alkoxycarbonyl groups, especially alkoxy-substituted groups (in which the alkoxy group itself may be substituted, preferably by another alkoxy group); the preferred groups are substituted ethoxycarbonyl groups, more preferably optionally substituted ethoxyethoxycarbonyl groups, and most preferably the 2-(2-methoxyethoxy)ethoxycarbonyl group;

alkanoyl groups, which may be straight or branched chain groups, and which preferably have from 2 to 7 carbon atoms (which number includes the carbon atom of the carbonyl group), more preferably 3 or 4 carbon atoms, for example the acetyl, propionyl, butyryl, isobutyryl, valeryl, isovaleryl, pivaloyl, hexanoyl or heptanoyl groups, more preferably the propionyl or butyryl groups;

alkoxycarbonyl or alkanoyl groups, such as those listed above, having an aryl or heterocyclic substituent, which itself may be substituted; aryl substituents are carbocyclic aryl groups, preferably having from 6 to 14 carbon atoms, and more preferably having 6, 10 or 13 carbon atoms, for example the phenyl, naphthyl (1- or 2-naphthyl) or fluorenyl (preferably 9-fluorenyl) groups; preferred heterocyclic substituents include the pyridyl groups, preferably the 2- and 3-pyridyl groups; examples of substituents on the aryl and heterocyclic groups are given hereafter; preferred examples of such substituted alkoxycarbonyl and alkanoyl groups include the benzyloxycarbonyl, 3-phenylpropionyl, 4-phenylbutyryl, 3-(1-naphthyl)propionyl and 3-pyrid-2-ylpropionyl groups;

alkanoyl or alkoxycarbonyl groups (which may be as exemplified above) having an aryldithio or heterocyclic-dithio substituent; examples of aryl and heterocyclic groups, which may be substituted, are given above; the preferred groups are the pyridyldithiopropionyl, phenyldithiopropionyl and 3-(3-nitropyrid-2-yldithio)-propionyl groups;

arylthio and heterocyclic-thio groups, in which the aryl and heterocyclic groups, which may be substituted, are preferably as exemplified above; preferred groups are the phenylthio, pyridylthio (especially 2-pyridylthio and 3-pyridylthio), 2-nitrophenylthio and 3-nitropyrid-2-ylthio groups; and amino acid residues, in which the amino group is protected by any one of the protecting groups referred to herein, particularly those referred to above, for example the alanyl, β-alanyl, glycyl, histidyl, homoseryl, isoleucyl, leucyl, lysyl, methionyl, norleucyl, norvalyl, ornithyl, sarcosyl, thyronyl, tyrosyl, valyl and tryptophyl groups, and such groups having aryl (as exemplified above) substituents, such as the phenylalanyl, chlorophenylalanyl, especially p-chlorophenylalanyl, and 3-naphthylalanyl, especially 3-(1-naphthyl)alanyl, groups; these groups may be L, DL or D and the preferred groups are the phenylalanyl, tryptophyl and 3-(1-naphthyl)alanyl groups, particularly the L-isomers.

Particularly preferred examples of acyl groups which may be represented by $R^1CO$— are the phenylalanyl, N-(benzyloxycarbonyl)phenylalanyl, N-(benzyloxycarbonyl)-(p-nitrophenyl)alanyl, N-(benzyloxycarbonyl)-(p-chlorophenyl)alanyl, 3-(1-naphthyl)alanyl, N-(benzyloxycarbonyl)phenylglycyl, N-(4-phenylbutyryl)-phenylalanyl, N-benzyloxycarbonyl-3-(3-quinolyl)alanyl, N-benzyloxycarbonyl-3-(4-quinolyl)alanyl, N-(benzyloxycarbonyl)tyrosyl, N-(2-nitrophenylthio)-phenylalanyl, N-(3-nitropyrid-2-ylthio)phenylalanyl, N-benzyloxycarbonyl-3-(1-naphthyl)alanyl, N-benzyloxycarbonyl-3-(2-naphthyl)alanyl, N-benzyloxycarbonyl-3-(5-quinolyl)alanyl, N-benzyloxycarbonyl-3-(8-quinolyl)alanyl, N-(t-butoxycarbonyl)-S-(3-nitropyrid-2-ylthio)cysteinyl, N-(9-fluorenylmethoxycarbonyl)-phenylalanyl, N-[N-(benzyloxycarbonyl)phenylalanyl]-phenylalanyl, N-[N-(benzyloxycarbonyl)-3-(1-naphthyl)alanyl]-3-(1-naphthyl)alanyl, N-(benzyloxycarbonyl)tryptophyl and N-(benzyloxycarbonyl)-3-(3-pyridyl)alanyl groups.

The alanyl, glycyl, tyrosyl, cysteinyl and tryptophyl groups referred to above may be D, DL or L (and, where there are 2 or more of them, they may be the same or different), but they are preferably L.

Where $R^2$ represents an unsubstituted alkyl group, this may be a straight or branched chain alkyl group and has from 1 to 18 carbon atoms, more preferably from 1 to 10 carbon atoms. Examples of such groups include the methyl, ethyl, propyl, isopropyl, butyl, isobutyl, sec-butyl, t-butyl, pentyl, isopentyl, neopentyl, t-pentyl, hexyl, isohexyl, 2-methylbutyl, 2-methylpentyl, heptyl, octyl, 2-ethylhexyl, nonyl, decyl, undecyl, dodecyl, tridecyl, tetradecyl, pentadecyl, hexadecyl, heptadecyl and octadecyl groups. Of these, the methyl, ethyl, propyl, isopropyl, butyl, isobutyl, sec-butyl, pentyl, heptyl and decyl groups are preferred.

Where $R^2$ represents an unsubstituted alkenyl group, this has from 2 to 5 carbon atoms and may be a straight or branched chain group. Examples of such groups include the vinyl, allyl, 1-propenyl, isopropenyl, 1-butenyl, 2-butenyl, 3-butenyl, 1-pentenyl, 2-pentenyl, 3-pentenyl and 4-pentenyl groups, of which the vinyl and allyl, especially the allyl, groups are preferred. Where $R^2$ represents a halogen-substituted alkenyl group, the halogen substituent may be a chlorine, fluorine, bromine or iodine atom, preferably a chlorine atom, and the alkenyl group may bear one or more, preferably from 1 to 3, such substituents.

Where $R^2$ represents a $C_2$–$C_5$ alkynyl group, this may be a straight or branched chain group and examples include the ethynyl, 1-propynyl, propargyl (i.e. 2-propynyl), 1-butynyl, 2-butynyl, 3-butynyl, 1-pentynyl, 2-pentynyl, 3-pentynyl and 4-pentynyl groups, of which the propargyl group is preferred.

Where $R^2$ represents a $C_3$–$C_7$ cycloalkyl group or a $C_1$–$C_4$ alkyl group having a $C_3$–$C_7$ cycloalkyl substituent, the alkyl group may be any one of the $C_1$–$C_4$ alkyl groups listed in relation to $R^2$ itself and the cycloalkyl groups may be a cyclopropyl, cyclobutyl, cyclopentyl, cyclohexyl or cycloheptyl group. The cycloalkyl group represented by $R^2$ is preferably a cyclopropyl, cyclopentyl or cyclohexyl group and the cycloalkyl-alkyl groups are preferably the cyclopropylmethyl, cyclopentylmethyl and cyclohexylmethyl groups.

Where $R^2$ represents a $C_5$–$C_8$ cycloalkenyl group or an alkyl group having a $C_5$–$C_8$ cycloalkenyl substituent, the cycloalkenyl group is preferably a cyclopentenyl (1-, 2- or 3-cyclopentenyl), a cyclohexenyl (1-, 2- or 3-cyclohexenyl) group or a cycloheptenyl (1-, 2-, 3- or 4-cycloheptenyl) group. In the case of the cycloalkenyl-alkyl groups, the alkyl group is preferably a methyl group.

Where $R^2$ represents an aralkyl group, the alkyl group has from 1 to 4 carbon atoms and may be a straight or branched chain group, for example the methyl, ethyl, propyl, isopropyl, butyl, isobutyl, sec-butyl or t-butyl group, preferably a methyl or ethyl group. The aryl group is an aromatic carbocyclic group, which may have 1, 2 or 3 fused rings. The preferred aryl groups are the phenyl and naphthyl (1- or 2-naphthyl) groups and the preferred aralkyl groups are the benzyl, phenethyl, 1-naphthylmethyl and 2-naphthylmethyl groups; the aryl portions of these aralkyl groups may be substituted or unsubstituted, and, if substituted, the substituents may be chosen from those listed hereafter in relation to aryl groups.

Where $R^2$ represents an alkyl group having a heterocyclic substituent, the heterocyclic ring contains 5 or 6 ring atoms, of which at least 1 (and preferably from 1 to 4) are hetero-atoms selected from the group consisting of sulfur, nitrogen and oxygen atoms. Examples of such heterocyclic groups are the indolyl (preferably 2- or 3-indolyl), thienyl (preferably 2-thienyl), thiazolyl (preferably 2- or 4-thiazolyl), pyridyl (2-, 3- or 4-pyridyl), pyrrolidinyl (preferably 2-pyrrolidinyl), thiazolidinyl (preferably 1,3-thiazolidin-4-yl), imidazolyl (preferably 4-imidazolyl), furyl (e.g. 2-furyl), quinolyl (e.g. 3-, 4-, 5- or 8-quinolyl) or piperidyl (e.g. 2-piperidyl) groups; the heterocyclic rings may be substituted or unsubstituted, and, if substituted, the substituents may be chosen from those listed hereafter.

The heterocyclic and aryl groups which may be substituents on the alkyl groups represented by $R^2$ may be themselves substituted and, if substituted, the substituents may be as described hereafter, but are preferably $C_1$–$C_4$ alkyl (particularly methyl) groups.

In addition to the aryl and heterocyclic groups mentioned above, $R^2$ may also have one or more other substituents on its alkyl group. Where the other substituent is a halogen atom, this is preferably a chlorine, bromine, fluorine or iodine atom and there may be one or more of these atoms as substituents. In particular, the alkyl group may, if desired, have three of these halogen substituents on a single carbon atom, for example three fluorine or chlorine substituents.

Where the alkyl group has an alkoxy substituent, this is preferably a $C_1$–$C_4$ alkoxy substituent, for example a methoxy, ethoxy, propoxy, isopropoxy, butoxy, isobutoxy, sec-butoxy or t-butoxy group.

Where the alkyl group represented by $R^2$ has an aryloxy group as the substituent, this is a carbocyclic aryloxy group and preferably has 1 or 2 carbocyclic rings, more preferably a phenoxy group. The aryloxy group may, if desired, be substituted by any one or more of the substituents hereafter described in relation to aryl groups.

Where the substituent on $R^2$ is an alkylthio group, this is preferably a $C_1$–$C_4$ alkylthio group, for example a methylthio, ethylthio, propylthio, isopropylthio, butylthio, isobutylthio, sec-butylthio or t-butylthio group.

Where the substituent on $R^2$ is an aliphatic carboxylic acylaminoalkylthio group, the aliphatic acyl group thereof may be any one of the $C_1$–$C_7$ alkanoyl groups hereafter described in relation to $R^4$.

Where the substituent on $R^2$ is an arylthio group, the aryl group is a carbocyclic aromatic group, preferably having 1 or 2 carbocyclic rings, preferably a phenyl group; this may be unsubstituted or it may be substituted as described hereafter in relation to aryl groups.

Where the substituent on $R^2$ is an aralkylthio group, the aralkyl group is preferably one of those described above in relation to $R^2$ itself, but is more preferably a benzylthio, phenethylthio or naphthylmethylthio group and the aryl group may be substituted or unsubstituted; if substituted, the substituents may be any of those described hereafter in relation to aryl groups.

Where the substituent on $R^2$ is an alkylsulfinyl group, this is preferably a $C_1$–$C_4$ alkylsulfinyl group, for example a methylsulfinyl, ethylsulfinyl, propylsulfinyl, isopropylsulfinyl, butylsulfinyl, isobutylsulfinyl, sec-butylsulfinyl or t-butylsulfinyl group.

Where the substituent on $R^2$ is an arylsulfinyl group, the aryl group is a carbocyclic aromatic group preferably having 1 or 2 carbocyclic rings and being optionally substituted as described hereafter in relation to aryl groups. Examples of such arylsulfinyl groups are the benzenesulfinyl, naphthalenesulfinyl and p-toluenesulfinyl groups.

Where the substituent on $R^2$ is an alkylsulfonyl group, this is preferably a $C_1$–$C_4$ alkylsulfonyl group, for example a methylsulfonyl, ethylsulfonyl, propylsulfonyl, isopropylsulfonyl, butylsulfonyl, isobutylsulfonyl, sec-butylsulfonyl or t-butylsulfonyl group.

Where the substituent on $R^2$ is an arylsulfonyl group, the aryl group is a carbocyclic aromatic group, preferably having 1 or 2 carbocyclic rings and being substituted or unsubstituted; if substituted, the substituents may be as described hereafter in relation to aryl groups. Preferred examples of such arylsulfonyl groups are the benzenesulfonyl, naphthalenesulfonyl and p-toluenesulfonyl groups.

Where the substituent on $R^2$ is a mono- or di-alkylamino group, the or each alkyl group is preferably a $C_1$–$C_4$ alkyl group, which may be a straight or branched chain group. Preferred examples of such alkylamino groups include the methylamino, dimethylamino, ethylamino, diethylamino, methylethylamino, propylamino, dipropylamino, methylpropylamino, isopropylamino, butylamino, dibutylamino, methylbutylamino, isobutylamino, sec-butylamino and t-butylamino groups.

Where the substituent on $R^2$ is an aliphatic carboxylic acylamino group, this is preferably a $C_1$–$C_7$ alkanoylamino group, for example a formamido, acetamido, propionamido, butyramido, isobutyramido, valeramido, isovaleramido, pivalamido or hexanamido group.

Where the substituent on $R^2$ is an alkoxycarbonylamino group, the alkoxy group may be a straight or branched chain group and preferably has from 1 to 4 carbon atoms. Examples of such groups include the methoxycarbonylamino, ethoxycarbonylamino, propoxycarbonylamino, isopropoxycarbonylamino, butoxycarbonylamino, isobutoxycarbonylamino, sec-butoxycarbonylamino and t-butoxycarbonylamino groups, more preferably the t-butoxycarbonylamino group.

Where the substituent on $R^2$ is an aralkyloxycarbonylamino group, the aryl group thereof is a carbocyclic aromatic group, preferably having 1 or 2 carbocyclic rings, and which may be unsubstituted or substituted (as described hereafter in relation to aryl groups). The alkyl group thereof is preferably a $C_1$–$C_4$ alkyl group, more preferably a $C_1$–$C_3$ alkyl group, examples of which are given above in relation to $R^2$ itself; the preferred groups are the straight-chain groups, particularly the methyl, ethyl and propyl groups and examples of such aralkyloxycarbonylamino groups are the benzyloxycarbonylamino, phenethyloxycarbonylamino and 3-phenylpropoxycarbonylamino groups, preferably the benzyloxycarbonylamino group.

Where the substituent on $R^2$ is an aliphatic carboxylic acyl group, this is preferably a $C_1$–$C_7$ alkanoyl group, for example a formyl, acetyl, propionyl, butyryl, isobutyryl, valeryl, isovaleryl, pivaloyl, hexanoyl or heptanoyl group.

Where the substituent on $R^2$ is an aromatic acyl group, the aromatic ring is a carbocyclic aromatic ring, preferably having 1 or 2 such rings. The preferred aromatic acyl group is the benzoyl group, which may be unsubstituted or may have one or more substituents, as described hereafter in relation to aryl groups.

Where the substituent on $R^2$ is an alkoxycarbonyl group, the alkoxy group thereof is preferably a $C_1$–$C_4$ alkoxy group and examples of such alkoxycarbonyl groups are the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups.

Where the substituent on $R^2$ is an aryloxycarbonyl group, the aryl group is an aromatic carbocyclic group, which preferably has 1 or 2 carbocyclic rings. It may be substituted or unsubstituted, as described hereafter in relation to aryl groups, and the preferred aryloxycarbonyl group is the phenoxycarbonyl group.

Where the substituent on $R^2$ is an aralkyloxycarbonyl group, the aryl group thereof is a carbocyclic aromatic group, which preferably has 1 or 2 carbocyclic rings, preferably a phenyl group. The alkyl group thereof is preferably a $C_1$–$C_4$ alkyl group (examples of which are given in relation to $R^2$ itself), but is preferably a straight-chain group, particularly the methyl, ethyl or propyl group. Examples of such aralkyloxycarbonyl groups are the benzyloxycarbonyl and phenethyloxycarbonyl groups.

Where the substituent on $R^2$ is a mono- or di-alkylcarbamoyl group, the alkyl group thereof is preferably a $C_1$–$C_4$ alkyl group (examples of which are given in relation to $R^2$ itself) and examples of such carbamoyl groups are the methylcarbamoyl, ethylcarbamoyl, dimethylcarbamoyl, diethylcarbamoyl, methylethylcarbamoyl, propylcarbamoyl, dipropylcarbamoyl, methylpropylcarbamoyl, isopropylcarbamoyl, butylcarbamoyl, isobutylcarbamoyl, sec-butylcarbamoyl and t-butylcarbamoyl groups.

In the compounds of the invention, $R^3$ represents an isobutyl, sec-butyl, benzyl or ($C_3$–$C_8$ cycloalkyl)methyl group. Where $R^3$ represents a ($C_3$–$C_8$ cycloalkyl)methyl group, this may be a cyclopropylmethyl, cyclobutylmethyl, cyclopentylmethyl, cyclohexylmethyl, cycloheptylmethyl or cyclooctylmethyl group and is more preferably a cyclopropylmethyl, cyclopentylmethyl or cyclohexylmethyl group, most preferably a cyclopentylmethyl or cyclohexylmethyl group. However, $R^3$ is preferably an isobutyl or sec-butyl group, more preferably an isobutyl group.

Where X represents a group of formula —CH(—A—$R^4$)—Y, A may represent a single bond, i.e. X represents a group of formula —CH($R^4$A)—Y, or it may represent an alkylene group. Where A represents an alkylene group, this preferably has from 1 to 8 carbon atoms and examples include the methylene, ethylene, ethylidene, propylidene, isopropylidene, trimethylene, tetramethylene, pentamethylene, hexamethylene, heptamethylene and octamethylene groups. Of these, A is preferably a $C_1$–$C_3$ alkylene group, particularly the methylene or ethylene group.

$R^4$ preferably represents a group of formula —COOR$^6$ (i.e. carboxy or protected carboxy), —CONR$^7$R$^8$ (i.e. carbamoyl or protected carbamoyl), —CONHNR$^9$R$^{10}$ (i.e. carbazoyl or substituted carbazoyl) or —COR$^{11}$ (i.e. acyl).

Where $R^4$ represents a group of formula —COOR$^6$, $R^6$ represents: a hydrogen atom, a $C_1$–$C_6$, preferably $C_2$–$C_5$, alkyl group, for example an ethyl, propyl, isopropyl, butyl, isobutyl, sec-butyl or 2-methylbutyl group; a carbocyclic aryl group having from 1 to 3 carbocyclic rings, preferably a phenyl group, which may be substituted or unsubstituted, the substituents being as defined hereafter; an aralkyl group, of which the alkyl moiety has from 1 to 4 (preferably 1 or 2) carbon atoms and the aryl moiety has from 1 to 3 (preferably 1) carbocyclic rings, the aralkyl group being substituted or unsubstituted and the substituents being as defined hereafter; or an acyloxymethyl group, wherein the acyl group is a $C_1$–$C_5$ aliphatic carboxylic acyl group or a benzoyl group which may be substituted or unsubstituted, the substituents being as defined hereafter.

Where $R^4$ represents a group of formula —$CONR^7R^8$, $R^7$ and $R^8$ may be the same or different and each represents: hydrogen; a $C_1$–$C_{10}$, preferably $C_2$–$C_8$, alkyl group which may be unsubstituted or may have one or more halogen or hydroxy substituents, for example the methyl, ethyl, propyl, isopropyl, butyl, sec-butyl, 2-methylbutyl, 1-hydroxymethyl-2-methylbutyl or 2,4-dihydroxy-1-(isobutyl)butyl groups; an aralkyl group which is as defined for $R^6$; a diaryl-alkyl group, wherein the aryl and alkyl moieties are each as defined for the respective moieties of the aralkyl group represented by $R^6$; a heterocyclic-substituted methyl or ethyl group, wherein the heterocyclic group has 5 or 6 ring atoms, is saturated or unsaturated and has from 1 to 3 hetero-atoms selected from nitrogen, sulfur and oxygen atoms, preferably a pyridylethyl group; a heterocyclic group having 5 or 6 ring atoms and from 1 to 3 hetero-atoms selected from the group consisting of nitrogen, sulfur and oxygen atoms, and which may be saturated or unsaturated (preferably saturated) and substituted or unsubstituted, the substituents being as defined hereafter, a preferred such heterocyclic group is the piperidyl group; or $R^7$ and $R^8$, together with the nitrogen atom to which they are attached, may represent a nitrogen-containing heterocyclic group having 5 or 6 ring atoms and having, in addition to the said nitrogen atom, 0, 1 or 2 additional hetero-atoms selected from the group consisting of nitrogen, sulfur and oxygen atoms, and which may be saturated or unsaturated and substituted or unsubstituted (the substituents being as defined hereafter), preferred such heterocyclic groups are the piperazinyl and piperidyl groups. Except where $R^7$ and $R^8$ together represent said heterocyclic group, we prefer that $R^7$ should represent a hydrogen atom and $R^8$ should represent one of the groups defined above.

Where $R^4$ represents a group of formula —$CONHNR^9R^{10}$, $R^9$ and $R^{10}$ may be the same or different and each represents: hydrogen; a $C_1$–$C_6$, preferably $C_1$–$C_4$ alkyl group, preferably the methyl, ethyl, propyl, isopropyl, butyl, isobutyl, t-butyl or sec-butyl groups, more preferably the methyl or butyl groups; a $C_1$–$C_7$ alkanoyl group, preferably an acetyl or propionyl group; a $C_2$–$C_9$ alkanoyl group having at its ω position an aryl or arylcarbonyl group, wherein the aryl group has from 1 to 3 carbocyclic rings and is substituted or unsubstituted, the substituents being as defined hereafter, preferably a phenyl group.

Where $R^4$ represents a group of formula —$COR^{11}$, $R^{11}$ represents: hydrogen; a $C_1$–$C_6$, preferably $C_1$–$C_4$, alkyl group, preferably the methyl, ethyl, propyl, isopropyl, butyl, isobutyl, t-butyl or sec-butyl groups, more preferably the methyl or butyl groups; or an aryl group having from 1 to 3 carbocyclic rings and being substituted or unsubstituted, the substituents being as defined hereafter.

Preferred examples of such groups which may be represented by X include the 1-hydroxy-ω-carboxyalkyl, 1-hydroxy-ω-methoxycarbonylalkyl, 1-hydroxy-ω-ethoxycarbonylalkyl, 1-hydroxy-ω-butoxycarbonylalkyl, 1-hydroxy-ω-isobutoxycarbonylalkyl, 1-hydroxy-ω-sec-butoxycarbonylalkyl, 1-hydroxy-ω-(2-methylbutoxy)carbonylalkyl, 1-hydroxy-ω-phenoxycarbonylalkyl, 1-hydroxy-ω-benzyloxycarbonylalkyl, 1-hydroxy-ω-phenacyloxycarbonylalkyl, 1-hydroxy-ω-(4-bromobenzyloxycarbonyl)alkyl, 1-hydroxy-ω-carbamoylalkyl, 1-hydroxy-ω-(N-methylcarbamoyl)alkyl, 1-hydroxy-ω-(N-ethylcarbamoyl)alkyl, 1-hydroxy-ω-(N-butylcarbamoyl)alkyl, 1-hydroxy-ω-(N-benzylcarbamoyl)alkyl, 1-hydroxy-ω-(N-sec-butylcarbamoyl)alkyl, 1-hydroxy-ω-[N-(2-methylbutyl)carbamoyl]alkyl, 1-hydroxy-ω-[N-(1-hydroxymethyl-2-methylbutyl)carbamoyl]alkyl, 1-hydroxy-ω-[N-(4-methoxybenzyl)carbamoyl]alkyl, 1-hydroxy-ω-[N-(4-chlorobenzyl)carbamoyl]alkyl, 1-hydroxy-ω-[N-(2-phenylethyl)carbamoyl]alkyl, 1-hydroxy-ω-[N-(2-phenylpropyl)carbamoyl]alkyl, 1-hydroxy-ω-[N-(1,2-diphenylethyl)carbamoyl]alkyl, 1-hydroxy-ω-[N-(2-pyrid-2-ylethyl)carbamoyl]alkyl, 1-hydroxy-ω-[N-(2-pyrid-4-ylethyl)carbamoyl]alkyl, 1-hydroxy-ω-[N-(1-benzylpiperid-4-yl)carbamoyl]alkyl, 1-hydroxy-ω-[N-(2-morpholinoethyl)carbamoyl]alkyl, 1-hydroxy-ω-{N-[1-(4-methoxybenzyl)]-4-piperidyl]carbamoyl}alkyl, 1-hydroxy-ω-(4-phenyl-1-piperazinylcarbonyl)alkyl, 1-hydroxy-ω-(4-benzyl-1-piperazinylcarbonyl)alkyl, 1-hydroxy-ω-[4-(m-tolyl)-1-piperazinylcarbonyl]alkyl, 1-hydroxy-ω-(4-phenyl-piperidinocarbonyl)alkyl, 1-hydroxy-ω-carbazolylalkyl, 1-hydroxy-ω-($N^2$-methylcarbazoyl)alkyl, 1-hydroxy-ω-($N^2$-butylcarbazoyl)alkyl, 1-hydroxy-ω-($N^2$-propionylcarbazoyl)alkyl, 1-hydroxy-ω-[$N^2$-(ω-phenylalkylcarbonyl)carbazoyl]alkyl, 1-hydroxy-ω-[$N^2$-(ω-benzoylalkylcarbonyl)carbazoyl]alkyl, 1-hydroxy-ω-propionylalkyl, 1-hydroxy-ω-benzoylalkyl, 1-mercapto-ω-ethoxycarbonylalkyl, 1-mercapto-ω-[N-(2-methylbutyl)carbamoyl]alkyl, 1-mercapto-ω-[N-(1-hydroxy-2-methylbutyl)carbamoyl]alkyl, 1-mercapto-ω-(N-ethylcarbamoyl)alkyl, 1-mercapto-ω-(N-benzylcarbamoyl)alkyl, 1-formyl-ω-ethoxycarbonylalkyl, 1-formyl-ω-benzyloxycarbonylalkyl, 1-formyl-(N-butylcarbamoyl)alkyl, 1-formyl-ω-(N-benzylcarbamoyl)alkyl and 1-formyl-ω-propionylalkyl groups, of which the alkyl groups have from 1 to 9 carbon atoms and are preferably the methyl, ethyl, propyl, isopropyl, butyl, sec-butyl, iso-butyl, t-butyl, pentyl, isopentyl, hexyl, 2-methylbutyl, heptyl, octyl, 2-ethylhexyl or nonyl groups.

Where X represents a group of formula —$P(O)(R^5)$—OH, $R^5$ represents an alkyl group having a carboxy, protected carboxy, N-substituted carbamoyl, carbazoyl, N-substituted carbazoyl, $C_2$–$C_7$ aliphatic carboxylic acyl or aromatic acyl or aromatic carboxylic acyl group. Examples of such groups represented by $R^5$ are given in relation to the similar groups which may be represented by $R^4$. Examples of such groups which may be represented by X include the ω-carboxyalkylphosphinico, ω-methoxycarbonylalkylphosphinico, ω-ethoxycarbonylalkylphosphinico, ω-benzyloxycarbonylalkylphosphinico, ω-(N-butylcarbamoyl)alkylphosphinico, ω-[N-(2-methylbutyl)carbamoyl]alkylphosphinico, ω-[N-(1-hydroxy-2-methylbutyl)carbamoyl]alkylphosphinico, ω-[N-(1-benzyl-4-piperidyl)carbamoyl]alkylphosphinico, ω-($N^2$-butylcarbazoyl)alkylphosphinico, ω-[$N^2$-(ω-phenylalkylcarbonyl)carbazoyl]alkylphosphinico and ω-[$N^2$-(ω-benzoylalkylcarbonyl)carbazoyl]alkylphosphinico groups, in which the or each alkyl group has from 1 to 8 carbon atoms, and is preferably a methyl, ethyl, propyl, isopropyl, butyl, isobutyl, sec-butyl, t-butyl, pentyl, isopentyl, hexyl, 2-methylbutyl, heptyl, octyl or 2-ethylhexyl group.

Where references are made hereinabove to substituted aryl groups, the substituents are preferably selected from the group consisting of: $C_1$–$C_4$ alkyl groups, preferably methyl or ethyl groups; halogen atoms, preferably chlorine or bromine atoms; $C_1$–$C_4$ alkoxy groups, preferably methoxy or ethoxy groups; hydroxy groups; nitro groups; amino groups; mercapto groups; and $C_1$–$C_4$ alkylthio groups. Where references are made above to substituted heterocyclic groups, the substituents are preferably selected from the group consisting of: $C_1$–$C_4$ alkyl groups, e.g. as exemplifiedd above; phenyl groups, which may optionally be substituted as for the aryl groups referred to above; benzyl groups which may optionally be substituted as for the aryl groups above; and halogen atoms.

Preferred compounds of the invention are those in which:

$R^1$ represents a group of formula $R^{13}$—CH(NHR$^{12}$)—, in which $R^{12}$ represents hydrogen, or a 2-(2-methoxyethoxy)ethoxycarbonyl, benzyloxycarbonyl, p-methoxybenzyloxycarbonyl, t-butoxycarbonyl, 9-fluorenylmethoxycarbonyl, 2-nitrophenylthio, 3-nitropyrid-2-ylthio, 4-phenylbutyryl or 3-(3-nitropyrid-2-yldithio)propionyl group; and $R^{13}$ represents a benzyl, benzyl having a substituent selected from the group consisting of $C_1$–$C_4$ alkyl groups, amino groups, $C_1$–$C_4$ alkoxy groups, hydroxy groups, halogen atoms, nitro groups, mercapto groups and $C_1$–$C_4$ alkylthio groups, 1-naphthylmethyl, 2-naphthylmethyl, 3-indolylmethyl, 5-quinolylmethyl, 4-quinolylmethyl, 2-pyridylmethyl, 3-pyridylmethyl or 4-pyridylmethyl group;

$R^2$ represents a $C_1$–$C_{10}$ alkyl group, a $C_2$–$C_5$ alkenyl group, a $C_2$–$C_5$ alkenyl group having at least one halogen substituent, a $C_2$–$C_4$ alkynyl group, a $C_3$–$C_6$ cycloalkyl group, a ($C_3$–$C_6$ cycloalkyl)methyl group, a $C_5$–$C_8$ cycloalkenyl group, a ($C_5$–$C_8$ cycloalkenyl)methyl group, or a benzyl, 3-indolylmethyl, 2-thienylmethyl, 4-thiazolylmethyl, 2-thiazolylmethyl, 4-methyl-5-thiazolylmethyl, 2-pyridylmethyl, 3-pyridylmethyl, 4-pyridylmethyl, 4-imidazolylmethyl, 2-pyrrolidinylmethyl, 1-($C_1$–$C_4$ alkyl)-2-pyrrolidinylmethyl, 1,3-thiazolidin-4-ylmethyl or 3-($C_1$–$C_4$ alkyl)-1,3-thiazolidin-4-ylmethyl group, or any such group wherein any $C_1$–$C_4$ alkyl portion has at least one substituent selected from the group consisting of hydroxy groups, alkoxy groups, aralkyloxy groups, aliphatic carboxylic acyloxy groups, mercapto groups, alkylthio groups, alkylsulfinyl groups, alkylsulfonyl groups, amino groups, monoalkylamino groups, dialkylamino groups, aliphatic carboxylic acylamino groups, aromatic carboxylic acylamino groups, alkoxycarbonylamino groups, aralkyloxycarbonylamino groups, aliphatic carboxylic acyl groups, carboxy groups, alkoxycarbonyl groups, aryloxycarbonyl groups, aralkyloxycarbonyl groups, carbamoyl groups, ureido groups and guanidyl groups;

$R^4$ represents a protected carboxy group, a carbamoyl group, an N-substituted carbamoyl group, a carbazoyl group, an N-substituted carbazoyl group or an acyl group;

Y represents a hydroxy or mercapto group;

$R^5$ represents an alkyl group having a substituent selected from the group consisting of protected carboxy groups, N-substituted carbamoyl groups, carbazoyl groups, N-substituted carbazoyl groups, $C_2$–$C_7$ aliphatic carboxylic acyl groups and aromatic carboxylic acyl groups; and $R^3$ represents an isobutyl, sec-butyl, cyclopropylmethyl, cyclopentylmethyl or cyclohexylmethyl group.

A more preferred class of compounds of the invention are those in which:

$R^1$ represents a group of formula $R^{13}$—CH(NHR$^{12}$)— in which:

$R^{12}$ represents a 2-(2-methoxyethoxy)ethoxycarbonyl, benzyloxycarbonyl, p-methoxybenzyloxycarbonyl, t-butoxycarbonyl, 9-fluorenylmethoxycarbonyl, 4-phenylbutyryl or 3-(3-nitropyrid-2-yldithio)propionyl group; and $R^{13}$ represents a benzyl group, a benzyl group having at least one substituent selected from the group consisting of $C_1$–$C_4$ alkyl groups and $C_1$–$C_4$ alkoxy groups, a 1-naphthylmethyl group, a 3-indolylmethyl group, a 5-quinolylmethyl group, a 4-quinolylmethyl group, a 2-pyridylmethyl group, a 3-pyridylmethyl group or a 4-pyridylmethyl group;

$R^2$ represents a $C_1$–$C_{10}$ alkyl group, an allyl group, a propargyl group, a cyclopropylmethyl group, a cyclopentylmethyl group, a cyclohexylmethyl group, a benzyl group, a 3-indolylmethyl group, a 2-thienylmethyl group, a 4-thiazolylmethyl group, a 2-thiazolylmethyl group, a 4-methyl-5-thiazolylmethyl group, a 2-pyridylmethyl group or a 4-imidazolylmethyl group;

$R^4$ represents a protected carboxy group, a carbamoyl group, an N-substituted carbamoyl group, a carbazoyl group, an N-substituted carbazoyl group or an acyl group;

Y represents a hydroxy or mercapto group;

$R^5$ represents an alkyl group having a substituent selected from the group consisting of protected carboxy, N-substituted carbamoyl, carbazoyl, N-substituted carbazoyl, $C_2$–$C_7$ aliphatic carboxylic acyl and aromatic carboxylic acyl groups; and $R^3$ represents an isobutyl or sec-butyl group.

Specific examples of compounds of the invention are given in the following list; the numbers appended to the compounds in this list are, where appropriate, used hereafter to identify those compounds.

1. ethyl 4(S)-[N-(4-phenylbutyryl)-L-phenylalanyl-L-histidyl]amino-3(S)-hydroxy-6-methylheptanoate
2. p-bromophenacyl 4(S)-{N-[3-nitropyrid-2-yldithio)-propionyl]-L-phenylalanyl-L-histidyl]amino-3(S)-hydroxy-6-methylheptanoate
3. 4(S)-[N-benzyloxycarbonyl-3-(1-naphthyl)-L-alanyl-L-histidyl]amino-3(S)-hydroxy-6-methylheptanoic acid
4. 4(S)-[N-benzyloxycarbonyl-3-(1-naphthyl)-D-alanyl-L-histidyl]amino-3(S)-hydroxy-6-methylheptanoic acid
5. ethyl 4(S)-[N-benzyloxycarbonyl-3-(1-naphthyl)-L-alanyl-L-histidyl]amino-3(S)-hydroxy-6-methylheptanoate
6. sec-butyl 4(S)-[N-acetyl-D-alanyl-L-histidyl]amino-3(S)-hydroxy-6-methylheptanoate
7. isobutyl 5(S)-[N-benzyloxycarbonyl-3-(1-naphthyl)-D-alanyl-L-histidyl]amino-4(S)-hydroxy-7-methyloctanoate
8. ethyl 4(S)-[N-benzyloxycarbonyl-3-(2-naphthyl)-L-alanyl-L-histidyl]amino-3(S)-hydroxy-6-methylheptanoate
9. methyl 3(S)-[N-benzyloxycarbonyl-3-(3-pyridyl)-L-alanyl-L-histidyl]amino-2(S)-hydroxy-5-methylhexanoate
10. ethyl 4(S)-[N-benzoyl-3-(5-quinolyl)-L-alanyl-L-histidyl]amino-3(S)-hydroxy-6-methylheptanoate 11. 4(S)-[N-benzyloxycarbonyl-3-(1-naphthyl)-L-alanyl-L-histidyl]amino-3(S)-hydroxy-5-methylheptanoic acid
12. ethyl 4(S)-[N-benzyloxycarbonyl-3-(1-naphthyl)-L-alanyl-L-histidyl]amino-3(S)-hydroxy-5-methylheptanoate
13. ethyl 4(S)-[N-benzyloxycarbonyl-3-(1-naphthyl)-D-alanyl-L-histidyl]amino-3(S)-hydroxy-5-methylheptanoate
14. benzyl 3(S)-[N-benzyloxycarbonyl-3-(1-naphthyl)-L-alanyl-L-histidyl]amino-2(S)-hydroxy-5-methylhexanoate
15. benzyl 4(S)-[N-benzyloxycarbonyl-3-(1-naphthyl)-L-alanyl-L-histidyl]amino-3(S)-hydroxy-6-methylheptanoate
16. benzyl 4(S)-[N-benzyloxycarbonyl-3-(1-naphthyl)-D-alanyl-L-histidyl]amino-3(S)-hydroxy-6-methylheptanoate
17. benzyl 4(S)-[3-(1-naphthyl)-D-alanyl-L-histidyl]amino-3(S)-hydroxy-6-methylheptanoate
18. benzyl 5(S)-[t-butoxycarbonyl-3-(1-naphthyl)-L-alanyl-L-histidyl]amino-4(S)-hydroxy-7-methyloctanoate
19. benzyl 4(S)-[t-butoxycarbonyl-3-(1-naphthyl)-L-alanyl-L-histidyl]amino-3(S)-hydroxy-5-methylheptanoate
20. benzyl 4(S)-[N-benzyloxycarbonyl-3-(1-naphthyl)-D-alanyl-L-histidyl]amino-3(S)-hydroxy-5-methylheptanoate
21. phenyl 4(S)-[N-benzyloxycarbonyl-3-(1-naphthyl)-L-alanyl-L-histidyl]amino-3(S)-hydroxy-6-methylheptanoate
22. phenacyl 4(S)-[N-benzyloxycarbonyl-3-(1-naphthyl)-L-alanyl-L-histidyl]amino-3(S)-hydroxy-6-methylheptanoate
23. p-bromophenacyl 4(S)-[N-benzyloxycarbonyl-3-(1-naphthyl)-D-alanyl-L-histidyl]amino-3(S)-hydroxy-6-methylheptanoate
24. N-butyl-3(S)-[N-benzyloxycarbonyl-3-(1-naphthyl)-L-alanyl-L-histidyl]amino-2(S)-hydroxy-5-methylhexanamide
25. N-sec-butyl-3(S)-[N-benzyloxycarbonyl-3-(1-naphthyl)-L-alanyl-L-histidyl]amino-2(S)-hydroxy-5-methylhexanamide
26. N-benzyl-4(S)-[N-benzyloxycarbonyl-L-tyrosyl-L-histidyl]amino-3(S)-hydroxy-5-methylheptanamide
27. N-benzyl-3(S)-[N-benzyloxycarbonyl-3-(1-naphthyl)-L-alanyl-L-histidyl]amino-2(S)-hydroxy-5-methylhexanamide
28. N-benzyl-3(S)-[N-benzyloxycarbonyl-3-(1-naphthyl)-D-alanyl-L-histidyl]amino-2(S)-hydroxy-5-methylhexanamide
29. N-benzyl-3(S)-[N-benzyloxycarbonyl-3-(1-naphthyl)-L-alanyl-L-histidyl]amino-2(S)-hydroxy-4-methylhexanamide
30. 1-{3(S)-[N-benzoyl-3-(1-naphthyl)-L-alanyl-L-histidyl]amino-2(S)-hydroxy-5-methylhexanoyl}-4-(m-tolyl)piperazine
31. 1-benzyl-4-{4(S)-[N-benzyloxycarbonyl-3-(1-naphthyl)-L-alanyl-L-histidyl]amino-3(S)-hydroxy-6-methylheptanamido}piperidine
32. 1-benzyl-4-{4(S)-[N-benzyloxycarbonyl-L-tryptophyl-L-histidyl]amino-3(S)-hydroxy-6-methylheptanamido}piperidine
33. 4(S)-[N-acetyl-3-(1-naphthyl)-L-alanyl-L-histidyl]amino-3(S)-hydroxy-6-methyl-N-(2-pyridylmethyl)heptanamide
34. 4(S)-[N-benzyloxycarbonyl-3-(1-naphthyl)-D-alanyl-L-histidyl]amino-3(S)-hydroxy-6-methyl-N-(4-pyridylmethyl)heptanamide
35. N-{4(S)-[N-benzyloxycarbonyl-L-tyrosyl-L-histidyl]amino-3(S)-hydroxy-6-methylheptanoyl}-L-isoleucinol
36. 1-{4(S)-[N-benzyloxycarbonyl-3-(1-naphthyl)-L-alanyl-L-histidyl]amino-3(S)-hydroxy-6-methylheptanoyl}-4-phenylpiperidine
37. 1-{4(S)-[N-benzyloxycarbonyl-3-(1-naphthyl)-D-alanyl-L-histidyl]amino-3(S)-hydroxy-6-methylheptanoyl}-4-benzylpiperazine
38. 4(S)-[N-benzyloxycarbonyl-3-(1-naphthyl)-L-alanyl-L-histidyl]amino-3(S)-hydroxy-6-methylheptanoic acid hydrazide
39. $N^1$-{4(S)-[N-benzyloxycarbonyl-3-(1-naphthyl)-L-alanyl-L-histidyl]amino-3(S)-hydroxy-6-methylheptanoyl}-$N^2$-(4-phenylbutyryl)hydrazine
40. $N^1$-{4(S)-[N-benzyloxycarbonyl-3-(1-naphthyl)-L-alanyl-L-histidyl]amino-3(S)-hydroxy-6-methylheptanoyl}-$N^2$-(4-benzoylbutyryl)hydrazine
41. $N^1$-butyl-$N^2$-{4(S)-[N-benzyloxycarbonyl-3-(1-naphthyl)-D-alanyl-L-histidyl]amino-3(S)-hydroxy-6-methylheptanoyl}hydrazine
42. $N^1$-sec-butyl-$N^2$-}4(S)-[N-benzyloxycarbonyl-3-(1-naphthyl)-D-alanyl-L-histidyl]amino-3(S)-hydroxy-6-methylheptanoyl}hydrazine
43. 1-propionyl-3(S)-[N-benzyloxycarbonyl-3-(1-naphthyl)-L-alanyl-L-histidyl]amino-2(S)-hydroxy-5-methylhexane
44. 1-benzoyl-3(S)-[N-benzyloxycarbonyl-3-(1-naphthyl)-L-alanyl-L-histidyl]amino-2(S)-hydroxy-5-methylhexane
45. benzyl 4(S)-[N-benzyloxycarbonyl-3-(1-naphthyl)-L-alanyl-L-histidyl]amino-3(S)-mercapto-6-methylheptanoate
46. N-benzyl-4(S)-[N-benzyloxycarbonyl-3-(1-naphthyl)-L-alanyl-L-histidyl]amino-3(S)-mercapto-6-methylheptanamide
47. benzyl 4(S)-[N-benzyloxycarbonyl-3-(1-naphthyl)-L-alanyl-L-histidyl]amino-3(S)-formyl-6-methylheptanoate
48. N-benzyl-4(S)-[N-benzyloxycarbonyl-3-(1-naphthyl)-L-alanyl-L-histidyl]amino-3(S)-formyl-6-methylheptanamide
49. 1-propionyl-4(S)-[N-benzyloxycarbonyl-L-phenylalanyl-L-histidyl]amino-3-formyl-6-methylheptane
50. methyl{1(S)-[N-benzyloxycarbonyl-3-(1-naphthyl)-D-alanyl-L-histidyl]amino-3-methylbutylphosphinico}acetate
51. ethyl{1(S)-[N-benzyloxycarbonyl-3-(8-quinolyl)-D-alanyl-L-histidyl]amino-3-methylbutylphosphinico}acetate
52. ethyl 4(S)-[N-benzyloxycarbonyl-3-(5-quinolyl)-D-alanyl-L-histidyl]amino-6-methylheptanoate
53. benzyl[1(RS)-{N-[N-t-butoxycarbonyl-3-(3-nitropyrid-2-yldithio)-L-alanyl]-L-phenylalanyl-L-histidyl}amino-2-methylbutylphosphinico]acetate
54. benzyl{1(S)-[N-benzyloxycarbonyl-3-(1-naphthyl)-D-alanyl-L-histidyl]amino-3-methylbutylphosphinico}acetate
55. benzyl{1(S)-[3-(1-naphthyl)-D-alanyl-L-histidyl]amino-3-methylbutylphosphinico}acetate
56. benzyl{1(S)-[N-benzyloxycarbonyl-3-(1-naphthyl)-D-alanyl-L-histidyl]amino-2-methylbutylphosphinico}acetate 57. N-benzyl-2-[1(RS)-{N-[3-(3-nitropyrid-2-yldithio)-propionyl]-L-phenylalanyl-L-histidyl}amino-2-methylbutylphosphinico]acetamide
58. N-benzyl-2-{1(RS)-[N-benzyloxycarbonyl-3-(1-naphthyl)-D-alanyl-L-histidyl]amino-3-methylbutylphosphinico}acetamide
59. N-benzyl-2-{1(RS)-[N-benzyloxycarbonyl-3-(1-naphthyl)-D-alanyl-L-histidyl]amino-2-methylbutylphosphinico}acetamide
60. 4-[3-{1(RS)-[N-benzyloxycarbonyl-3-(1-naphthyl)-L-alanyl-L-histidyl]amino-3-methylbutylphosphinico}propionamido]-1-benzylpiperidine
61. methyl[1-{[N-benzyloxycarbonyl-3-(1-naphthyl)-L-alanyl-L-histidyl]amino}-3-methylbutylphosphinico]acetate
62. methyl 3(S)-[N-benzyloxycarbonyl-3-(1-naphthyl)-L-alanyl-L-histidyl]amino-2(S)-hydroxy-5-methylhexanoate
63. 1-{4(S)-[N-benzyloxycarbonyl-3-(1-naphthyl)-L-alanyl-L-histidyl]amino-3(S)-hydroxy-6-methylheptanamido}-4-(3-trifluoromethylphenyl)piperazine
64. 4(S)-[N-benzyloxycarbonyl-3-(1-naphthyl)-L-alanyl-L-histidyl]amino-N-butyl-3(S)-hydroxy-6-methylheptanamide
65. 4(S)-[N-benzyloxycarbonyl-3-(1-naphthyl)-L-alanyl-L-histidyl]amino-3(S)-hydroxy-6-methyl-N-[S-(−)-2-methylbutyl]heptanamide
66. 4(S)-[N-benzyloxycarbonyl-3-(1-naphthyl)-L-alanyl-L-histidyl]amino-N-ethyl-3(S)-hydroxy-6-methylheptanamide
67. N-{4(S)-[N-benzyloxycarbonyl-3-(1-naphthyl)-L-alanyl-L-histidyl]amino-3(S)-hydroxy-6-methylheptanoyl}-L-isoleucinol
68. ethyl 4(S)-[N-(4-phenylbutyryl)-L-phenylalanyl-D-histidyl]amino-3(S)-hydroxy-6-methylheptanoate
69. p-bromophenacyl 4(S)-{N-[3-(3-nitropyrid-2-yldithio)propinoyl]-L-phenylalanyl-D-histidyl}amino-3(S)-hydroxy-6-methylheptanoate
70. 4(S)-[N-benzyloxycarbonyl-3-(1-naphthyl)-L-alanyl-D-histidyl]amino-3(S)-hydroxy-6-methylheptanoic acid
71. 4(S)-[N-benzyloxycarbonyl-3-(1-naphthyl)-D-alanyl-D-histidyl]amino-3(S)-hydroxy-6-methylheptanoic acid
72. ethyl 4(S)-[N-benzyloxycarbonyl-3-(1-naphthyl)-L-alanyl-D-histidyl]amino-3(S)-hydroxy-6-methylheptanoate
73. sec-butyl 4(S)-[N-acetyl-3-(1-naphthyl)-L-alanyl-D-histidyl]amino-3(S)-hydroxy-6-methylheptanoate
74. isobutyl 5(S)-[N-benzyloxycarbonyl-3-(1-naphthyl)-D-alanyl-D-histidyl]amino-4(S)-hydroxy-7-methyloctanoate
75. ethyl 4(S)-[N-benzyloxycarbonyl-3-(2-naphthyl)-L-alanyl-D-histidyl]amino-3(S)-hydroxy-6-methylheptanoate
76. methyl 3(S)-[N-benzyloxycarbonyl-3-(3-pyridyl)-L-alanyl-D-histidyl]amino-2(S)-hydroxy-5-methylhexanoate
77. ethyl 4(S)-[N-benzoyl-3-(5-quinolyl)-L-alanyl-D-histidyl]amino-3(S)-hydroxy-6-methylheptanoate
78. 4(S)-[N-benzyloxycarbonyl-3-(1-naphthyl)-L-alanyl-D-histidyl]amino-3(S)-hydroxy-5-methylheptanoic acid
79. ethyl 4(S)-[N-benzyloxycarbonyl-3-(1-naphthyl)-L-alanyl-D-histidyl]amino-3(S)-hydroxy-5-methylheptanoate
80. ethyl 4(S)-[N-benzyloxycarbonyl-3-(1-naphthyl)-D-alanyl-D-histidyl]amino-3(S)-hydroxy-5-methylheptanoate
81. benzyl 3(S)-[N-benzyloxycarbonyl-3-(1-naphthyl)-L-alanyl-D-histidyl]amino-2(S)-hydroxy-5-methylhexanoate
82. benzyl 4(S)-[N-benzyloxycarbonyl-3-(1-naphthyl)-L-alanyl-D-histidyl]amino-3(S)-hydroxy-6-methylheptanoate
83. benzyl 4(S)-[N-benzyloxycarbonyl-3-(1-naphthyl)-D-alanyl-D-histidyl]amino-3(S)-hydroxy-6-methylheptanoate
84. benzyl 4(S)-[3-(1-naphthyl)-D-alanyl-D-histidyl]amino-3(S)-hydroxy-6-methylheptanoate
85. benzyl 5(S)-[t-butoxycarbonyl-3-(1-naphthyl)-L-alanyl-D-histidyl]amino-4(S)-hydroxy-7-methyloctanoate
86. benzyl 4(S)-[t-butoxycarbonyl-3-(1-naphthyl)-L-alanyl-D-histidyl]amino-3(S)-hydroxy-5-methylheptanoate
87. benzyl 4(S)-[N-benzyloxycarbonyl-3-(1-naphthyl)-D-alanyl-D-histidyl]amino-3(S)-hydroxy-5-methylheptanoate
88. phenyl 4(S)-[N-benzyloxycarbonyl-3-(1-naphthyl)-L-alanyl-D-histidyl]amino-3(S)-hydroxy-6-methylheptanoate
89. phenacyl 4(S)-[N-benzyloxycarbonyl-3-(1-naphthyl)-L-alanyl-D-histidyl]amino-3(S)-hydroxy-6-methylheptanoate
90. p-bromophenacyl 4(S)-]N-benzyloxycarbonyl-3-(1-naphthyl)-D-alanyl-D-histidyl]amino-3(S)-hydroxy-6-methylheptanoate
91. N-butyl-3(S)-[N-benzyloxycarbonyl-3-(1-naphthyl)-L-alanyl-D-histidyl]amino-2(S)-hydroxy-5-methylhexanamide
92. N-sec-butyl-3(S)-[N-benzyloxycarbonyl-3-(1-naphthyl)-L-alanyl-D-histidyl]amino-2(S)-hydroxy-5-methylhexanamide
93. 4(S)-[N-benzyloxycarbonyl-3-(1-naphthyl)-L-alanyl-D-histidyl]amino-3(S)-hydroxy-6-methyl-N-(2-methylbutyl)heptanamide
94. N-{4(S)-[N-benzyloxycarbonyl-3-(1-naphthyl)-L-alanyl-D-histidyl]amino-3(S)-hydroxy-6-methylheptanoyl}-L-isoleucinol
95. N-benzyl-4(S)-[N-benzyloxycarbonyl-L-tyrosyl-D-histidyl]amino-3(S)-hydroxy-5-methylheptanamide
96. N-benzyl-3(S)-[N-benzyloxycarbonyl-3-(1-naphthyl)-L-alanyl-D-histidyl]amino-2(S)-hydroxy-5-methylhexanamide
97. N-benzyl-3(S)-[N-benzyloxycarbonyl-3-(1-naphthyl)-D-alanyl-D-histidyl]amino-2(S)-hydroxy-5-methylhexanamide
98. N-benzyl-3(S)-[N-benzyloxycarbonyl-3-(1-naphthyl)-L-alanyl-D-histidyl]amino-2(S)-hydroxy-4-methylhexanamide
99. 1-{3(S)-[N-benzoyl-3-(1-naphthyl)-L-alanyl-D-histidyl]amino-2(S)-hydroxy-5-methylhexanamido}-4-(m-tolyl)piperazine
100. 4-{4(S)-[N-benzyloxycarbonyl-3-(1-naphthyl)-L-alanyl-D-histidyl]amino-3(S)-hydroxy-6-methylheptanamido}-1-benzylpiperidine
101. 4-{4(S)-[N-benzyloxycarbonyl-L-tyrptophyl-D-histidyl]amino-3(S)-hydroxy-6-methylheptanamido}-1-benzylpiperidine
102. 4(S)-[N-acetyl-3-(1-naphthyl)-L-alanyl-D-histidyl]amino-3(S)-hydroxy-6-methyl-N-(2-pyridylmethyl)heptanamide 103. 4(S)-[N-benzyloxycarbonyl-3-(1-naphthyl)-D-alanyl-D-histidyl]amino-3(S)-hydroxy-6-methyl-N-(4-pyridylmethyl)heptanamide
104. N-{4(S)-[N-benzyloxycarbonyl-3-(4-chlorophenyl)-L-alanyl-L-histidyl]amino-3(S)-hydroxy-6-methylheptanoyl}-L-isoleucinol
105. 1-{4(S)-[N-benzyloxycarbonyl-3-(1-naphthyl)-L-alanyl-D-histidyl]amino-3(S)-hydroxy-6-methylheptanoyl}-4-phenylpiperidine
106. 1-{4(S)-[N-benzyloxycarbonyl-3-(1-naphthyl)-D-alanyl-D-histidyl]amino-3(S)-hydroxy-6-methylheptanoyl}-4-benzylpiperazine
107. 4(S)-[N-benzyloxycarbonyl-3-(1-naphthyl)-L-alanyl-D-histidyl]amino-3(S)-hydroxy-6-methylheptanoic acid hydrazide
108. $N^1$-{4(S)-[N-benzyloxycarbonyl-3-(1-naphthyl)-L-alanyl-D-histidyl]amino-3(S)-hydroxy-6-methylheptanoyl}-$N^2$-(4-phenylbutyryl)hydrazine
109. $N^1$-{4(S)-[N-benzyloxycarbonyl-3-(1-naphthyl)-L-alanyl-D-histidyl]amino-3(S)-hydroxy-6-methylheptanoyl}-$N^2$-(4-benzoylbutyryl)hydrazine
110. $N^1$-butyl-$N^2$-{4(S)-[N-benzyloxycarbonyl-3-(1-naphthyl)-D-alanyl-D-histidyl]amino-3(S)-hydroxy-6-methylheptanoyl}hydrazine
111. $N^1$-sec-butyl-$N^2$-{4(S)-[N-benzyloxycarbonyl-3-(1-naphthyl)-D-alanyl-D-histidyl]amino-3(S)-hydroxy-6-methylheptanoyl}hydrazine
112. 1-propionyl-3(S)-[N-benzyloxycarbonyl-3-(1-naphthyl)-L-alanyl-D-histidyl]amino-2(S)-hydroxy-5-methylhexane
113. 1-benzoyl-3(S)-[N-benzyloxycarbonyl-3-(1-naphthyl)-L-alanyl-D-histidyl]amino-2(S)-hydroxy-5-methylhexane
114. benzyl 4(S)-[N-benzyloxycarbonyl-3-(1-naphthyl)-L-alanyl-D-histidyl]amino-3(S)-mercapto-6-methylheptanoate
115. N-benzyl-4(S)-[N-benzyloxycarbonyl-3-(1-naphthyl)-L-alanyl-D-histidyl]amino-3(S)-mercapto-6-methylheptanamide
116. benzyl 4(S)-[N-benzyloxycarbonyl-3-(1-naphthyl)-L-alanyl-D-histidyl]amino-3(S)-formyl-6-methylheptanoate
117. N-benzyl-4(S)-[N-benzyloxycarbonyl-3-(1-naphthyl)-L-alanyl-D-histidyl]amino-3(S)-formyl-6-methylheptanamide
118. 1-propionyl-4(S)-[N-benzyloxycarbonyl-L-phenylalanyl-D-histidyl]amino-3(S)-formyl-6-methylheptane
119. methyl {1(S)-[N-benzyloxycarbonyl-3-(1-naphthyl)-D-alanyl-D-histidyl]amino-3-methylbutylphosphinico}acetate
120. ethyl {1(S)-[N-benzyloxycarbonyl-3-(8-quinolyl)-D-alanyl-D-histidyl]amino-3-methylbutylphosphinico}acetate
121. ethyl 4(S)-[N-benzyloxycarbonyl-3-(5-quinolyl)-D-alanyl-D-histidyl]amino-6-methylheptanoate
122. benzyl [1(RS)-{N-[N-t-butoxycarbonyl-3-(3-nitropyrid-2-yldithio)-L-alanyl]-L-phenylalanyl-D-histidyl}amino-2-methylbutylphosphinico]acetate
123. benzyl {1(S)-[N-benzyloxycarbonyl-3-(1-naphthyl)-D-alanyl-D-histidyl]amino-3-methylbutylphosphinico}acetate
124. benzyl {1(S)-[3-(1-naphthyl)-D-alanyl-D-histidyl]amino-3-methylbutylphosphinico}acetate
125. benzyl {1(S)-[N-benzyloxycarbonyl-3-(1-naphthyl)-D-alanyl-D-histidyl]amino-2-methylbutylphosphinico}acetate
126. N-benzyl-2-[1(RS)-{N-[3-(3-nitropyrid-2-yldithio)]-L-phenylalanyl-D-histidyl}amino-2-methylbutylphosphinico]acetamide
127. N-benzyl-2-{1(RS)-[N-benzyloxycarbonyl-3-(1-naphthyl)-D-alanyl-D-histidyl]amino-3-methylbutylphosphinico}acetamide
128. N-benzyl-2-{1(RS)-[N-benzyloxycarbonyl-3-(1-naphthyl)-D-alanyl-D-histidyl]amino-2-methylbutylphosphinico}acetamide
129. 4-[3-{1(RS)-[N-benzyloxycarbonyl-3-(1-naphthyl)-L-alanyl-D-histidyl]amino-3-methylbutylphosphinico}propionamido]-1-benzylpiperidine
130. ethyl 4(S)-[N-(4-phenylbutyryl)-L-phenylalanyl-DL-histidyl]amino-3(S)-hydroxy-6-methylheptanoate
131. p-bromophenacyl 4(S)-{N-[3-(3-nitropyrid-2-yldithio)-propinoyl]-L-phenylalanyl-DL-histidyl}amino-3(S)-hydroxy-6-methylheptanoate
132. 4(S)-[N-benzyloxycarbonyl-3-(1-naphthyl)-L-alanyl-DL-histidyl]amino-3(S)-hydroxy-6-methylheptanoic acid
133. 4(S)-[N-benzyloxycarbonyl-3-(1-naphthyl)-DL-alanyl-DL-histidyl]amino-3(S)-hydroxy-6-methylheptanoic acid
134. ethyl 4(S)-[N-benzyloxycarbonyl-3-(1-naphthyl)-L-alanyl-DL-histidyl]amino-3(S)-hydroxy-6-methylheptanoate
135. sec-butyl 4(S)-[N-acetyl-3-(1-naphthyl)-L-alanyl-DL-histidyl]amino-3(S)-hydroxy-6-methylheptanoate
136. isobutyl 5(S)-[N-benzyloxycarbonyl-3-(1-naphthyl)-D-alanyl-DL-histidyl]amino-4(S)-hydroxy-7-methyloctanoate
137. ethyl 4(S)-[N-benzyloxycarbonyl-3-(2-naphthyl)-L-alanyl-DL-histidyl]amino-3(S)-hydroxy-6-methylheptanoate
138. methyl 3(S)-[N-benzyloxycarbonyl-3-(3-pyridyl)-L-alanyl-DL-histidyl]amino-2(S)-hydroxy-5-methylhexanoate
139. ethyl 4(S)-[N-benzoyl-3-(5-quinolyl)-L-alanyl-DL-histidyl]amino-3(S)-hydroxy-6-methylheptanoate
140. 4(S)-[N-benzyloxycarbonyl-3-(1-naphthyl)-L-alanyl-DL-histidyl]amino-3(S)-hydroxy-5-methylheptanoic acid
141. ethyl 4(S)-[N-benzyloxycarbonyl-3-(1-naphthyl)-L-alanyl-DL-histidyl]amino-3(S)-hydroxy-5-methylheptanoate
142. ethyl 4(S)-[N-benzyloxycarbonyl-3-(1-naphthyl)-D-alanyl-DL-histidyl]amino-3(S)-hydroxy-5-methylheptanoate
143. benzyl 3(S)-[N-benzyloxycarbonyl-3-(1-naphthyl)-L-alanyl-DL-histidyl]amino-2(S)-hydroxy-5-methylhexanoate
144. benzyl 4(S)-[N-benzyloxycarbonyl-3-(1-naphthyl)-L-alanyl-DL-histidyl]amino-3(S)-hydroxy-6-methylheptanoate
145. benzyl 4(S)-[N-benzyloxycarbonyl-3-(1-naphthyl)-D-alanyl-DL-histidyl]amino-3(S)-hydroxy-6-methylheptanoate
146. benzyl 4(S)-[3-(1-naphthyl)-D-alanyl-DL-histidyl]amino-3(S)-hydroxy-6-methylheptanoate
147. benzyl 5(S)-[t-butoxycarbonyl-3-(1-naphthyl)-L-alanyl-DL-histidyl]amino-4(S)-hydroxy-7-methyloctanoate
148. benzyl 4(S)-[t-butoxycarbonyl-3-(1-naphthyl)-L-alanyl-DL-histidyl]amino-3(S)-hydroxy-5-methylheptanoate 149. benzyl 4(S)-[N-benzyloxycarbonyl-3-(1-naphthyl)-D-alanyl-DL-histidyl]amino-3(S)-hydroxy-5-methylheptanoate
150. phenyl 4(S)-[N-benzyloxycarbonyl-3-(1-naphthyl)-L-alanyl-DL-histidyl]amino-3(S)-hydroxy-6-methylheptanoate
151. phenacyl 4(S)-[N-benzyloxycarbonyl-3-(1-naphthyl)-L-alanyl-DL-histidyl]amino-3(S)-hydroxy-6-methylheptanoate
152. p-bromophenacyl 4(S)-[N-benzyloxycarbonyl-3-(1-naphthyl)-D-alanyl-DL-histidyl]amino-3(S)-hydroxy-6-methylheptanoate
153. N-butyl-3(S)-[N-benzyloxycarbonyl-3-(1-naphthyl)-L-alanyl-DL-histidyl]amino-2(S)-hydroxy-5-methylhexanamide
154. N-sec-butyl-3(S)-[N-benzyloxycarbonyl-3-(1-naphthyl)-L-alanyl-DL-histidyl]amino-2(S)-hydroxy-5-methylhexanamide
55. N-(2-methylbutyl)-4(S)-[N-benzyloxycarbonyl-3-(1-naphthyl)-L-alanyl-DL-histidyl]amino-3(S)-hydroxy-6-methylheptanamide
156. N-{4(S)-[N-benzyloxycarbonyl-3-(1-naphthyl)-L-alanyl-DL-histidyl]amino-3(S)-hydroxy-6-methylheptanoyl}-L-isoleucinol
157. N-benzyl-4(S)-[N-benzyloxycarbonyl-L-tyrosyl-DL-histidyl]amino-3(S)-hydroxy-5-methylheptanamide
158. N-benzyl-3(S)-[N-benzyloxycarbonyl-3-(1-naphthyl)-L-alanyl-DL-histidyl]amino-2(S)-hydroxy-5-methylhexanamide
159. N-benzyl-3(S)-[N-benzyloxycarbonyl-3-(1-naphthyl)-D-alanyl-DL-histidyl]amino-2(S)-hydroxy-5-methylhexanamide
160. N-benzyl-3(S)-[N-benzyloxycarbonyl-3-(1-naphthyl)-L-alanyl-DL-histidyl]amino-2(S)-hydroxy-4-methylhexanamide
161. 1-{3(S)-[N-benzoyl-3-(1-naphthyl)-L-alanyl-DL-histidyl]amino-2(S)-hydroxy-5-methylhexanamido}-4-(m-tolyl)piperazine
162. 4-{4(S)-[N-benzyloxycarbonyl-3-(1-naphthyl)-L-alanyl-DL-histidyl]amino-3(S)-hydroxy-6-methylheptanamido}-1-benzylpiperidine
163. 4-{4(S)-[N-benzyloxycarbonyl-L-tryptophyl-DL-histidyl]amino-3(S)-hydroxy-6-methylheptanamido}-1-benzylpiperidine
164. 4(S)-[N-acetyl-3-(1-naphthyl)-L-alanyl-DL-histidyl]amino-3(S)-hydroxy-6-methyl-N-(2-pyridylmethyl)heptanamide
165. 4(S)-[N-benzyloxycarbonyl-3-(1-naphthyl)-D-alanyl-DL-histidyl]amino-3(S)-hydroxy-6-methyl-N-(4-pyridylmethyl)heptanamide
166. N-{4(S)-[N-benzyloxycarbonyl-3-(4-aminophenyl)-L-alanyl-L-histidyl]amino-3(S)-hydroxy-6-methylheptanoyl}-L-isoleucinol
167. 1{4(S)-[N-benzyloxycarbonyl-3-(1-naphthyl)-L-alanyl-DL-histidyl]amino-3(S)-hydroxy-6-methylheptanoyl}-phenypiperidine
168. 1-{4(S)-[N-benzyloxycarbonyl-3-(1-naphthyl)-D-alanyl-DL-histidyl]amino-3(S)-hydroxy-6-methylheptanoyl}-4-benzylpiperazine
169. 4(S)-[N-benzyloxycarbonyl-3-(1-naphthyl)-L-alanyl-DL-histidyl]amino-3(S)-hydroxy-6-methylheptanoic acid hydrazide
170. $N^1$-{4(S)-[N-benzyloxycarbonyl-3-(1-naphthyl)-L-alanyl-DL-histidyl]amino-3(S)-hydroxy-6-methylheptanoyl}-$N^2$-(4-phenylbutyryl)hydrazine
171. $N^1$-{4(S)-[N-benzyloxycarbonyl-3-(1-naphthyl)-L-alanyl-DL-histidyl]amino-3(S)-hydroxy-6-methylheptanoyl}-$N^2$-(4-benzoylbutyryl)hydrazine
172. $N^1$-butyl-$N^2$-{4(S)-[N-benzyloxycarbonyl-3-(1-naphthyl)-D-alanyl-DL-histidyl]amino-3(S)-hydroxy-6-methylheptanoyl}hydrazine
173. $N^1$-sec-butyl-$N^2$-{4(S)-[N-benzyloxycarbonyl-3-(1-naphthyl)-D-alanyl-DL-histidyl]amino-3(S)-hydroxy-6-methylheptanoyl}hydrazine
174. 1-propionyl-3(S)-[N-benzyloxycarbonyl-3-(1-naphthyl)-L-alanyl-DL-histidyl]amino-2(S)-hydroxy-5-methylhexane
175. 1-benzoyl-3(S)-[N-benzyloxycarbonyl-3-(1-naphthyl)-L-alanyl-DL-histidyl]amino-2(S)-hydroxy-5-methylhexane
176. benzyl 4(S)-[N-benzyloxycarbonyl-3-(1-naphthyl)-L-alanyl-DL-histidyl]amino-3(S)-mercapto-6-methylheptanoate
177. N-benzyl-4(S)-[N-benzyloxycarbonyl-3-(1-naphthyl)-L-alanyl-DL-histidyl]amino-3(S)-mercapto-6-methylheptanamide
178. benzyl 4(S)-[N-benzyloxycarbonyl-3-(1-naphthyl)-L-alanyl-DL-histidyl]amino-3(S)-formyl-6-methylheptanoate
179. N-benzyl-4(S)-[N-benzyloxycarbonyl-3-(1-naphthyl)-L-alanyl-DL-histidyl]amino-3(S)-formyl-6-methylheptanamide
180. 1-propionyl-4(S)-[N-benzyloxycarbonyl-L-phenylalanyl-DL-histidyl]amino-3(S)-formyl-6-methylheptane
181. methyl {1(S)-[N-benzyloxycarbonyl-3-(1-naphthyl)-D-alanyl-DL-histidyl]amino-3-methylbutylphosphinico}acetate
182. ethyl {1(S)-[N-benzyloxycarbonyl-3-(8-quinolyl)-D-alanyl-DL-histidyl]amino-3-methylbutylphosphinico}acetate
183. ethyl 4(S)-[N-benzyloxycarbonyl-3-(5-quinolyl)-D-alanyl-DL-histidyl]amino-6-methylheptanoate
184. benzyl [1(RS)-{N-[N-t-butoxycarbonyl-S-(3-nitropyrid-2-ylthio)-L-cysteinyl]-L-phenylalanyl-DL-histidyl}amino-2-methylbutylphosphinico]acetate
185. benzyl {1(S)-[N-benzyloxycarbonyl-3-(1-naphthyl)-D-alanyl-DL-histidyl]amino-3-methylbutylphosphinico}acetate
186. benzyl {1(S)-[3-(1-naphthyl)-D-alanyl-DL-histidyl]amino-3-methylbutylphospinico}acetate
187. benzyl {1(S)-[N-benzyloxycarbonyl-3-(1-naphthyl)-D-alanyl-DL-histidyl]amino-2-methylbutylphosphinico}acetate
158. N-benzyl-2-[1(RS)-{N-[3-(3-nitropyrid-2-yldithio)-L-phenylalanyl-DL-histidyl}amino-2-methylbutylphosphinico]acetamide
189. N-benzyl-2-{1(RS)-[N-benzyloxycarbonyl-3-(1-naphthyl)-D-alanyl-DL-histidyl]amino-3-methylbutylphosphinico}acetamide
190. N-benzyl-2-{1(RS)-[N-benzyloxycarbonyl-3-(1-naphthyl)-D-alanyl-DL-histidyl]amino-2-methylbutylphosphinico}acetamide
191. 4-[3-{1(RS)-[N-benzyloxycarbonyl-3-(1-naphthyl)-L-alanyl-DL-histidyl]amino-3-methylbutylphosphinico}propionamido]-1-benzylpiperidine
192. ethyl 4(S)-[N-benzyloxycarbonyl-3-(1-naphthyl)-L-alanyl-L-norleucyl]amino-3(S)-hydroxy-6-methylheptanoate
193. 2-methylbutyl 4(S)-[N-benzyloxycarbonyl-3-(1-naphthyl)-L-alanyl-L-norleucyl]amino-3(S)-hydroxy-6-methylheptanoate 194. 4(S)-[N-benzyloxycarbonyl-3-(1-naphthyl)-L-alanyl-L-norleucyl]amino-3(S)-hydroxy-6-methylheptanamide
195. N-sec-butyl-4(S)-[N-benzyloxycarbonyl-3-(1-naphthyl)-L-alanyl-L-norleucyl]amino-3(S)-hydroxy-6-methylheptanamide
196. N-(2-methylbutyl)-4(S)-[N-benzyloxycarbonyl-3-(1-naphthyl)-L-alanyl-L-norleucyl]amino-3(S)-hydroxy-6-methylheptanamide
197. N-{4(S)-[N-benzyloxycarbonyl-3-(1-naphthyl)-L-alanyl-L-norleucyl]amino-3(S)-hydroxy-6-methylheptanoyl}-L-isoleucinol
198. 4-{4(S)-[N-benzyloxycarbonyl-3-(1-napthyl)-L-alanyl-L-norleucyl]amino-3(S)-hydroxy-6-methylheptanamido}-1-benzylpiperidine
199. 4(S)-[N-benzyloxycarbonyl-3-(1-naphthyl)-L-alanyl-L-norleucyl]amino-3(S)-hydroxy-6-methyl-N-[2-(2-pyridyl)ethyl]heptanamide
200. 4(S)-[N-benzyloxycarbonyl-3-(1-naphthyl)-L-alanyl-L-norleucyl]amino-3(S)-hydroxy-6-methyl-N-(2-morpholinoethyl)heptanamide
201. N-ethyl-N-(2-methylbutyl)-4(S)-[N-benzyloxycarbonyl-3-(1-naphthyl)-L-alanyl-L-norleucyl]amino-3(S)-hydroxy-6-methylheptanamide
202. $N^1$-(4-benzoylbutyryl)-$N^2$-{4(S)-[N-benzyloxycarbonyl-3-(1-naphthyl)-L-alanyl-L-norleucyl]amino-3(S)-hydroxy-6-methylheptanoyl}hydrazine
203. ethyl 4(S)-[N-benzyloxycarbonyl-3-(1-naphthyl)-L-alanyl-L-leucyl]amino-3(S)-hydroxy-6-methylheptanoate
204. 2-methylbutyl 4(S)-[N-benzyloxycarbonyl-3-(1-naphthyl)-L-alanyl-L-leucyl]amino-3(S)-hydroxy-6-methylheptanoate
205. 4(S)-[N-benzyloxycarbonyl-3-(1-naphthyl)-L-alanyl-L-leucyl]amino-3(S)-hydroxy-6-methylheptanamide
206. N-sec-butyl-4(S)-[N-benzyloxycarbonyl-3-(1-naphthyl)-L-alanyl-L-leucyl]amino-3(S)-hydroxy-6-methylheptanamide
207. N-(2-methylbutyl)-4(S)-[N-benzyloxycarbonyl-3-(1-naphthyl)-L-alanyl-L-leucyl]amino-3(S)-hydroxy-6-methylheptanamide
208. N-{4(S)-[N-benzyloxycarbonyl-3-(1-naphthyl)-L-alanyl-L-leucyl]amino-3(S)-hydroxy-6-methylheptanoyl}-L-isoleucinol
209. 4-{4(S)-[N-benzyloxycarbonyl-3-(1-naphthyl)-L-alanyl-L-leucyl]amino-3(S)-hydroxy-6-methylheptanamido}-1-benzylpiperidine
210. 4(S)-[N-benzyloxycarbonyl-3-(1-naphthyl)-L-alanyl-L-leucyl]amino-3(S)-hydroxy-6-methyl-N-[2-(2-pyridyl)ethyl]heptanamide
211. 4(S)-[N-benzyloxycarbonyl-3-(1-naphthyl)-L-alanyl-L-leucyl]amino-3(S)-hydroxy-6-methyl-N-(2-morpholinoethyl)heptanamide
212. N-ethyl-N-(2-methylbutyl)-4(S)-[N-benzyloxycarbonyl-3-(1naphthyl)-L-alanyl-L-leucyl]amino-3(S)-hydroxy-6-methylheptanamide
213. $N^1$-(4-benzoylbutyryl)-$N^2$-{4(S)-[N-benzyloxycarbonyl-3-(1-naphthyl)-L-alanyl-L-leucyl]amino-3(S)-hydroxy-6-methylheptanoyl}hydrazine
214. ethyl 4(S)-[N-benzyloxycarbonyl-3-(1-naphthyl)-L-alanyl-3-(2-thienyl)-DL-alanyl]amino-3(S)-hydroxy-6-methylheptanoate
215. 2-methylbutyl 4-(S)-[N-benzyloxycarbonyl-3-(1-naphthyl)-L-alanyl-3-(2-thienyl)-DL-alanyl]amino-3(S)-hydroxy-6-methylheptanoate
216. N-sec-butyl 4(S)-[N-benzyloxycarbonyl-3-(1-naphthyl)-L-alanyl-3-(2-thienyl)-DL-alanyl]amino-3(S)-hydroxy-6-methylheptanamide
217. N-(2-methylbutyl)-4(S)-[N-benzyloxycarbonyl-3-(1-naphthyl)-L-alanyl-3-(2-thienyl)-DL-alanyl]amino-3(S)-hydroxy-6-methylheptanamide
218. N-{4(S)-[N-benzyloxycarbonyl-3-(1-naphthyl)-L-alanyl-3-(2-thienyl)-DL-alanyl]amino-3(S)-hydroxy-6-methylheptanoyl}-L-isoleucinol
219. 4-{4(S)-[N-benzyloxycarbonyl-3-(1-naphthyl)-L-alanyl-3-(2-thienyl)-DL-alanyl]amino-3(S)-hydroxy-6-methylheptanamido}-benzylpiperidine
220. 4(S)-[N-benzyloxycarbonyl-3-(1-naphthyl)-L-alanyl-3-(2-thienyl)-DL-alanyl]amino-3(S)-hydroxy-6-methyl-N-[2-(2-pyridyl)ethyl]heptanamide
221. 4(S)-[N-benzyloxycarbonyl-3-(1-naphthyl)-L-alanyl-3-(2-thienyl)-DL-alanyl]amino-3(S)-hydroxy-6-methyl-N-(2-morpholinoethyl)heptanamide
222. N-ethyl-N-(2-methylbutyl)-4(S)-[N-benzyloxycarbonyl-3-(1-naphthyl)-L-alanyl-3-(2-thienyl)-DL-alanyl]amino-3-(S)-hydroxy-6-methylheptanamide
223. $N^1$-(4-benzoylbutyryl)-$N^2$-{4(S)-[N-benzyloxycarbonyl-3-(1-naphthyl)-L-alanyl-3-(2-thienyl)-DL-alanyl]amino-3(S)-hydroxy-6-methylheptanoyl}hydrazine
224. ethyl 4(S)-[N-benzyloxycarbonyl-3-(1-naphthyl)-L-alanyl-3-(1,3-thiazol-2-yl)-DL-alanyl]amino-3(S)-hydroxy-6-methylheptanoate
225. 2-methylbutyl 4(S)-[N-benzyloxycarbonyl-3-(1-naphthyl)-L-alanyl-3-(1,3-thiazol-2-yl)-DL-alanyl]amino-3(S)-hydroxy-6-methylheptanoate
226. N-sec-butyl-4(S)-[N-benzyloxycarbonyl-3-(1-naphthyl)-L-alanyl-3-(1,3-thiazol-2-yl)-DL-alanyl]amino-3(S)-hydroxy-6-methylheptanamide
227. N-(2-methylbutyl)-4(S)-[N-benzyloxycarbonyl-3-(1-naphthyl)-L-alanyl-3-(1,3-thiazol-2-yl)-DL-alanyl]amino-3(S)-hydroxy-6-methylheptanamide
228. N-{4(S)-[N-benzyloxycarbonyl-3-(1-naphthyl)-L-alanyl-3-(4-thiazolyl)-DL-alanyl]amino-3(S)-hydroxy-6-methylheptanoyl}-L-isoleucinol
229. 4-{4(S)-[N-benzyloxycarbonyl-3-(1-naphthyl)-L-alanyl-3-(1,3-thiazol-2-yl)-DL-alanyl]amino-3(S)-hydroxy-6-methylheptanamido}-1-benzylpiperidine
230. 4(S)-[N-benzyloxycarbonyl-3-(1-naphthyl)-L-alanyl-3-(1,3-thiazol-2-yl)-DL-alanyl]amino-3(S)-hydroxy-6-methyl-N-[2-(2-pyridyl)ethyl]heptanamide
231. 4(S)-[N-benzyloxycarbonyl-3-(1-naphthyl)-L-alanyl]-3-(1,3-thiazol-2-yl)-DL-alanyl]amino-3(S)-hydroxy-6-methyl-N-(2-morpholinoethyl)heptanamide
232. N-ethyl-N-(2-methylbutyl)-4(S)-[N-benzyloxycarbonyl-3-(1-naphthyl)-L-alanyl-3-(1,3-thiazol-2-yl)-DL-alanyl]amino-3(S)-hydroxy-6-methylheptanamide
233. $N^1$-(4-benzoylbutyryl)-$N^2$-{4(S)-[N-benzyloxycarbonyl-3-(1-naphthyl)-L-alanyl-3-(1,3-thiazol-2-yl)-DL-alanyl]amino-3(S)-hydroxy-6-methylheptanoyl}hydrazine
234. ethyl 4(S)-[N-benzyloxycarbonyl-3-(1-naphthyl)-L-alanyl-3-(1,3-thiazol-4-yl)-DL-alanyl]amino-3(S)-hydroxy-6-methylheptanoate
235. 2-methylbutyl 4(S)-[N-benzyloxycarbonyl-3-(1-naphthyl)-L-alanyl-3-(1,3-thiazol-4-yl)-DL-alanyl]amino-3(S)-hydroxy-6-methylheptanoate
236. 4(S)-[N-benzyloxycarbonyl-3-(1-naphthyl)-L-alanyl-3-(1,3-thiazol-4-yl)-DL-alanyl]amino-3(S)-hydroxy-6-methylheptanamide 237. N-sec-butyl-4(S)-[N-benzyloxycarbonyl-3-(1-naphthyl)-L-alanyl-3-(1,3-thiazol-4-yl)-DL-alanyl]amino-3(S)-hydroxy-6-methylheptanamide
238. N-(2-methylbutyl)-4(S)-[N-benzyloxycarbonyl-3-(1-naphthyl)-L-alanyl-3-(1,3-thiazol-4-yl)-DL-alanyl]amino-3(S)-hydroxy-6-methylheptanamide
239. N-{4(S)-[N-benzyloxycarbonyl-3-(1-naphthyl)-L-alanyl-3-(1,3-thiazol-4-yl)-DL-alanyl]amino-3(S)-hydroxy-6-methylheptanoyl}-L-isoleucinol
240. 4-{4(S)-[N-benzyloxycarbonyl-3-(1-naphthyl)-L-alanyl-3-(1,3-thiazol-4-yl)-DL-alanyl]amino-3(S)-hydroxy-6-methylheptanamido}-1-benzylpiperidine
241. 4(S)-[N-benzyloxycarbonyl-3-(1-naphthyl)-L-alanyl-3-(4-thiazolyl)-DL-alanyl]amino-3(S)-hydroxy-6-methyl-N-[2-(2-pyridyl)ethyl]heptanamide
242. 4(S)-[N-benzyloxycarbonyl-3-(1-naphthyl)-L-alanyl-3-(4-thiazolyl)-DL-alanyl]amino-3(S)-hydroxy-6-methyl-N-(2-morpholinoethyl)heptanamide
243. N-(2-phenylpropyl)-4(S)-[N-benzyloxycarbonyl-3-(1-naphthyl)-L-alanyl-3-(4-thiazolyl)-DL-alanyl]amino-3(S)-hydroxy-6-methylheptanamide
244. N$^1$-(4-benzoylbutyryl)-N$^2$-{4(S)-[N-benzyloxycarbonyl-3-(1-naphthyl)-L-alanyl-3-(1,3-thiazol-4-yl)-DL-alanyl]amino-3(S)-hydroxy-6-methylheptanoyl}hydrazine
245. ethyl 4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanoate
246. 2-methylbutyl 4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanoate
247. N-sec-butyl-4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanamide
248. N-(2-methylbutyl)-4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanamide
249. N-{4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanoyl}-L-isoleucinol
250. 4-{4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanamido}-1-benzylpiperidine
251. 4(S)-[N-benzyloxycarbonyl-3-(1-naphthyl)-L-alanyl-3-(4-methyl-1,3-thiazol-5-yl)-DL-alanyl]amino-3(S)-hydroxy-6-methyl-N-[2-(2-pyridyl)ethyl]heptanamide
252. 4(S)-[N-benzyloxycarbonyl-3-(1-naphthyl)-L-alanyl-3-(4-methyl-1,3-thiazol-5-yl)-DL-alanyl]amino-3(S)-hydroxy-6-methyl-N-(2-morpholinoethyl)heptanamide
253. N-ethyl-N-(2-methylbutyl)-4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanamide
254. N$^1$-(4-benzoylbutyryl)-N$^2$-{4(S)-[N-benzyloxycarbonyl-3-(1-naphthyl)-L-alanyl-3-(4-methyl-1,3-thiazol-5-yl)-DL-alanyl]amino-3(S)-hydroxy-6-methylheptanoyl}hydrazine
255. ethyl 4(S)-[N-benzyloxycarbonyl-3-(1-naphthyl)-L-alanyl-3-(2-pyridyl)-DL-alanyl]amino-3(S)-hydroxy-6-methylheptanoate
256. 2-methylbutyl 4(S)-[N-benzyloxycarbonyl-3-(1-naphthyl)-L-alanyl-3-(2-pyridyl)-DL-alanyl]amino-3(S)-hydroxy-6-methylheptanoate
257. N-sec-butyl-4(S)-[N-benzyloxycarbonyl-3-(1-naphthyl)-L-alanyl-3-(2-pyridyl)-DL-alanyl]amino-3(S)-hydroxy-6-methylheptanamide
258. N-(2-methylbutyl)-4(S)-[N-benzyloxycarbonyl-3-(1-naphthyl)-L-alanyl-3-(2-pyridyl)-DL-alanyl]amino-3(S)-hydroxy-6-methylheptanamide
259. N-{4(S)-[N-benzyloxycarbonyl-3-(1-naphthyl)-L-alanyl-3-(2-pyridyl)-DL-alanyl]amino-3(S)-hydroxy-6-methylheptanoyl}-L-isoleucinol
260. 4-{4(S)-N-benzyloxycarbonyl-3-(1-naphthyl)-L-alanyl-3-(2-pyridyl)-DL-alanyl]amino-2(S)-hydroxy-6-methylheptanamido}-1-benzylpiperidine
261. 4(S)-[N-benzyloxycarbonyl-3-(1-naphthyl)-L-alanyl-3-(2-pyridyl)-DL-alanyl]amino-3(S)-hydroxy-6-methyl-N-[2-(2-pyridyl)ethyl]heptanamide
262. 4(S)-[N-benzyloxycarbonyl-3-(1-naphthyl)-L-alanyl-3-(2-pyridyl)-DL-alanyl]amino-3(S)-hydroxy-6-methyl-N-(2-morpholinoethyl)heptanamide
263. N-(2-phenylpropyl)-4(S)-[N-benzyloxycarbonyl-3-(1-naphthyl)-L-alanyl-3-(2-pyridyl)-DL-alanyl]amino-3-(S)-hydroxy-6-methylheptanamide
264. N$^1$-(4-benzoylbutyryl)-N$^2$-{4(S)-[N-benzyloxycarbonyl-3-(1-naphthyl)-L-alanyl-3-(2-pyridyl)-DL-alanyl]amino-3(S)-hydroxy-6-methylheptanoyl}hydrazine
265. ethyl 4(S)-[N-benzyloxycarbonyl-3-(1-naphthyl)-L-alanyl-3-(3-pyridyl)-DL-alanyl]amino-3(S)-hydroxy-6-methylheptanoate
266. 2-methylbutyl 4(S)-[N-benzyloxycarbonyl-3-(1-naphthyl)-L-alanyl-3-(3-pyridyl)-DL-alanyl]amino-3(S)-hydroxy-6-methylheptanoate
267. N-sec-butyl-4-(S)-[N-benzyloxycarbonyl-3-(1-naphthyl)-L-alanyl-3-(3-pyridyl)-DL-alanyl]amino-3(S)-hydroxy-6-methylheptanamide
268. N-(2-methylbutyl)-4(S)-[N-benzyloxycarbonyl-3-(1-naphthyl)-L-alanyl-3-(3-pyridyl)-DL-alanyl]amino-3(S)-hydroxy-6-methylheptanamide
269. N-{4(S)-[N-benzyloxycarbonyl-3-(1-naphthyl)-L-alanyl-3-(3-pyridyl)-DL-alanyl]amino-3(S)-hydroxy-6-methylheptanoyl}-L-isoleucinol
270. 4-{4(S)-[N-benzyloxycarbonyl-3-(1-naphthyl)-L-alanyl-3-(3-pyridyl)-DL-alanyl]amino-3(S)-hydroxy-6-methylheptanamido}-1-benzylpiperidine
271. 4(S)-[N-benzyloxycarbonyl-3-(1-naphthyl)-L-alanyl-3-(3-pyridyl)-DL-alanyl]amino-3(S)-hydroxy-6-methyl-N-[2-(2-pyridyl)ethyl]heptanamide
272. 4(S)-[N-benzyloxycarbonyl-3-(1-naphthyl)-L-alanyl-3-(3-pyridyl)-DL-alanyl]amino-3(S)-hydroxy-6-methyl-N-(2-morpholinoethyl)heptanamide
273. N-ethyl-N-(2-methylbutyl)-4(S)-[N-benzyloxycarbonyl-3-(1-naphthyl)-L-alanyl-3-(3-pyridyl)-DL-alanyl]amino-3(S)-hydroxy-6-methylheptanamide
274. N$^1$-(4-benzoylbutyryl)-N$^2$-{4(S)-benzyloxy-carbonyl-3-(1-naphthyl)-L-alanyl-3-(3-pyridyl)-DL-alanyl]amino-3(S)-hydroxy-6-methylheptanoyl}hydrazine
275. ethyl 4(S)-[N-benzyloxycarbonyl-3-(1-naphthyl)-L-alanyl-3-(4-pyridyl)-DL-alanyl]amino-3(S)-hydroxy-6-methylheptanoate
276. 2-methylbutyl 4(S)-[N-benzyloxycarbonyl-3-(1-naphthyl)-L-alanyl-3-(4-pyridyl)-DL-alanyl]amino-3(S)-hydroxy-6-methylheptanoate
277. N-sec-butyl-4(S)-[N-benzyloxycarbonyl-3-(1-naphthyl)-L-alanyl-3-(4-pyridyl)-DL-alanyl]amino-3(S)-hydroxy-6-methylheptanamide
278. N-(2-methylbutyl)-4(S)-[N-benzyloxycarbonyl-3-(1-naphthyl)-L-alanyl-3-(4-pyridyl)-DL-alanyl]amino-3(S)-hydroxy-6-methylheptanamide 279. N-{4(S)-[N-benzyloxycarbonyl-3-(1-naphthyl)-L-alanyl-3-(4-pyridyl)-DL-alanyl]amino-3(S)-hydroxy-6-methylheptanoyl}-L-isoleucinol
280. 4-{4(S)-[N-benzyloxycarbonyl-3-(1-naphthyl)-L-alanyl-3-(4-pyridyl)-DL-alanyl]amino-3(S)-hydroxy-6-methylheptanamido}-1-benzylpiperidine
281. 4(S)-[N-benzyloxycarbonyl-3-(1-naphthyl)-L-alanyl-3-(4-pyridyl)-DL-alanyl]amino-3(S)-hydroxy-6-methyl-N-[2-(2-pyridyl)ethyl]heptanamide
282. 4(S)-[N-benzyloxycarbonyl-3-(1-naphthyl)-L-alanyl-3-(4-pyridyl)-DL-alanyl]amino-3(S)-hydroxy-6-methyl-N-(2-morpholinoethyl)heptanamide
283. N-ethyl-N-(2-methylbutyl)-4(S)-[N-benzyloxycarbonyl-3-(1-naphthyl)-L-alanyl-3-(4-pyridyl)-DL-alanyl]amino-3(S)-hydroxy-6-methylheptanamide
284. $N^1$-(4-benzoylbutyryl)-$N^2$-{4(S)-[N-benzyloxycarbonyl-3-(1-naphthyl)-L-alanyl-3-(4-pyridyl)-DL-alanyl]amino-3(S)-hydroxy-6-methylheptanoyl}hydrazine
285. N-(2-methylbutyl)-4(S)-[N-benzyloxycarbonyl-3-(1-naphthyl)-L-alanyl-L-norleucyl]amino-3(S)-hydroxy-5-methylheptanamide
286. N-{4(S)-[N-benzyloxycarbonyl-3-(1-naphthyl)-L-alanyl-L-norleucyl]amino-3(S)-hydroxy-5-methylheptanoyl}-L-isoleucinol
287. N-(2-methylbutyl)-4(S)-[N-benzyloxycarbonyl-3-(1-naphthyl)-L-alanyl-L-leucyl]amino-3(S)-hydroxy-5-methylheptanamide
288. N-{4(S)-[N-benzyloxycarbonyl-3-(1-naphthyl)-L-alanyl-L-leucyl]amino-3(S)-hydroxy-5-methylheptanoyl}-L-isoleucinol
289. N-(2-methylbutyl)-4(S)-[N-benzyloxycarbonyl-3-(1-naphthyl)-L-alanyl-3-(2-thienyl)-DL-alanyl]amino-3(S)-hydroxy-5-methylheptanamide
290. N-{4(S)-[N-benzyloxycarbonyl-3-(1-naphthyl)-L-alanyl-3-(2-thienyl)-DL-alanyl]amino-3(S)-hydroxy-5-methylheptanoyl}-L-isoleucinol
291. N-(2-methylbutyl)-4(S)-[N-benzyloxycarbonyl-3-(1-naphthyl)-L-alanyl-3-(2-thiazolyl)-DL-alanyl]amino-3(S)-hydroxy-5-methylheptanamide
292. N-{4(S)-[N-benzyloxycarbonyl-3-(1-naphthyl)-L-alanyl-3-(2-thiazolyl)-DL-alanyl]amino-3(S)-hydroxy-5-methylheptanoyl}-L-isoleucinol
293. N-(2-methylbutyl)-4(S)-[N-benzyloxycarbonyl-3-(1-naphthyl)-L-alanyl-3-(4-thiazolyl)-DL-alanyl]amino-3(S)-hydroxy-5-methylheptanamide
294. N-{4(S)-N-benzyloxycarbonyl-3-(1-naphthyl)-L-alanyl-3-(4-thiazolyl)-DL-alanyl]amino-3(S)-hydroxy-5-methylheptanoyl}-L-isoleucinol
295. N-(2-methylbutyl)-4(S)-[N-benzyloxycarbonyl-3-(1-naphthyl)-L-alanyl-3-(4-methyl-1,3-thiazol-5-yl)-DL-alanyl]amino-3(S)-hydroxy-5-methylheptanamide
296. N-{4(S)-[N-benzyloxycarbonyl-3-(1-naphthyl)-L-alanyl-3-(4-methyl-1,3-thiazol-5-yl)-DL-alanyl]amino-3(S)-hydroxy-5-methylheptanoyl}-L-isoleucinol
297. N-(2-methylbutyl)-4(S)-[N-benzyloxycarbonyl-3-(1-naphthyl)-L-alanyl-3-(2-pyridyl)-DL-alanyl]amino-3(S)-hydroxy-5-methylheptanamide
298. N-{4(S)-[N-benzyloxycarbonyl-3-(1-naphthyl)-L-alanyl-3-(2-pyridyl)-DL-alanyl]amino-3(S)-hydroxy-5-methylheptanoyl}-L-isoleucinol
299. N-(2-methylbutyl)-4(S)-[N-benzyloxycarbonyl-3-(1-naphthyl)-L-alanyl-3-(3-pyridyl)-DL-alanyl]amino-3(S)-hydroxy-5-methylheptanamide
300. N-{4(S)-[N-benzyloxycarbonyl-3-(1-naphthyl)-L-alanyl-3-(3-pyridyl)-DL-alanyl]amino-3(S)-hydroxy-5-methylheptanoyl}-L-isoleucinol
301. N-(2-methylbutyl)-4(S)-[N-benzyloxycarbonyl-3-(1-naphthyl)-L-alanyl-3-(4-pyridyl)-DL-alanyl]amino-3(S)-hydroxy-5-methylheptanamide
302. N-{4(S)-[N-benzyloxycarbonyl-3-(1-naphthyl)-L-alanyl-3-(4-pyridyl)-DL-alanyl]amino-3(S)-hydroxy-5-methylheptanoyl}-L-isoleucinol
303. N-(2-methylbutyl)-4(S)-[N-benzyloxycarbonyl-3-(1-naphthyl)-L-alanyl-3-cyclopentyl-DL-alanyl]amino-3(S)-hydroxy-6-methylheptanamide
304. N-{4(S)-[N-benzyloxycarbonyl-3-(1-naphthyl)-L-alanyl-3-cyclopentyl-DL-alanyl]amino-3(S)-hydroxy-6-methylheptanoyl}-L-isoleucinol
305. N-(2-methylbutyl)-4(S)-[N-benzyloxycarbonyl-3-(1-naphthyl)-L-alanyl-L-phenylalanyl]amino-3(S)-hydroxy-6-methylheptanamide
306. N-{4(S)-[N-benzyloxycarbonyl-3-(1-naphthyl)-L-alanyl-L-phenylalanyl]amino-3(S)-hydroxy-6-methylheptanoyl}-L-isoleucinol
307. N-(2-methylbutyl)-4(S)-[N-benzyloxycarbonyl-3-(1-naphthyl)-L-alanyl-3-(1-naphthyl)-L-alanyl]amino-3(S)-hydroxy-6-methylheptanamide
308. N-{4(S)-[N-benzyloxycarbonyl-3-(1-naphthyl)-L-alanyl-3-(1-naphthyl)-L-alanyl]amino-3(S)-hydroxy-6-methylheptanoyl}-L-isoleucinol
309. N-(2-methylbutyl)-4(S)-[N-benzyloxycarbonyl-3-(1-naphthyl)-L-alanyl-L-tryptophyl]amino-3(S)-hydroxy-6-methylheptanamide
310. N-{4(S)-[N-benzyloxycarbonyl-3-(1-naphthyl)-L-alanyl-L-tryptophyl]amino-3(S)-hydroxy-6-methylheptanoyl}-L-isoleucinol
311. N-(2-methylbutyl)-4(S)-[N-benzyloxycarbonyl-3(1-naphthyl)-L-alanyl-L-valyl]amino-3(S)-hydroxy-6-methylheptanamide
312. N-{4(S)-[N-benzyloxycarbonyl-3-(1-naphthyl)-L-alanyl-L-valyl]amino-3(S)-hydroxy-6-methylheptanoyl}-L-isoleucinol
313. N-(2-methylbutyl)-4(S)-[N-benzyloxycarbonyl-3-(1-naphthyl)-L-alanyl-L-isoleucyl]amino-3(S)-hydroxy-6-methylheptanamide
314. N-{4(S)-[N-benzyloxycarbonyl-3-(1-naphthyl)-L-alanyl-L-isoleucyl]amino-3(S)-hydroxy-6-methylheptanyl}-L-isoleucinol
315. N-(2-methylbutyl)-1-{4(S)-[N-benzyloxycarbonyl-3-(1-naphthyl)-L-alanyl-L-norvalyl]amino-3(S)-hydroxy-6-methylheptanamide}
316. N-{4(S)-[N-benzyloxycarbonyl-3-(1-naphthyl)-L-alanyl-L-norvalyl]amino-3(S)-hydroxy-6-methylheptanoyl}-L-isoleucinol
317. N-(2-methylbutyl)-4(S)-[N-benzyloxycarbonyl-3-(1-naphthyl)-L-alanyl-3-(2-pyrrolidinyl)-L-alanyl]amino-3(S)-hydroxy-6-methylheptanamide
318. N-{4(S)-[N-benzyloxycarbonyl-3-(1-naphthyl)-L-alanyl-3-(2-pyrrolidinyl)-L-alanyl]amino-3(S)-hydroxy-6-methylheptanoyl}-L-isoleucinol
319. N-(2-methylbutyl)-4(S)-[N-benzyloxycarbonyl-3-(1-naphthyl)-L-alanyl-3-(1-methyl-2-pyrrolidinyl)-L-alanyl]amino-3(S)-hydroxy-6-methylheptanamide
320. N-{4(S)-[N-benzyloxycarbonyl-3-(1-naphthyl)-L-alanyl-3-(1-methyl-2-pyrrolidinyl)-L-alanyl]amino-3(S)-hydroxy-6-methylheptanoyl}-L-isoleucinol
321. N-(2-methylbutyl)-4(S)-[N-benzyloxycarbonyl-3-(1-naphthyl)-L-alanyl-3-(1,3-thiazolidin-4-yl)-L-alanyl]amino-3(S)-hydroxy-6-methylheptanamide 322. N-{4(S)-[N-benzyloxycarbonyl-3-(1-naphthyl)-L-alanyl-3-(1,3-thiazolidin-4-yl)-L-alanyl]amino-3(S)-hydroxy-6-methylheptanoyl}-L-isoleucinol
323. N-(2-methylbutyl)-4(S)-[N-benzyloxycarbonyl-3-(1-naphthyl)-L-alanyl-3-(3-methyl-1,3-thiazolidin-4-yl)-L-alanyl]amino-3(S)-hydroxy-6-methylheptanamide
324. N-{4(S)-[N-benzyloxycarbonyl-3-(1-naphthyl)-L-alanyl-3-(3-methyl-1,3-thiazolidin-4-yl)-L-alanyl]amino-3(S)-hydroxy-6-methylheptanoyl}-L-isoleucinol
325. N-(2-methylbutyl)-4(S)-{2(S)-[N-benzyloxycarbonyl-3-(1-naphthyl)-L-alanyl]aminoheptanoyl}amino-3(S)-hydroxy-6-methylheptanamide
326. N-[4(S)-{2(S)-[N-benzyloxycarbonyl-3-(1-naphthyl)-L-alanyl]aminoheptanoyl}amino-3(S)-hydroxy-6-methylheptanoyl]-L-isoleucinol
327. N-(2-methylbutyl)-4(S)-{2(S)-[N-benzyloxycarbonyl-3-(1-naphthyl)-L-alanyl]aminononanoyl}amino-3(S)-hydroxy-6-methylheptanamide
328. N-[4(S)-{2(S)-[N-benzyloxycarbonyl-3-(1-naphthyl)-L-alanyl]aminononanoyl}amino-3(S)-hydroxy-6-methylheptanoyl]-L-isoleucinol
329. N-(2-methylbutyl)-4(S)-{2(S)-[N-benzyloxycarbonyl-3-(1-naphthyl)-L-alanyl]aminododecanoyl}amino-3(S)-hydroxy-6-methylheptanamide
330. N-[4(S)-{2(S)-[N-benzyloxycarbonyl-3-(1-naphthyl)-L-alanyl]aminododecanoyl}amino-3(S)-hydroxy-6-methylheptanoyl]-L-isoleucinol
331. N-(2-methylbutyl)-4(S)-{2(S)-[N-benzyloxycarbonyl-3-(1-naphthyl)-L-alanyl]aminopent-4-enoyl}amino-3(S)-hydroxy-6-methylheptanamide
332. N-[4(S)-{2(S)-[N-benzyloxycarbonyl-3-(1-naphthyl)-L-alanyl]aminopent-4-enoyl}amino-3(S)-hydroxy-6-methylheptanoyl]-L-isoleucinol
333. N-(2-methylbutyl)-4(S)-{2(S)-[N-benzyloxycarbonyl-3-(1-naphthyl)-L-alanyl]aminopent-4-ynoyl}amino-3(S)-hydroxy-6-methylheptanamide
334. N-[4(S)-{2(S)-[N-benzyloxycarbonyl-3-(1-naphthyl)-L-alanyl]aminopent-4-ynoyl}amino-3(S)-hydroxy-6-methylheptanoyl]-L-isoleucinol
335. N-(2-methylbutyl)-4(S)-{N-[2-(2-methoxyethoxy)ethoxycarbonyl]-3-(1-naphthyl)-L-alanyl-L-histidyl}amino-3(S)-hydroxy-6-methylheptanamide
336. N-[4(S)-{N-[2-(2-methoxyethoxy)ethoxycarbonyl]-3-(1-naphthyl)-L-alanylhistidyl}amino-3(S)-hydroxy-6-methylheptanoyl]-L-isoleucinol
337. N-(2-methylbutyl)-4(S)-{N-[2-(2-methoxyethoxy)ethoxycarbonyl]-3-(1-naphthyl)-L-alanyl-3-(1,3-thiazol-4-yl)-DL-alanyl}amino-3(S)-hydroxy-6-methylheptanamide
338. N-[4(S)-{N-[2-(2-methoxyethoxy)ethoxycarbonyl]-3-(1-naphthyl)-L-alanyl-3-(1,3-thiazol-4-yl)-DL-alanyl}amino-3(S)-hydroxy-6-methylheptanoyl]-L-isoleucinol
339. N-(2-methylbutyl)-4(S)-{N-[2-(2-methoxyethoxy)ethoxycarbonyl]-3-(1-naphthyl)-L-alanyl-L-norleucyl}amino-3(S)-hydroxy-6-methylheptanamide
340. N-[4(S)-{N-[2-(2-methoxyethoxy)ethoxycarbonyl]-3-(1-naphthyl)-L-alanyl-L-norleucyl}amino-3(S)-hydroxy-6-methylheptanoyl]-L-isoleucinol
341. N-(2-methylbutyl)-4(S)-{N-[2-(2-methoxyethoxy)ethoxycarbonyl]-3-(1-naphthyl)-L-alanyl-L-leucyl}amino-3(S)-hydroxy-6-methylheptanamide
342. N-[4(S)-{N-[2-(2-methoxyethoxy)ethoxycarbonyl]-3-(1-naphthyl)-L-alanyl-L-leucyl}amino-3(S)-hydroxy-6-methylheptanoyl]-L-isoleucinol
343. N-(2-methylbutyl)-4(S)-[N-(4-methoxybenzyloxycarbonyl)-3-(1-naphthyl)-L-alanyl-L-histidyl]amino-3(S)-hydroxy-6-methylheptanamide
344. N-{4(S)-[N-(4-methoxybenzyloxycarbonyl)-3-(1-naphthyl)-L-alanyl-L-histidyl]amino-3(S)-hydroxy-6-methylheptanoyl}-L-isoleucinol
345. N-(2-methylbutyl)-4(S)-[N-(4-methoxybenzyloxycarbonyl)-3-(1-naphthyl)-L-alanyl-3-(1,3-thiazol-4-yl)-DL-alanyl]amino-3(S)-hydroxy-6-methylheptanamide
346. N-{4(S)-[N-(4-methoxybenzyloxycarbonyl)-3-(1-naphthyl)-L-alanyl-3-(1,3-thiazol-4-yl)-DL-alanyl]amino-3(S)-hydroxy-6-methylheptanoyl]-L-isoleucinol
347. N-(2-methylbutyl)-4(S)-[N-(4-methoxybenzyloxycarbonyl)-3-(1-naphthyl)-L-alanyl-L-norleucyl]amino-3(S)-hydroxy-6-methylheptanamide
348. N-{4(S)-[N-(4-methoxybenzyloxycarbonyl)-3-(1-naphthyl)-L-alanyl-L-norleucyl]amino-3(S)-hydroxy-6-methylheptanoyl}-L-isoleucinol
349. N-(2-methylbutyl)-4(S)-[N-(4-methoxybenzyloxycarbonyl)-3-(1-naphthyl)-L-alanyl-L-leucyl]amino-3(S)-hydroxy-6-methylheptanamide
350. N-{4(S)-[N-(4-methoxybenzyloxycarbonyl)-3-(1-naphthyl)-L-alanyl-L-leucyl]amino-3(S)-hydroxy-6-methylheptanoyl}-L-isoleucinol
351. N-(2-methylbutyl)-4(S)-[N-(t-butoxycarbonyl)-3-(1-naphthyl)-L-alanyl-L-histidyl]amino-3(S)-hydroxy-6-methylheptanamide
352. N-{4(S)-[N-(t-butoxycarbonyl)-3-(1-naphthyl)-L-alanyl-L-histidyl]amino-3(S)-hydroxy-6-methylheptanoyl}-L-isoleucinol
353. N-(2-methylbutyl)-4(S)-[N-(t-butoxycarbonyl)-3-(1-naphthyl)-L-alanyl-3-(1,3-thiazol-4-yl)-DL-alanyl]amino-3(S)-hydroxy-6-methylheptanamide
354. N-{4(S)-[N-(t-butoxycarbonyl)-3-(1-naphthyl)-L-alanyl-3-(1,3-thiazol-4-yl)-DL-alanyl]amino-3(S)-hydroxy-6-methylheptanamido}-L-isoleucinol
355. N-(2-methylbutyl)-4(S)-[N-(t-butoxycarbonyl)-3-(1-naphthyl)-L-alanyl-L-norleucyl]amino-3(S)-hydroxy-6-methylheptanamide
356. N-{4(S)-[N-(t-butoxycarbonyl)-3-(1-naphthyl)-L-alanyl-L-norleucyl]amino-3(S)-hydroxy-6-methylheptanoyl}-L-isoleucinol
357. N-(2-methylbutyl)-4(S)-[N-(t-butoxycarbonyl)-3-(1-naphthyl)-L-alanyl-L-leucyl]amino-3(S)-hydroxy-6-methylheptanamide
358. N-{4(S)-[N-(t-butoxycarbonyl)-3-(1-naphthyl)-L-alanyl-L-leucyl]amino-3(S)-hydroxy-6-methylheptanoyl}-L-isoleucinol
359. N-(2-methylbutyl)-4(S)-[N-9-fluorenylmethoxycarbonyl-3-(1-naphthyl)-L-alanyl-L-histidyl]amino-3(S)-hydroxy-6-methylheptanamide
360. N-{4(S)-[N-9-fluorenylmethoxycarbonyl-3-(1-naphthyl)-L-alanyl-L-histidyl]amino-3(S)-hydroxy-6-methylheptanoyl}-L-isoleucinol
361. N-(2-methylbutyl)-4(S)-[N-9-fluorenylmethoxycarbonyl-3-(1-naphthyl)-L-alanyl-3-(1,3-thiazol-4-yl)-DL-alanyl]-amino-3(S)-hydroxy-6-methylheptanamide
362. N-{4(S)-[N-9-fluorenylmethoxycarbonyl-3-(1-naphthyl)-L-alanyl-3-(1,3-thiazol-4-yl)-DL-alanyl]amino-3(S)-hydroxy-6-methylheptanoyl}-L-isoleucinol
363. N-(2-methylbutyl)-4(S)-[N-9-fluorenylmethoxycarbonyl-3-(1-naphthyl)-L-alanyl-L-norleucyl]amino-3(S)-hydroxy-6-methylheptanamide 364. N-{4(S)-[N-9-fluorenylmethoxycarbonyl-3-(1-naphthyl)-L-alanyl-L-norleucyl]amino-3(S)-hydroxy-6-methylheptanoyl}-L-isoleucinol
365. N-(2-methylbutyl)-4(S)-[N-fluoren-9-ylmethoxycarbonyl-3-(1-naphthyl)-L-alanyl-L-leucyl]amino-3(S)-hydroxy-6-methylheptanamide
366. N-{4(S)-[N-fluoren-9-ylmethoxycarbonyl-3-(1-naphthyl)-L-alanyl-L-leucyl]amino-3(S)-hydroxy-6-methylheptanoyl}-L-isoleucinol
367. N-(2-methylbutyl)-4(S)-{N-[3-(3-nitropyrid-2-yldithio)propionyl]-3-(1-naphthyl)-L-alanyl-L-histidyl-}amino-3(S)-hydroxy-6-methylheptanamide
368. N-[4(S)-{N-[3-(3-nitropyrid-2-yldithio)propionyl]-3-(1-naphthyl)-L-alanyl-L-histidyl}amino-3(S)-hydroxy-6-methylheptanoyl]-L-isoleucinol
369. N-(2-methylbutyl)-4(S)-{N-[3-(3-nitropyrid-2-yldithio)propionyl]-3-(1-naphthyl)-L-alanyl-3-(1,3-thiazol-4-yl)-DL-alanyl}amino-3(S)-hydroxy-6-methylheptanamide
370. N-[4(S)-{N-[3-(3-nitropyrid-2-yldithio)propionyl]-3-(1-naphthyl)-L-alanyl-3-(1,3-thiazol-4-yl)-DL-alanyl}amino-3(S)-hydroxy-6-methylheptanoyl]-L-isoleucinol
371. N-(2-methylbutyl)-4(S)-{N-[3-(3-nitropyrid-2-yldithio)propionyl]-3-(1-naphthyl)-L-alanyl-L-norleucyl}amino-3(S)-hydroxy-6-methylheptanamide
372. N-[4(S)-{N-[3-(3-nitropyrid-2-yldithio)propionyl]-3-(1-naphthyl)-L-alanyl-L-norleucyl}amino-3(S)-hydroxy-6-methylheptanoyl]-L-isoleucinol
373. N-(2-methylbutyl)-4(S)-{N-[3-(3-nitropyrid-2-yldithio)propionyl]-3-(1-naphthyl)-L-alanyl-L-leucyl-}amino-3(S)-hydroxy-6-methylheptanamide
374. N-[4(S)-{N-[3-(3-nitropyrid-2-yldithio)propionyl]-3-(1-naphthyl)-L-alanyl-L-leucyl}amino-3(S)-hydroxy-6-methylheptanoyl]-L-isoleucinol
375. N-(2-methylbutyl)-4(S)-[N-(4-phenylbutyryl)-3-(1-naphthyl)-L-alanyl-L-histidyl]amino-3(S)-hydroxy-6-methylheptanamide
376. N-{4(S)-[N-(4-phenylbutyryl)-3-(1-naphthyl)-L-alanyl-L-histidyl]amino-3(S)-hydroxy-6-methylheptanoyl}-L-isoleucinol
377. N-(2-methylbutyl)-4(S)-[N-(4-phenylbutyryl)-3-(1-naphthyl)-L-alanyl-3-(1,3-thiazol-4-yl)-DL-alanyl-]amino-3(S)-hydroxy-6-methylheptanamide
378. N-{4(S)-[N-4-phenylbutyryl)-3-(1-naphthyl)-L-alanyl-3-(1,3-thiazol-4-yl)-DL-analyl]amino-3(S)-hydroxy-6-methylheptanoyl}-L-isoleucinol
379. N-(2-methylbutyl)-4(S)-[N-(4-phenylbutyryl)-3-(1-naphthyl)-L-alanyl-L-norleucyl]amino-3(S)-hydroxy-6-methylheptanamide
380. N-{4(S)-[N-(4-phenylbutyryl)-3-(1-naphthyl)-L-alanyl-L-norleucyl]amino-3(S)-hydroxy-6-methylheptanoyl}-L-isoleucinol
381. N-(2-methylbutyl)-4(S)-[N-(4-phenylbutyryl)-3-(1-naphthyl)-L-alanyl-L-leucyl}amino-3(S)-hydroxy-6-methylheptanamide
382. N-{4(S)-[N-(4-phenylbutyryl)-3-(1-naphthyl)-L-alanyl-L-leucyl]amino-3(S)-hydroxy-6-methylheptanoyl}-L-isoleucinol
383. N-(2-methylbutyl)-4(S)-[N-benzyloxycarbonyl-L-phenylalanyl-L-histidyl]amino-3(S)-hydroxy-6-methylheptanamide
384. N-{4(S)-[N-benzyloxycarbonyl-L-phenylalanyl-L-histidyl]amino-3(S)-hydroxy-6-methylheptanoyl}-L-isoleucinol
385. N-(2-methylbutyl)-4(S)-[N-benzyloxycarbonyl-L-phenylalanyl-3-(1,3-thiazol-4-yl)-DL-alanyl]amino-3(S)-hydroxy-6-methylheptanamide
386. N-{4(S)-[N-benzyloxycarbonyl-L-phenylalanyl-3-(1,3-thiazol-4-yl)-DL-alanyl]amino-3(S)-hydroxy-6-methylheptanoyl}-L-isoleucinol
387. N-(2-methylbutyl)-4(S)-(N-benzyloxycarbonyl-L-phenylalanyl-L-norleucyl)amino-3(S)-hydroxy-6-methylheptanamide
388. N-4(S)-(N-benzyloxycarbonyl-L-phenylalanyl-L-norleucyl)amino-3(S)-hydroxy-6-methylheptanoyl]-L-isoleucinol
389. N-(2-methylbutyl)-4(S)-(N-benzyloxycarbonyl-L-phenylalanyl-L-leucyl)amino-3(S)-hydroxy-6-methylheptanamide
390. N-[4(S)-(N-benzyloxycarbonyl-L-phenylalanyl-L-leucyl)amino-3(S)-hydroxy-6-methylheptanoyl]-L-isoleucinol
391. N-(2-methylbutyl)-4(S)-[N-benzyloxycarbonyl-3-(2,3,4,5,6-pentamethylphenyl)-L-alanyl-L-histidyl]amino-3(S)-hydroxy-6-methylheptanamide
392. N-{4(S)-[N-benzyloxycarbonyl-3-(2,3,4,5,6-pentamethylphenyl)-L-alanyl-L-histidyl]amino-3(S)-hydroxy-6-methylheptanoyl}-L-isoleucinol
393. N-(2-methylbutyl)-4(S)-[N-benzyloxycarbonyl-3-(2,3,4,5,6-pentamethylphenyl)-L-alanyl-3-(1,3-thiazol-4-yl)-DL-alanyl]amino-3(S)-hydroxy-6-methylheptanamide
394. N-{4(S)-[N-benzyloxycarbonyl-3-(2,3,4,5,6-pentamethylphenyl)-L-alanyl-3-(1,3-thiazol-4-yl)-DL-alanyl]amino-3(S)-hydroxy-6-methylheptanoyl}-L-isoleucinol
395. N-(2-methylbutyl)-4(S)-[N-benzyloxycarbonyl-3-(2,3,4,5,6-pentamethylphenyl)-L-alanyl-L-norleucyl]-amino-3(S)-hydroxy-6-methylheptanamide
396. N-{4(S)-[N-benzyloxycarbonyl-3-(2,3,4,5,6-pentamethylphenyl)-L-alanyl-L-norleucyl]amino-3(S)-hydroxy-6-methylheptanoyl}-L-isoleucinol
397. N-(2-methylbutyl)-4(S)-[N-benzyloxycarbonyl-3-(2,3,4,5,6-pentamethylphenyl)-L-alanyl-L-leucyl-]amino-3(S)-hydroxy-6-methylheptanamide
398. N-{4(S)-[N-benzyloxycarbonyl-3-(2,3,4,5,6-pentamethylphenyl)-L-alanyl-L-leucyl]amino-3(S)-hydroxy-6-methylheptanoyl}-L-isoleucinol
399. N-(2-methylbutyl)-4(S)-[N-benzyloxycarbonyl-L-tryptophyl-L-histidyl]amino-3(S)-hydroxy-6-methylheptanamide
400. N-{4(S)-[N-benzyloxycarbonyl-L-tryptophyl-L-histidyl]amino-3(S)-hydroxy-6-methylheptanoyl}-L-isoleucinol
401. N-(2-methylbutyl)-4(S)-[N-benzyloxycarbonyl-L-tryptophyl-3-(1,3-thiazol-4-yl)-DL-alanyl]amino-3(S)-hydroxy-6-methylheptanamide
402. N-{4(S)-[N-benzyloxycarbonyl-L-tryptophyl-3-(1,3-thiazol-4-yl)-DL-alanyl]amino-3(S)-hydroxy-6-methylheptanoyl}-L-isoleucinol
403. N-(2-methylbutyl)-4(S)-[N-benzyloxycarbonyl-L-tryptophyl-L-norleucyl]amino-3(S)-hydroxy-6-methylheptanamide
404. N-{4(S)-[N-benzyloxycarbonyl-L-tryptophyl-L-norleucyl]amino-3(S)-hydroxy-6-methylheptanoyl}-L-isoleucinol
405. N-(2-methylbutyl)-4(S)-[N-benzyloxycarbonyl-L-tryptophyl-L-leucyl]amino-3(S)-hydroxy-6-methylheptanamide
406. N-{4(S)-[N-benzyloxycarbonyl-L-tryptophyl-L-leucyl]amino-3(S)-hydroxy-6-methylheptanoyl}-L-isoleucinol
407. N-(2-methylbutyl)-4(S)-[N-benzyloxycarbonyl-3-(4-quinolyl)-L-alanyl-L-histidyl]amino-3(S)-hydroxy-6-methylheptanamide 408. N-{4(S)-[N-benzyloxycarbonyl-3-(4-quinolyl)-L-alanyl-L-histidyl]amino-3(S)-hydroxy-6-methylheptanoyl}-L-isoleucinol
409. N-(2-methylbutyl)-4(S)-[N-benzyloxycarbonyl-3-(4-quinolyl)-L-alanyl-3-(1,3-thiazol-4-yl)-DL-alanyl]amino-3(S)-hydroxy-6-methylheptanamide
410. N-{4(S)-[N-benzyloxycarbonyl-3-(4-quinolyl)-L-alanyl-3-(1,3-thiazol-4-yl)-DL-alanyl]amino-3(S)-hydroxy-6-methylheptanoyl}-L-isoleucinol
411. N-(2-methylbutyl)-4(S)-[N-benzyloxycarbonyl-3-(4-quinolyl)-L-alanyl-L-norleucyl]amino-3(S)-hydroxy-6-methylheptanamide
412. N-{4(S)-[N-benzyloxycarbonyl-3-(4-quinolyl)-L-alanyl-L-norleucyl]amino-3(S)-hydroxy-6-methylheptanoyl}-L-isoleucinol
413. N-(2-methylbutyl)-4(S)-[N-benzyloxycarbonyl-3-(4-quinolyl)-L-alanyl-L-leucyl]amino-3(S)-hydroxy-6-methylheptanamide
414. N-{4(S)-[N-benzyloxycarbonyl-3-(4-quinolyl)-L-alanyl-L-leucyl]amino-3(S)-hydroxy-6-methylheptanoyl}-L-isoleucinol
415. N-(2-methylbutyl)-4(S)-[N-benzyloxycarbonyl-3-(5-quinolyl)-L-alanyl-L-histidyl]amino-3(S)-hydroxy-6-methylheptanamide
416. N-{4(S)-[N-benzyloxycarbonyl-3-(5-quinolyl)-L-alanyl-L-histidyl]amino-3(S)-hydroxy-6-methylheptanoyl}-L-isoleucinol
417. N-(2-methylbutyl)-4(S)-[N-benzyloxycarbonyl-3-(5-quinolyl)-L-alanyl-3-(1,3-thiazol-4-yl)-DL-alanyl]amino-3(S)-hydroxy-6-methylheptanamide
418. N-{4(S)-[N-benzyloxycarbonyl-3-(5-quinolyl)-L-alanyl-3-(1,3-thiazol-4-yl)-DL-alanyl]amino-3(S)-hydroxy-6-methylheptanoyl}-L-isoleucinol
419. N-(2-methylbutyl)-4(S)-[N-benzyloxycarbonyl-3-(5-quinolyl)-L-alanyl-L-norleucyl]amino-3(S)-hydroxy-6-methylheptanamide
420. N-{4(S)-[N-benzyloxycarbonyl-3-(5-quinolyl)-L-alanyl-L-norleucyl]amino-3(S)-hydroxy-6-methylheptanoyl}-L-isoleucinol
421. N-(2-methylbutyl)-4(S)-[N-benzyloxycarbonyl-3-(5-quinolyl)-L-alanyl-L-leucyl]amino-3(S)-hydroxy-6-methylheptanamide
422. N-{4(S)-[N-benzyloxycarbonyl-3-(5-quinolyl)-L-alanyl-L-leucyl]amino-3(S)-hydroxy-6-methylheptanoyl}-L-isoleucinol
423. N-(2-methylbutyl)-4(S)-[N-benzyloxycarbonyl-3-(2-pyridyl)-L-alanyl-L-histidyl]amino-3(S)-hydroxy-6-methylheptanamide
424. N-{4(S)-[N-benzyloxycarbonyl-3-(2-pyridyl)-L-alanyl-L-histidyl]amino-3(S)-hydroxy-6-methylheptanoyl}-L-isoleucinol
425. N-(2-methylbutyl)-4(S)-[N-[benzyloxycarbonyl-3-(2-pyridyl)-L-alanyl-3-(1,3-thiazol-4-yl)-DL-alanyl]amino-3(S)-hydroxy-6-methylheptanamide
426. N-{4(S)-[N-benzyloxycarbonyl-3-(2-pyridyl)-L-alanyl-3-(1,3-thiazol-4-yl)-DL-alanyl]amino-3(S)-hydroxy-6-methylheptanoyl}-L-isoleucinol
427. N-(2-methylbutyl)-4(S)-[N-benzyloxycarbonyl-3-(2-pyridyl)-L-alanyl-L-norleucyl]amino-3(S)-hydroxy-6-methylheptanamide
428. N-{4(S)-[N-benzyloxycarbonyl-3-(2-pyridyl)-L-alanyl-L-norleucyl]amino-3(S)-hydroxy-6-methylheptanoyl}-L-isoleucinol
429. N-(2-methylbutyl)-4(S)-[N-benzyloxycarbonyl-3-(2-pyridyl)-L-alanyl-L-leucyl]amino-3(S)-hydroxy-6-methylheptanamide
430. N-{4(S)-[N-benzyloxycarbonyl-3-(2-pyridyl)-L-alanyl-L-leucyl]amino-3(S)-hydroxy-6-methylheptanoyl}-L-isoleucinol
431. N-(2-methylbutyl)-4(S)-[N-benzyloxycarbonyl-3-(3-pyridyl)-L-alanyl-L-histidyl]amino-3(S)-hydroxy-6-methylheptanamide
432. N-{4(S)-[N-benzyloxycarbonyl-3-(3-pyridyl)-L-alanyl-L-histidyl]amino-3(S)-hydroxy-6-methylheptanoyl}-L-isoleucinol
433. N-(2-methylbutyl)-4(S)-[N-benzyloxycarbonyl-3-(3-pyridyl)-L-alanyl-3-(1,3-thiazol-4-yl)-DL-alanyl]amino-3(S)-hydroxy-6-methylheptanamide
434. N-{4(S)-[N-benzyloxycarbonyl-3-(3-pyridyl)-L-alanyl-3-(1,3-thiazol-4-yl)-DL-alanyl]amino-3(S)-hydroxy-6-methylheptanoyl}-L-isoleucinol
435. N-(2-methylbutyl)-4(S)-[N-benzyloxycarbonyl-3-(3-pyridyl)-L-alanyl-L-norleucyl]amino-3(S)-hydroxy-6-methylheptanamide
436. N-{4(S)-[N-benzyloxycarbonyl-3-(3-pyridyl)-L-alanyl-L-norleucyl]amino-3(S)-hydroxy-6-methylheptanoyl}-L-isoleucinol
437. N-(2-methylbutyl)-4(S)-[N-benzyloxycarbonyl-3-(3-pyridyl)-L-alanyl-L-leucyl]amino-3(S)-hydroxy-6-methylheptanamide
438. N-{4(S)-[N-benzyloxycarbonyl-3-(3-pyridyl)-L-alanyl-L-leucyl]amino-3(S)-hydroxy-6-methylheptanoyl}-L-isoleucinol
439. N-(2-methylbutyl)-4(S)-[N-benzyloxycarbonyl-3-(4-pyridyl)-L-alanyl-L-histidyl]amino-3(S)-hydroxy-6-methylheptanamide
440. N-{4(S)-[N-benzyloxycarbonyl-3-(4-pyridyl)-L-alanyl-L-histidyl]amino-3(S)-hydroxy-6-methylheptanoyl}-L-isoleucinol
441. N-(2-methylbutyl)-4(S)-[N-benzyloxycarbonyl-3-(3-pyridyl)-L-alanyl-3-(1,3-thiazol-4-yl)-DL-alanyl]amino-3(S)-hydroxy-6-methylheptanamide
442. N-{4(S)-[N-benzyloxycarbonyl-3-(4-pyridyl)-L-alanyl-3-(1,3-thiazol-4-yl)-DL-alanyl]amino-3(S)-hydroxy-6-methylheptanoyl}-L-isoleucinol
443. N-(2-methylbutyl)-4(S)-[N-benzyloxycarbonyl-3-(4-pyridyl)-L-alanyl-L-norleucyl]amino-3(S)-hydroxy-6-methylheptanamide
444. N-{4(S)-[N-benzyloxycarbonyl-3-(4-pyridyl)-L-alanyl-L-norleucyl]amino-3(S)-hydroxy-6-methylheptanoyl}-L-isoleucinol
445. N-(2-methylbutyl)-4(S)-[N-benzyloxycarbonyl-3-(4-pyridyl)-L-alanyl-L-leucyl]amino-3(S)-hydroxy-6-methylheptanamide
446. N-{4(S)-[N-benzyloxycarbonyl-3-(4-pyridyl)-L-alanyl-L-leucyl]amino-3(S)-hydroxy-6-methylheptanoyl}-L-isoleucinol
447. N-{4(S)-[N-benzyloxycarbonyl-3-(4-nitrophenyl)-L-alanyl-L-histidyl]amino-3(S)-hydroxy-6-methylheptanoyl}-L-isoleucinol
448. 2-methylbutyl 4(S)-[N-benzyloxycarbonyl-3-(1-naphthyl)-L-alanyl-L-histidyl]amino-3(S)-hydroxy-6-methylheptanoate
449. N-{4(S)-[2(S)-N-benzyloxycarbonylamino-4-phenylbutyryl-L-histidyl]amino-3(S)-hydroxy-6-methylheptanoyl}-L-isoleucinol
450. N-{4(S)-[α-benzyloxycarbonyl-L-phenylglycyl)-L-histidyl]amino-3(S)-hydroxy-6-methylheptanoyl}-L-isoleucinol
451. N-[α-{1(S)-[2(S)-(N-benzyloxycarbonyl-3-(1-naphthyl)-L-alanyl)aminobut-3-enoyl]amino-3-methylbutylphosphinico}acetyl]-L-isoleucinol 452. N-isopropyl-4(S)-[N-benzyloxycarbonyl-3-(1-naphthyl)-L-alanyl-L-histidyl]amino-3(S)-hydroxy-6-methylheptanamide
453. N-sec-butyl-4(S)-[N-benzyloxycarbonyl-3-(1-naphthyl)-L-alanyl-L-histidyl]amino-3(S)-hydroxy-6-methylheptanamide
454. N-isobutyl-4(S)-[N-benzyloxycarbonyl-3-(1-naphthyl)-L-alanyl-L-histidyl]amino-3(S)-hydroxy-6-methylheptanamide
455. ethyl 5(S)-[N-benzyloxycarbonyl-3-(1-naphthyl)-L-alanyl-L-histidyl]amino-4(S)-hydroxy-7-methyloctanoate
456. ethyl 4(S)-[N-benzyloxycarbonyl-3-(1-naphthyl)-L-alanyl-L-histidyl]amino-6-methylheptanoate
457. 1-{4(S)-[N-benzyloxycarbonyl-3-(1-naphthyl)-L-alanyl-L-histidyl]amino-3(S)-hydroxy-6-methylheptanoyl}-L-leucinol
458. 2-[2-{4(S)-[N-benzyloxycarbonyl-3-(1-naphthyl)-L-alanyl-L-histidyl]amino-3(S)-hydroxy-6-methylheptanamido}ethyl]-1-methylpyrrolidine
459. 4(S)-[N-benzyloxycarbonyl-3-(1-naphthyl)-L-alanyl-L-histidyl]amino-3(S)-hydroxy-6-methyl-N-(2-morpholinoethyl)heptanamide
460. N-phenethyl-4(S)-[N-benzyloxycarbonyl-3-(1-naphthyl)-L-alanyl-L-histidyl]amino-3(S)-hydroxy-6-methylheptanamide
461. 4(S)-[N-benzyloxycarbonyl-3-(1-naphthyl)-L-alanyl-L-histidyl]amino-3(S)-hydroxy-6-methyl-N-[2-(2-pyridyl)ethyl]heptanamide
462. 4-[2-{4(S)-[N-benzyloxycarbonyl-3-(1-naphthyl)-L-alanyl-L-histidyl]amino-3(S)-hydroxy-6-methylheptanamido}ethyl]-1-benzylpiperidine
463. N-cyclohexyl-4(S)-[N-benzyloxycarbonyl-3-(1-naphthyl)-L-alanyl-L-histidyl]amino-3(S)-hydroxy-6-methylheptanamide
464. ethyl 4(S)-[N-benzyloxycarbonyl-3-(1-naphthyl)-L-alanyl-L-histidyl]amino-3(S)-mercapto-6-methylheptanoate
465. N-(2-methylbutyl)-4(S)-[N-benzyloxycarbonyl-3-(1-naphthyl)-L-alanyl-L-histidyl]amino-3(S)-mercapto-6-methylheptanamide
466. N-ethyl-N-(2-methylbutyl)-4(S)-[N-benzyloxycarbonyl-3-(1-naphthyl)-L-alanyl-L-histidyl]amino-3(S)-hydroxy-6-methylheptanamide
467. N-{4(S)-[N-benzyloxycarbonyl-3-(1-naphthyl)-L-alanyl-L-histidyl]amino-3(S)-mercapto-6-methylheptanoyl}-L-isoleucinol
468. N-(7,7-dimethylnorpinanylmethyl)-4(S)-[N-benzyloxycarbonyl-3-(1-naphthyl)-L-alanyl-L-histidyl]amino-3(S)-hydroxy-6-methylheptanamide
469. ethyl 6-{4(S)-[N-benzyloxycarbonyl-3-(1-naphthyl)-L-alanyl-L-histidyl]amino-3(S)-hydroxy-6-methylheptanamido}-2-t-butoxycarbonylaminohexanoate
470. ethyl 2-amino-6-{4(S)-[N-benzyloxycarbonyl-3-(1-naphthyl)-L-alanyl-L-histidyl]amino-3(S)-hydroxy-6-methylheptanamido}hexanoate
471. 2-{4(S)-[N-benzyloxycarbonyl-3-(1-naphthyl)-L-alanyl-L-histidyl]amino-3(S)-hydroxy-6-methylheptanamido}-3-benzyloxybutanol
472. 2-{4(S)-[N-benzyloxycarbonyl-3-(1-naphthyl)-L-alanyl-L-histidyl]amino-3(S)-hydroxy-6-methylheptanamido}butan-1,3-diol
473. ethyl 2-{4(S)-[N-benzyloxycarbonyl-3-(1-naphthyl)-L-alanyl-L-histidyl]amino-3(S)-hydroxy-6-methylheptanamido}-4-phenylbutyrate
474. N-(2,3-dihydroxypropyl)-4(S)-[N-benzyloxycarbonyl-3-(1-naphthyl)-L-alanyl-L-histidyl]amino-3(S)-hydroxy-6-methylheptanamide
475. 2-{4(S)-[N-benzyloxycarbonyl-3-(1-naphthyl)-L-alanyl-L-histidyl]amino-3(S)-hydroxy-6-methylheptanamido}-4-octadecen-1,3-diol
476. 1-{4(S)-[N-benzyloxycarbonyl-3-(1-naphthyl)-L-alanyl-L-histidyl]amino-3(S)-hydroxy-6-methylheptanoyl}-4-[3-(3,4,5-trimethoxyphenyl)propenoyl]piperazine
477. 1-{4(S)-[N-benzyloxycarbonyl-3-(1-naphthyl)-L-alanyl-L-histidyl]amino-3(S)-hydroxy-6-methylheptanoyl}-4-(3,4-methylenedioxybenzyl)piperazine
478. t-butyl 1-{4(S)-[N-benzyloxycarbonyl-3-(1-naphthyl)-L-alanyl-L-histidyl]amino-3(S)-hydroxy-6-methylheptanamido}pyrrolidine-2-carboxylate
479. N-(2-phenylpropyl)-4(S)-[N-benzyloxycarbonyl-3-(1-naphthyl)-L-alanyl-L-histidyl]amino-3(S)-hydroxy-6-methylheptanamide
480. N-cyclohexylmethyl-4(S)-[N-benzyloxycarbonyl-3-(1-naphthyl)-L-alanyl-L-histidyl]amino-3(S)-hydroxy-6-methylheptanamide
481. 1-{4(S)-[N-benzyloxycarbonyl-3-(1-naphthyl)-L-alanyl-L-histidyl]amino-3(S)-hydroxy-6-methylheptanoyl}-4-benzylpiperazine
482. 3-{4(S)-[N-benzyloxycarbonyl-3-(1-naphthyl)-L-alanyl-L-histidyl]amino-3(S)-hydroxy-6-methylheptanamido}-6-methylheptan-1,3-diol
483. N-(1-ethyl-2-pyrrolidinylmethyl)-4(S)-[N-benzyloxycarbonyl-3-(1-naphthyl)-L-alanyl-L-histidyl]amino-3(S)-hydroxy-6-methylheptanamide
484. α-{1(S)-[N-benzyloxycarbonyl-3-(1-naphthyl)-L-alanyl-L-histidyl]amino-3-methylbutylphosphinico}acetic acid
485. $N^1$-{4(S)-[N-benzyloxycarbonyl-3-(1-naphthyl)-L-alanyl-L-histidyl]amino-3(S)-hydroxy-6-methylheptanoyl}-$N^2$-(4-chlorobutyryl)hydrazine
486. N-(2-methylbutyl)-α-{1(S)-[N-benzyloxycarbonyl-3-(1-naphthyl)-L-alanyl-L-histidyl]amino-3-methylbutylphosphinico}acetamide
487. $N^1$-{4(S)-[N-benzyloxycarbonyl-3-(1-naphthyl)-L-alanyl-L-histidyl]amino-3(S)-hydroxy-6-methylheptanoyl}-$N^2$-sec-butylhydrazine
488. N-[α-{1(S)-[N-benzyloxycarbonyl-3-(1-naphthyl)-L-alanyl-L-histidyl]amino-3-methylbutylphosphinico}acetyl]-L-isoleucinol
489. N-[α-{1(S)-[N-benzyloxycarbonyl-3-(1-naphthyl)-L-alanyl-L-leucyl]amino-3-methylbutylphosphinico}acetyl]-L-isoleucinol
490. N-(2-methylbutyl)-4(S)-[N-benzyloxycarbonyl-3-(1-naphthyl)-L-alanyl-L-histidyl]amino-3(S)-hydroxy-5-methylheptanamide
491. N-{4(S)-[N-benzyloxycarbonyl-3-(1-naphthyl)-L-alanyl-L-histidyl]amino-3(S)-hydroxy-5-methylheptanoyl}-L-isoleucinol
492. $N^1$-{4(S)-[N-benzyloxycarbonyl-3-(1-naphthyl)-L-alanyl-L-histidyl]amino-3(S)-hydroxy-5-methylheptanoyl}-$N^2$-(4-chlorobutyryl)hydrazine
493. N-{4(S)-[2(S)-{N-[2-(2-methoxyethoxy)ethoxycarbonyl]-3-(1-naphthyl)-L-alanyl}aminoheptanoyl]amino-3(S)-hydroxy-6-methylheptanoyl}-L-isoleucinol
494. N-(2-methylbutyl)-4(S)-[2(S)-{N-[2-(2-methoxyethoxy)ethoxycarbonyl]-3-(1-naphthyl)-L-alanyl}aminoheptanoyl]amino-3(S)-hydroxy-6-methylheptanamide 495. methyl 3(S)-[N-benzyloxycarbonyl-3-(1-naphthyl)-L-alanyl-L-norleucyl]amino-2(S)-hydroxy-5-methylhexanoate 496. N-{4(S)-[2(S)-{N-[2-(2-methoxyethoxy)ethoxycarbonyl]-3-(1-naphthyl)-L-alanyl}aminopent-4-enoyl]amino-3(S)-hydroxy-6-methylheptanoyl}-L-isoleucinol 497. N-(2-methylbutyl)-4(S)-[2(S)-{N-[2-(2-methoxyethoxy)ethoxycarbonyl]-3-(1-naphthyl)-L-alanyl}aminopent-4-enoyl]amino-3(S)-hydroxy-6-methylheptanamide 498. N-{4(S)-[2(S)-{N-[2-(2-methoxyethoxy)ethoxycarbonyl]-3-(1-naphthyl)-L-alanyl}aminopent-4-ynoyl]amino-3(S)-hyroxy-6-methylheptanoyl}-L-isoleucinol 499. N-(2-methylbutyl)-4(S)-[2(S)-{N-[2-(2-methoxyethoxy)ethoxycarbonyl]-3-(1-naphthyl)-L-alanyl}aminopent-4-ynoyl]amino-3(S)-hydroxy-6-methylheptanamide 500. N-(2-methylbutyl)-4(S)-[3-(1-naphthyl)-L-alanyl-L-histidyl]amino-3(S)-hydroxy-6-methylheptanamide 501. N-{4(S)-[3-(1-naphthyl)-L-alanyl-L-histidyl]amino-3(S)-hydroxy-6-methylheptanoyl}-L-isoleucinol 502. N-(2-methylbutyl)-4(S)-[N-benzyloxycarbonyl-3-(2-naphthyl)-L-alanyl-L-histidyl]amino-3(S)-hydroxy-6-methylheptanamide 503. N-{4(S)-[N-benzyloxycarbonyl-3-(2-naphthyl)-L-alanyl-L-histidyl]amino-3(S)-hydroxy-6-methylheptanoyl}-L-isoleucinol 504. N-[α-{1(S)-[N-benzyloxycarbonyl-3-(1-naphthyl)-L-alanyl-3-(1,3-thiazol-4-yl)-DL-alanyl]amino-3-methylbutylphosphinico}acetyl]-L-isoleucinol 505. N-[α-{1(S)-[N-benzyloxycarbonyl-3-(1-naphthyl)-L-alanyl-3-(2-pyridyl)-DL-alanyl]amino-3-methylbutylphosphinico}acetyl]-L-isoleucinol Of the compounds listed above, the preferred compounds are Compounds No. 65, 66, 67, 192, 195, 196, 197, 200, 203, 206, 207, 208, 211, 216, 217, 218, 234, 237, 238, 239, 242, 258, 259, 285, 286, 287, 288, 289, 290, 293, 294, 297, 298, 303, 304, 305, 306, 309, 310, 311, 312, 313, 314, 315, 316, 325, 326, 327, 328–382 inclusive, 452, 453, 454, 457, 458, 459, 482, 483, 490–494 inclusive and 496–499 inclusive, more preferably Compounds No. 65, 66, 67, 207, 208, 218, 238, 239, 242, 259, 335, 453, 454, 457, 458, 482 and 483.

The compounds of the invention include pharmaceutically acceptable salts of the compounds of formula (I). Since the compounds of formula (I) contain basic nitrogen atoms and may, depending upon the nature of the group represented by X, also contain acidic groups, such salts may be acid addition salts or salts with bases. The nature of the salt is not critical, provided that it is pharmaceutically acceptable, and acids and bases which may be employed to form such salts are, of course, well known to those skilled in this art. Examples of acids which may be employed to form pharmaceutically acceptable acid addition salts include such inorganic acids as hydrochloric acid, sulfuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases, such as dicyclohexylamine. All of these salts may be prepared by conventional means from the corresponding compound of formula (I), for example simply by reacting the appropriate acid or base with the compound of formula (I).

The compounds of the present invention can be prepared by conventional processes.

For example, the compounds of the invention, especially alcohol products [in which the substituent Y in the desired compound (I) represents a hydroxy group], thioalcohol products [in which Y represents a mercapto group] or phosphonic acid products [in which X represents the group —P(O)(R$^5$)—OH], can be prepared by any conventional process used in peptide synthesis (for example, the azide process, the active ester process, the mixed acid anhydride process, the carbodiimide process or the condensation process using an oxidation-reduction system) by reacting a carboxylic acid having the general formula (II):

$$R^1CO—NH—CH(R^2)—COOH \quad (II)$$

(wherein R$^1$ and R$^2$ have the same meaning as above), or a reactive derivative thereof (such as a halide, anhydride, mixed anhydride, azide, active ester, active amide or carbodiimide), and an amino compound having the general formula (III):

$$H_2N—CH(R^3)—X'$$

[in which: X' represents a group of formula —P(O)-(OH)—R$^5$ or —CH(Y')—A-R$^4$, in which A, R$^4$ and R$^5$ are as defined above and Y' represents a hydroxy or mercapto group; and R$^3$ is as defined above, but is preferably an isobutyl or sec-butyl group].

Compounds of the invention can also be prepared by acyl exchange reactions involving any of the groups R$^1$CO—, NH$_2$CH(R$^2$)CO— or NH$_2$CH(R$^3$)CO—, most conveniently R$^1$CO— or NH$_2$CH(R$^3$)CO—, by conventional means or by other conventional transformation reactions, for example conversion of a carboxy or protected carboxy group included within the group represented by X to, for example, a carbamoyl, N-substituted carbamoyl, carbazoyl or N-substituted carbazoyl group.

INHIBITION OF RENIN ACTIVITY

The ability of various compounds of the invention to inhibit the activity of renin was determined according to the following method, which follows essentially the procedure of Kokubu et al. [Hypertension, 5, 191–197 (1983)].

Specifically, each test compound was dissolved in 60% v/v aqueous ethanol. Human renin activity in the presence and absence of each compound was measured using sheep angiotensinogen. The total volume of 1 ml of assay mixture contained 0.1 mole/liter phosphate buffer (pH 7.3), human renin (equivalent to 0.5 ng angiotensin I per ml per minute), sheep angiotensinogen (equivalent to 200 ng angiotensin I), the indicated concentration of the test compound, 6% ethanol and angiotensinase inhibitors (10 mmole/liter sodium ethylenediaminetetraacetate and 3.4 mmole/liter 8-hydroxyquinoline). The mixture was allowed to react for 10 minutes at 37° C., and then the reaction was stopped by placing the reaction tube in a boiling water bath for 5 minutes. The mixture was then centrifuged and the supernatant (0.05–0.1 ml) was used to assay remaining angiotensin I.

An identical experiment was carried out, as a control, except that the test compound was omitted. From the values obtained were calculated the % inhibition of renin activity achieved by each test compound. The results are shown in the following Table, in which the compounds of the invention are identified by the numbers assigned to them in the foregoing list. The values given are the mean of 3 or 4 experiments.

TABLE

| Compound No. | Concentration of test cpd. | % Inhibition (human renin) |
|---|---|---|
| 3 | $1 \times 10^{-5}$ M | 72 |
| 5 | $1 \times 10^{-5}$ M | 79 |
| 36 | $1 \times 10^{-5}$ M | 84 |
| 38 | $1 \times 10^{-5}$ M | 89 |
| 39 | $1 \times 10^{-5}$ M | 84 |
| 62 | $1 \times 10^{-5}$ M | 53 |
| 64 | $1 \times 10^{-5}$ M | 95 |
| 65 | $1 \times 10^{-5}$ M | 99 |
| 66 | $1 \times 10^{-5}$ M | 96 |
| 67 | $1 \times 10^{-5}$ M | 98 |
| 93 | $1 \times 10^{-5}$ M | 99 |
| 207 | $1 \times 10^{-6}$ M | 98.4 |
| 208 | $1 \times 10^{-6}$ M | 99.1 |
| 238 | $1 \times 10^{-6}$ M | 98.2 |

As can be seen from the above Table, the compounds of the invention have a substantial inhibitory effect on the activity of human renin and are thus useful for the diagnosis and therapy of renin/angiotensin-induced hypertension in humans and other animals.

The route of administration may be oral or parenteral and the compound of the invention may be formulated accordingly, normally with a pharmaceutically acceptable carrier or diluent as, for example, a tablet, capsule, granule, powder or syrup for oral administration or as an injection or suppository for parenteral administration. The dosage will vary depending upon the age, symptoms and body weight of the patient as well as upon the desired end result, but normally we would anticipate a dose of from 0.01 mg. to 100 mg. per Kg. body weight per day, which may be administered in a single dose or in divided doses.

The invention is further illustrated by the following non-limiting Examples. In the Examples, all of the values for specific rotation were measured using the sodium D line, i.e. all values are $[\alpha]_D$.

EXAMPLE 1

Ethyl 4(S)-[N-benzyloxycarbonyl-3-(1-naphthyl)-L-alanyl-L-histidyl]amino-3(S)-hydroxy-6-methylheptanoate (Compound No. 5)

(a)

250 mg (0.5 mmole) of N-benzyloxycarbonyl-3-(1-naphthyl)-L-alanyl-L-histidine hydrazide were dissolved in 8 ml of dimethylformamide, and 0.42 ml of 4.0N hydrogen chloride/dioxane were added to the solution, and the mixture was cooled to −60° C.

0.1 ml of isoamyl nitrite was added to the resulting solution, and then the reaction temperature was elevated to −20° C. The disappearance of the hydrazide was confirmed, and then the temperature of the mixture was again lowered to −60° C. The mixture was then neutralized by the addition of 0.17 g of N-methylmorpholine, to give a solution of N-benzyloxycarbonyl-3-(1-naphthyl)-L-alanyl-L-histidine azide.

(b)

Meanwhile, 5 ml of 6N hydrogen chloride/dioxane were added to 152 mg (0.5 mmole) of ethyl 4(S)-t-butoxycarbonylamino-3(S)-hydroxy-6-methylheptanoate. The solution was stirred for 20 minutes under a nitrogen stream, and then concentrated by evaporation under reduced pressure, to give a solid residue. The resulting residue was dissolved in 2 ml of dimethylformamide, and 0.05 g of N-methylmorpholine was added to give a solution of ethyl 4(S)-amino-3(S)-hydroxy-6-methylheptanoate.

(c)

To the cooled azide solution prepared as described in (a) above was added dropwise the ethyl ester solution prepared as described in (b) above. The mixture was stirred at 4° C. for 20 hours, and then the solvent was removed by distillation under reduced pressure. To the resulting residue was added a 5% w/v aqueous solution of sodium bicarbonate, and then the precipitated gum-like substance was extracted with ethyl acetate. The organic extract was washed with water and then with a saturated aqueous solution of sodium chloride. The solution was then dried over anhydrous sodium sulfate, and the solvent was removed by distillation under reduced pressure. A 1:5 by volume mixture of ethyl acetate and diethyl ether was added to the resulting residue to precipitate a solid, which was separated, finely pulverized and filtered to give 163 mg of the title compound as a white powder, melting at 138°–140° C., $[\alpha]^{24} -70.6°$ (C=0.5, methanol).

Elemental analysis: Calculated for $C_{37}H_{45}N_5O_7$: C, 66.15%; H, 6.75%; N, 10.43%. Found: C, 66.50%; H, 6.46%; N, 10.25%.

EXAMPLE 2

4(S)-[N-Benzyloxycarbonyl-3-(1-napthyl)-L-alanyl-L-histidyl]amino-3(S)-hydroxy-6-methylheptanoic acid (Compound No. 3)

112 mg (0.17 mmole) of ethyl 4(S)-[N-benzyloxycarbonyl-3-(1-naphthyl)-L-alanyl-L-histidyl]amino-3(S)-hydroxy-6-methylheptanoate (prepared as described in Example 1) were dissolved in 3 ml of methanol, and 0.2 ml (0.2 mmole) of a 1N aqueous solution of sodium hydroxide was added to the resulting solution. The mixture was then stirred at room temperature for 6 hours, after which it was neutralized by the addition of 1N aqueous hydrochloric acid. The solvent was then removed from the resulting solution by distillation under reduced pressure. To the solid residue were added 5 ml of water and 2 ml of ethyl acetate to form a precipitate, which was crushed and separated by filtration. The resulting residue was washed with water and with a small amount of ethyl acetate, and then dried to give 49 mg of the title compound as a white powder, melting at 191°–192° C., $[\alpha]^{24} -59.2°$ (C=0.3, methanol).

Elemental analysis: Calculated for $C_{35}H_{41}N_5O_7$: C, 65.94%; H, 6.30%, N 10.68%. Found: C, 66.21%; H, 6.03%; N, 10.51%.

EXAMPLE 3

Phenyl 4(S)-[N-benzyloxycarbonyl-3-(1-naphthyl)-L-alanyl-L-histidyl]amino-3(S)-hydroxy-6-methylheptanaoate (Compound No. 21)

(a) Phenyl 4(S)-t-butoxycarbonylamino-3(S)-hydroxy-6-methylheptanoate 371 mg of 2-fluoro-N-methylpyridine p-toluenesulfonate were dissolved in 1 ml of methylene chloride, and then 1 ml of a methylene chloride solution containing 300 mg of 4(S)-t-butoxycarbonylamino-3(S)-hydroxy-6-methylheptanoic acid, 103 mg of phenol and 484 mg of tributylamine was added under a nitrogen stream. The resulting solution was stirred at room temperature for 24 hours. It was then treated essentially as described in Example 1(b), and then separated by silica gel thin layer chromatography to give 144 mg of a colorless solid. Colorless prismatic crystals melting at 99°–100° C. were obtained by recrystallization from hexane.

Mass spectrum (m/e): 351 (M+). $[\alpha]_{24} -26.6°$ (C=0.5, methanol).

(b)

208 mg of N-benzyloxycarbonyl-3-(1-naphthyl)-L-alanyl-L-histidine were dissolved in 4 ml of dimethylformamide, and 0.31 ml of 4.0N hydrogen chloride/dioxane were added to the resulting solution which was then cooled to −60° C. 52 mg of isoamyl nitrite were then added to the resulting mixture, after which the reaction temperature was raised to −20° C. The disappearance of the hydrazide was confirmed, and then the temperature of the mixture was lowered to −60° C., and 126 mg of triethylamine were added to give an azide solution.

(c)

3 ml of 6N hydrogen chloride/dioxane were added under a nitrogen stream to 112 mg of phenyl 4(S)-t-butoxycarbonylamino-3(S)-hydroxy-6-methylheptanoate [prepared as desribed in (a) above]. The mixture was then stirred for 30 minutes, after which the solvent was removed by distillation under reduced pressure. The resulting residue was dissolved in 1 ml of dimethylformamide, and 64 mg of triethylamine were added to prepare a solution of phenyl 4(S)-amino-3(S)-hydroxy-6-methylheptanoate.

(d)

To the cool azide solution prepared as described in (b) above was added the phenyl ester solution prepared as described in (c) above. The mixture was stirred at 4° C. for 2 days and then the solvent was removed by distillation under reduced pressure. The resulting residue was treated in the same way as described in Example 1(c), and was then purified by silica gel column chromatography, eluted with a 20:1 by volume mixture of chloroform and methanol and triturated with diethyl ether, to afford 25 mg of the title compound as a colorless powder, melting at 103°–106° C., $[\alpha]_{24} -28.7°$ C. (C=0.3 methanol).

EXAMPLE 4

Benzyl 4(S)-[N-benzyloxycrbonyl-3-(1-naphthyl)-L-alanyl-L-histidyl]amino-3(S)-hydroxy-6-methylheptanoate (Compound No. 15)

(a) Benzyl 4(S)-t-butoxycarbonylamino-3(S)-hydroxy-6-methylheptanoate 275 mg of 4(S)-t-butoxycarbonylamino-3(S)-hydroxy-6-methylheptanoic acid and 181 mg of dicyclohexylamine were dissolved in 3 ml of dimethylformamide, and then 171 mg of benzyl bromide were added to the resulting solution, which was then stirred at room temperature for 24 hours. The resulting solution was then diluted with ethyl acetate, washed with a saturated aqueous solution of sodium chloride and dried over anhydrous sodium sulfate. The solvent was removed by distillation under reduced pressure, and the resulting residue was purified by silica gel thin layer chromatography, using a 4:1 by volume mixture of benzene and ethyl acetate as the developing solvent, to afford 220 mg of a colorless oily substance.

Mass spectrum (m/e): 366.2283 (M+1). $[\alpha]_{24} -27.1°$ (C=1, methanol).

(b) Benzyl 4(S)-[N-benzyloxycarbonyl-3-(1-naphthyl)-L-alanyl-L-histidyl]amino-3(S)-hydroxy-6-methylheptanoate The procedure described in Example 1(c) was repeated, but using 300 mg (0.6 mmole) of N-benzyloxycarbonyl-3-(1-naphthyl)-L-alanyl-L-histidine hydrazide and 180 mg of benzyl 4(S)-t-butoxycarbonylamino-3(S)-hydroxy-6-methylheptanoate. The resulting syrup was purified by silica gel column chromatography eluted with mixtures of chloroform and methanol ranging from 20:1 to 5:1. The solvent was removed by distillation under reduced pressure from the active fractions, and diethyl ether was added to the residue, to solidify it. This solid was finely pulverized and separated by filtration, giving 97 mg of the title compound as a white powdery solid, melting at 102°–109° C., $[\alpha]_{24} -31.0°$ (C=0.5 methanol).

Elemental analysis: Calculated for $C_{42}H_{47}N_5O_7$: C, 68.74%; H, 6.46%; N, 9.54%. Found: C, 68.50%; H, 6.72%; N, 9.26%.

EXAMPLE 5

4(S)-[N-Benzyloxycarbonyl-3-(1-naphthyl)-L-alanyl-L-histidyl]amino-3(S)-hydroxy-6-methylheptanoic acid hydrazide (Compound No. 38)

134 mg (0.2 mmole) of ethyl 4(S)-[N-benzyloxycarbonyl-3-(1-naphthyl)-L-alanyl-L-histidyl]amino-3(S)-hydroxy-6-methylheptanoate (prepared as described in Example 1) were dissolved in 2 ml of dimethylformamide, and 100 mg (2 mmole) of hydrazine hydrate were added to the resulting solution, which was then stirred at room temperature for 2 days. The solvent was then removed by distillation under reduced pressure, and water was added to the resulting residue to form a precipitate, which was filtered off. The resulting precipitate was washed thoroughly with water and then dissolved in methanol. The solvent was removed by distillation under reduced pressure. A 1:1 by volume mixture of diethyl acetate and diethyl ether was added to the resulting solid residue, which was then finely pulverized and filtered. There were obtained 112 mg of the title compound as a white powdery solid, melting at 120°–127° C., $[\alpha]_{24} -58.6°$. (C=0.5, dimethylformamide).

Elemental analysis: Calculated for $C_{35}H_{43}N_7O_6$: C, 63.91%; H, 6.59%; N, 14.91%. Found: C, 63.70%; H, 6.65%; N, 14.76%.

EXAMPLE 6

Methyl [1-{[N-benzyloxycarbonyl-3-(1-naphthyl)-L-alanyl-L-histidyl]amino}-3-methylbutylphosphinico]acetate (Compound No. 61)

(a) Methyl {1-(benzyloxycarbionylamino)-3-methylbutylphosphinico}acetate 100 ml of toluene were added to 2.1 g (0.0206 mole) of pivalic acid and 1.72 g (0.011 mole) of benzyl carbamate, and the mixture was stirred, whilst heating. A small amount of water was removed by distilling off about 20 ml of toluene. The remaining toluene solution was cooled to room temperature and 2 g of a powdery 0.4 nm molecular sieve was added under a nitrogen stream, and then 1.8 g (0.010 mole) of (carbomethoxymethyl)dichlorophosphine (prepared as described in EP publication No. 63,896) were added and the whole was stirred. To the resulting mixture was added 0.97 g (0.011 mole) of 3-methylbutyraldehyde dropwise over a period of 5 minutes. Generation of a little heat was observed. The mixture was stirred for 16 hours, and then filtered. The filtrate was concentrated by evaporation under reduced pressure. To the residual solution, were added 100 ml of water and the pH was adjusted to 8-9 by the addition of a saturated aqueous solution of sodium carbonate, and then the resulting solution was washed with diethyl ether. The pH value was adjusted to 1-2 with concentrated hydrochloric acid, and then the solution was extracted with ethyl acetate. The extract was washed with a saturated aqueous solution of sodium chloride and then dried over anhydrous magnesium sulfate. The ethyl acetate solution was concentrated by evaporation under reduced pressure, and the product was reprecipitated from a mixture of methylene chloride and hexane, and washed with a small amount of diethyl ether to afford 0.38 g of the title compound, melting at 133°–135° C.

Rf value=0.63 [thin layer chromatography, Silica gel; developing solvent: methanol/acetic acid/methylene chloride (1:1:8 by volume)].

Elemental analysis: Calculated for $C_{16}H_{24}NO_6P$: C, 53.78%; H, 6.77%; N, 3.92%; P, 8.67%. Found: C, 53.76%; H, 6.85%; N, 3.83%, P, 8.46%.

Mass spectrum (m/e): 357.36(M+).

(b)

Following the same procedure as described in Example 1, 100 mg (0.20 mmole) of N-benzyloxycarbonyl-3-(1-naphthyl)-L-alanyl-L-histidyl hydrazide were dissolved in 1 ml of dimethylformamide, and 0.2 ml of 4N hydrogen chloride/dioxane was added to make the solution acidic. 30 mg (0.26 mmole) of isoamyl nitrite were then added, whilst ice-cooling and stirring. The disappearance of the hydrazide was confirmed, and then triethylamine was added to make the resulting azide solution basic.

Meanwhile, the benzyloxycarbonyl group was removed from 70 mg (0.20 mmole) of the phosphinic acid compound synthesized as described in (a) above by catalytic hydrogenation using a 10% w/w palladium-on-carbon catalyst. The resulting compound was added to the azide solution, and the mixture was stirred at 4° C. for 4 days, keeping the solution basic. Water was added, and the mixture was extracted with ethyl acetate. The extract was washed with a saturated aqueous solution of sodium chloride, and then dried over anhydrous magnesium sulfate. The ethyl acetate solution was concentrated by distillation under reduced pressure, and the residue was isolated by reverse phase high performance chromatography (eluent: 90% v/v aqueous methanol). Reprecipitation from a mixture of methylene chloride and diethyl ether afforded 7 mg of the title compound as a white powder, melting at 141°–146° C., $[\alpha]^{24} - 3.0°$ (C=0.1, methanol).

Molecular formula and molecular weight $C_{35}H_{42}N_5O_8P_1 = 691.741$. FAB/MS Cation 692 (M+H)+. FAB/MS Anion 690 (M−H)−. (FAB/MS is Fast Atom Bombardment Mass Spectrometry).

According to the above data, the molecular weight was determined to be 691.

EXAMPLE 7

1-{4(S)-[N-Benzyloxycarbonyl-3-(1-naphthyl)-L-alanyl-L-histidyl]amino-3(S)-hydroxy-6-methylheptanoyl}-4-phenylpiperidine (Compound No. 36)

A mixture of 137 mg (0.5 mmole) of 4(S)-t-butoxycarbonylamino-3(S)-hydroxy-6-methylheptanoic acid, 117 mg (1 mmole) of 1-hydroxybenztriazole and 161 mg (1 mmole) of 4-phenylpiperidine was dissolved in 30 ml of methylene chloride.

To the resulting solution, were added 355 mg (2 mmole) of 1-ethyl-3-(3-dimethylaminopropyl)carbodiimide hydrochloride, and the resulting mixture was stirred at room temperature for 20 hours. The solvent was then distilled from the mixture. Ethyl acetate was added to the resulting residue, and the ethyl acetate layer was separated and washed with, in turn, a 5% w/v aqueous solution of sodium bicarbonate, water, a 5% w/v aqueous solution of citric acid and water, and dried over anhydrous sodium sulfate. Ethyl acetate was distilled from the extract under reduced pressure, to give 1-[4(S)-t-butoxycarbonylamino-3(S)-hydroxy-6-methylheptanoyl]-4-phenylpiperidine as an oil.

This substance showed an Rf value of 0.85 (developing solvent:chloroform/methanol=9:1 by volume) on thin layer chromatography using a silica gel plate. Its t-butoxycarbonyl radical was removed by the same procedure as described in Example 1(b), and the resulting compound was reacted in dimethylformamide at 5° C. for 24 hours with the azide prepared from N-benzyloxycarbonyl-3-(1-naphthyl)-L-alanyl-L-histidyl hydrazide (0.5 mmole). The dimethylformamide was then distilled off, and a 5% w/v aqueous solution of sodium bicarbonate was added to the resulting residue. The product was then extracted with ethyl acetate. The ethyl acetate layer was washed with, in turn, water, a 5% w/v aqueous solution of citric acid and water, and then dried over anhydrous sodium sulfate, after which it was concentrated by evaporation under reduced pressure.

When petroleum ether was added to the resulting residue, the desired product was precipitated. Further reprecipitation as carried out using a mixture of ethyl acetate and petroleum ether. The combined precipitates were collected by filtration and dried to give 82 mg of the title product, melting at 184°–187° C., $[\alpha]^{24} - 56.0°$ (C=0.1, methanol).

Elemental analysis: Calculated for $C_{46}H_{54}O_6N_6$: C, 70.20%; H, 6.92%; N, 10.68%. Found: C, 69.85%; H, 6.71%; N, 10.45%.

EXAMPLE 8

Methyl 3(S)-[N-benzyloxycarbonyl-3-(1-naphthyl)-L-alanyl-L-histidyl]amino-2(S)-hydroxy-5-methylhexanoate (Compound No. 62)

(a) Methyl 3(S)-t-butoxycarbonylamino-2(S)-hydroxy-5-methylhexanoate

A solution of 1.00 g (3.8 mmole) of 3(S)-t-butoxycarbonylamino-2-hydroxy-5-methylhexanoic acid prepared by the method of R. L. Johnson [J. Med. Chem., 25, 605 (1982)] in 30 ml, of methanol was stirred, whilst cooling with ice, and then a diethyl ether solution of diazomethane was added and the mixture was stirred at room temperature for 1 hour. The solvent was then distilled off and the resulting solid was recrystallized from hexane to give 952 mg of the title product as colorless needles, melting at 84°–85° C.; $[\alpha]^{25} -10.2°$ (C=1.26, methanol).

Elemental analysis: Calculated for $C_{13}H_{25}NO_5$: C, 56.71%; H, 9.15%; N, 5.08%. Found: C, 56.57%; H, 9.09%; N, 4.97%.

Nuclear Magntic Resonance Spectrum (CDCl$_3$) δ ppm: 0.91 (6H, doublet, J=7.5 Hz, CH$_3$×2); 1.45 (9H, singlet, t-butyl); 3.17 (1H, doublet, J=6 Hz, OH); 3.80 (3H, singlet, OCH$_3$); 3.90–4.27 (1H, multiplet, NHCH); 4.35 (1H, doublet of doublets, J=3 & 6 Hz, CHCO$_2$CH$_3$); 4.53–4.96 (1H, multiplet, NH).

Mass spectrum (m/e): 275 (M+).

Infrared Absorption Spectrum (Nujol-trade mark-mull) $\nu_{max}$ cm$^{-1}$: 3375 (OH), 1740 (CO of ester).

(b)

The procedure described in Example 1 was repeated, but using 95 mg (0.19 mmole) of N-benzyloxycarbonyl-3-(1-naphthyl)-L-alanyl-L-histidine hydrazide and 52 mg (0.19 mmole) of methyl 3(S)-t-butoxycarbonylamino-2(S)-hydroxy-5-methylhexanoate.

There were obtained 84 mg of the title product as a white powdery solid, melting at 110°–114° C.; $[\alpha]^{24} -53.2°$ (C=0.5, methanol).

Elemental analysis: Calculated for $C_{35}H_{41}N_5O_7$: C, 65.20%; H, 6.42%; N, 10.88%. Found: C, 64.92%; H, 6.54%; N, 10.60%.

EXAMPLE 9

1-{4(S)-[N-Benzyloxycarbonyl-3-(1-naphthyl)-L-alanyl-L-histidyl]amino-3(S)-hydroxy-6-methylheptanamido}-4-(3-trifluoromethylphenyl)piperazine (Compound No. 63)

The procedure described in Example 7 was repeated, but using 230 mg (1 mmole) of 4-(3-trifluoromethylphenyl)piperazine, to afford 1-[-4(S)-t-butoxycarbonylamino-3(S)-hydroxy-6-methylheptanamido]-4-(3-trifluoromethylphenyl)piperazine as a solid melting at 107°–109° C. Its t-butoxycarbonyl radical was removed by the same procedure as described in Example 1(b), and the procedure described in Example 7 was repeated but using the azide prepared from 250 mg (0.5 mmole) of N-benzyloxycarbonyl-3-(1-naphthyl)-L-alanyl-L-histidyl hydrazide to give 188 mg of the title compound as a white powdery solid, melting at 179°–181° C., $[\alpha]^{24} -30.0°$ (C=0.5, methanol).

Elemental analysis: Calculated for $C_{46}H_{52}N_7O_6F_3$: C, 65.62%; H, 6.23%; N, 11.40%. Found: C, 65.35%; H, 6.51%; N, 11.24%.

EXAMPLE 10

4(S)-[N-Benzyloxycarbonyl-3-(1-naphthyl)-L-alanyl-L-histidyl]amino-N-butyl-3(S)-hydroxy-6-methylheptanamide (Compound No. 64)

The procedure described in Example 7 was repeated but using 73 mg (1 mmole) of butylamine to afford 4(S)-t-butoxycarbonylamino-N-butyl-3(S)-hydroxy-6-methylheptanamide as an oily substance. This substance showed an Rf value of 0.72 (developing solvent: chloroform/methanol=9:1 by volume) on thin layer chromatography. Its t-butoxycarbonyl radical was removed by the same procedure as described in Example 1(b), and then the same procedure as described in Example 7 was repeated, but using the azide prepared from 250 mg of (0.5 mmole) of N-benzyloxycarbonyl-3-(1-naphthyl)-L-alanyl-L-histidyl hydrazide, to give 75 mg of the title compound as a white powdery solid melting at 169°–171° C., $[\alpha]^{22} -18.0°$ (C=0.5, methanol).

Elemental analysis: Calculated for $C_{39}H_{50}N_6O_6$: C, 67.02%; H, 7.21%; N, 12.03%. Found: C, 66.87%; H, 7.50%; N, 11.89%.

EXAMPLE 11

4(S)-[N-Benzyloxycarbonyl-3-(1-naphthyl)-L-alanyl-L-histidyl]amino-3(S)-hydroxy-6-methyl-N-[S-(−)-2-methylbutyl]heptanamide (Compound No. 65)

The procedure described in Example 7 was repeated, but using 87 mg (1 mmole) of (S)-(−)-2-methylbutylamine to afford 4(S)-t-butoxycarbonyl-3(S)-hydroxy-6-methyl-N-[(S)-(−)-2-methylbutyl]heptanamide as a solid melting at 83°–84° C. Its t-butoxycarbonyl group was removed by the same procedure as described in Example 1(b), and then the procedure described in Example 7 was repeated, but using the azide prepared from 250 mg (0.5 mmole) of N-benzyloxycarbonyl-3-(1-naphthyl)-L-alanyl-L-histidyl hydrazide to give 180 mg of the title compound as a white powdery solid melting at 164°–166° C., $[\alpha]^{22} -6.8°$ (C=0.5, methanol).

Elemental analysis: Calculated for $C_{40}H_{52}N_6O_6$: C, 67.39%; H, 7.35%; N, 11.79%. Found: C, 67.10%; H, 7.61%; N, 11.52%.

EXAMPLE 12

4(S)-[N-Benzyloxycarbonyl-3-(1-naphthyl)-L-alanyl-L-histidyl]amino-N-ethyl-3(S)-hydroxy-6-methylheptanamide (Compound No. 66)

(a)

4(S)-t-Butoxycarbonylamino-N-ethyl-3(S)-hydroxy-6-methylheptanamide 275 mg (1 mmole) of 4(S)-t-butoxycarbonylamino-3(S)-hydroxy-6-methylheptanoic acid and 197 mg (1.1 mmole) of N-hydroxy-5-norbornene-2,3-dicarboximide were dissolved in 10 ml of methylene chloride and ice-cooled. To this solution were added 227 mg (1.1 mmole) of dicyclohexylcarbodiimide, and the mixture was stirred for 1 hour whilst ice-cooling and for a further 2 hours at room temperature. 90 mg (1.1 mmole) of ethylamine hydrochloride and 111 mg (1.1 mmole) of N-methylmorpholine were then added and the reaction mixture was stirred overnight at room temperature. The precipitated dicyclohexylurea was removed by filtration, and the filtrate was concentrated by evaporation under reduced pressure. A 10% w/v aqueous solution of citric acid was added to the resulting residue, and the precipitated oily substance was extracted with ethyl acetate. The organic extract was washed with, in turn, a 10% w/v aqueous solution of citric acid, water, a 5% w/v aqueous solution of sodium bicarbonate and a saturated aqueous solution of sodium chloride, dried over anhydrous sodium sulfate and concentrated by evaporation under reduced pressure. Diethyl ether was added to the oily residue to remove insoluble matter, and the filtrate was concentrated by evaporation under reduced pressure. Hexane was added to the resulting oily residue, to solidify it, and the solid was reprecipitated from a 2:1 by volume mixture of hexane and diethyl ether and filtered to give the title compound as a white powdery solid melting at 103°–107° C., $[\alpha]^{23} -43.6°$ (C=0.5, methanol).

Elemental analysis: Calculated for $C_{15}H_{30}N_2O_4$: C, 59.57%; H, 10.00%; N, 9.26%. Found: C, 59.40%; H, 9.89%; N, 9.41%.

(b) Compound No. 66

The t-butyloxycarbonyl group was removed from the compound produced as described in (a) above by the same procedure as described in Example 1(b), and then the procedure described in Example 7 was repeated but using the azide prepared from 250 mg (0.5 mmole) of N-benzyloxycarbonyl-3-(1-naphthyl)-L-alanyl-L-histidyl hydrazide to give 290 mg of the title compound as a white powdery solid melting at 184°–186° C., $[\alpha]^{27} -60.2°$ (C=0.5, methanol).

Elemental analysis: Calculated for $C_{37}H_{46}N_6O_6$: C, 66.25%; H, 6.91%; N, 12.53%. Found: C, 65.85%; H, 6.63%; N, 12.40%.

EXAMPLE 13

$N^1$-{4(S)-[N-benzyloxycarbonyl-3-(1-naphthyl)-L-alanyl-L-histidyl]amino-3(S)-hydroxy-6-methylheptanoyl}-$N^2$-(4-benzoylbutyryl)hydrazine (Compound No. 40)

66 mg (0.1 mmole) of 4(S)-[N-benzyloxycarbonyl-3-(1-naphthyl)-L-alanyl-L-histidyl]amino-3(S)-hydroxy-6-methylheptanoic acid hydrazide (prepared as described in Example 5) were dissolved in 3 ml of dimethylformamide, and then 31 mg (0.1 mmole) of N-hydroxysuccinimide 4-benzoylbutyrate were added and the mixture was stirred for 2 days at room temperature. The resulting reaction mixture was concentrated by evaporation under reduced pressure, and water was added to the resulting residue. After the water had been added to the residue, the precipitate was separated by filtration. It was washed with water, and the powder obtained after drying was washed with ethyl acetate, to give 63 mg of the title compound as a white powdery solid melting at 158°–160°, $[\alpha]^{27} -44.4°$ (C=0.5, methanol).

Elemental analysis: Calculated for $C_{46}H_{53}N_7O_8$: C, 66.41%; H, 6.42%; N, 11.78%. Found: C, 66.18%; H, 6.59%; N, 11.65%.

EXAMPLE 14

N-{4(S)-[N-Benzyloxycarbonyl-3-(1-naphthyl)-L-alanyl-L-histidyl]amino-3(S)-hydroxy-6-methylheptanoyl}-L-isoleucinol (Compound No. 67)

(a)
N-[4(S)-t-Butoxycarbonylamino-3(S)-hydroxy-6-methylheptanoyl]-L-isoleucinol

The procedure described in Example 12(a) was repeated but using 129 mg (1.1 mmole) of L-isoleucinol to afford 330 mg of the title compound as a white powdery solid melting at 91°–96° C., $[\alpha]^{23} -46.6°$ (C=0.5, methanol).

Elemental analysis: Calculated for $C_{19}H_{38}N_2O_5$: C, 60.93%; H, 10.23%; N, 7.48%. Found: C, 60.95%; H, 10.18%; N, 7.53%.

(b) Compound No. 67

The procedure described in Example 7 was repeated but using 0.19 g (0.5 mmole) of the compound prepared as described in (a) above to give 112 mg of the title compound as a white powdery solid melting at 168°–171° C., $[\alpha]^{23} -48.8°$ (C=0.5 methanol).

Elemental analysis: Calculated for $C_{41}H_{54}N_6O_7$: C, 66.28%; H, 7.33%; N, 11.31%. Found: C, 65.99%; H, 7.61%; N, 11.14%.

EXAMPLE 15

4(S)-[N-Benzyloxycarbonyl-3-(1-naphthyl)-L-alanyl-D-histidyl]amino-3(S)-hydroxy-6-methyl-N-[S-(−)-2-methylbutyl]heptanamide (Compound No. 93)

(a)
4(S)-(N-Benzyloxycarbonyl-D-histidyl)amino-3(S)-hydroxy-6-methyl-N-[S-(−)-2-methylbutyl]heptanamide 2.00 g (22.9 mole) of S-(−)-2-methylbutylamine and 6.00 g (21.8 mmole) of 4(S)-t-butoxycarbonylamino-3(S)-hydroxy-6-methylheptanoic acid were dissolved in 50 ml of anhydrous tetrahydrofuran, and 4.3 g of diethyl phosphorocyanidate (26.4 mmole) and 3.7 ml (26.5 mmole) of triethylamine were added dropwise to the solution under a nitrogen atmosphere. The mixture was stirred for 2 hours at room temperature. The reaction product was then condensed by evaporation under reduced pressure, and ethyl acetate was added to the residue. The mixture was washed with 10% w/v aqueous hydrochloric acid, a saturated solution of sodium bicarbonate, and a saturated solution of sodium chloride, in that order, and then dried over anhydrous magnesium sulfate. The dried mixture was condensed by evaporation under reduced pressure, and the residue was purified by silica gel column chromatography eluted with a 10:1 by volume mixture of chloroform and methanol to yield 5.1 g (68%) of the title compound.

The t-butoxycarbonyl group was removed from this compound using a mixture of 6N hydrochloric acid and dioxane as described in Example 1(b), to give 4(S)-amino-3(S)-hydroxy-6-methyl-N-[S-(−)-2-methylbutyl]heptanamide hydrochloride.

Meanwhile, 1.00 g (3.30 mmole) of N-benzyloxycarbonyl-D-histidine hydrazide was suspended in 20 ml of dimethylformamide, and 2.8 ml of a mixture of 4N hydrochloric acid and dioxane was added to the suspension, whilst cooling at −60° C. After completion of this addition, the reaction temperature was raised to −20° C., and 0.53 ml (3.95 mmole) of isoamyl nitrite was added to the mixture; the mixture was then stirred for 10 minutes. Disappearance of the hydrazide was confirmed, and then the mixture was cooled down to −60° C., after which 1.37 ml (12.5 mmole) of N-methylmorpholine was added for neutralization. 1.00 g (3.56 mmole) of 4(S)-amino-3(S)-hydroxy-6-methyl-N-[S-(−)-2-methylbutyl]heptanamide hydrochloride [prepared as described in (a) above] and 0.4 ml (3.64 mmole) of N-methylmorpholine were then added to the mixture, which was further stirred overnight at 4° C. The solvent was then distilled off under reduced pressure, and the residue was purified by silica gel column chromatography eluted with a 20:1 by volume mixture of chloroform and methanol, to yield 850 mg (48%) of white crystals of the monohydrate of the title compound melting at 77°–79° C., $[\alpha]^{25} = -26.4$ (C=0.5, methanol).

Elemental analysis: Calculated for $C_{27}H_{43}N_5O_6$: C, 60.77%; H, 8.12%; N, 13.12%. Found: C, 60.75%; H, 8.12%; N, 13.40%.

(b) Compound No. 93

700 mg (1.31 mmole) of the monohydrate of 4(S)-[N-benzyloxycarbonyl-D-histidyl]amino-3(S)-hydroxy-6-methyl-N-[S-(−)-2-methylbutyl]heptanamide were dissolved in 20 ml of ethanol, and 2.62 ml of 1N hydrochloric acid and 70 mg of 10% w/v palladium-on-carbon were added to the solution, which was then stirred for 4 hours at room temperature in a hydrogen atmosphere to remove the benzyloxycarbonyl group. The solvent was then distilled off under reduced pressure. 20 ml of anhydrous tetrahydrofuran were added to the residue, and 400 mg (1.14 mmole) of N-benzyloxycarbonyl-3-(1-naphthyl)-L-alanine were also dissolved in the mixture. 0.2 ml (1.32 mmole) of diethyl phosphorocyanidate and 0.6 ml (4.30 mmole) of triethylamine were then added dropwise, with ice cooling, under a nitrogen atmosphere, and the mixture was stirred for 6 hours at room temperature. The reaction product was condensed by evaporation under reduced pressure, and ethyl acetate was added to the residue. The mixture was washed with water and dried over anhydrous magnesium sulfate. The dried product was condensed by evaporation under reduced pressure, and the residue was purified by silica gel preparative thin layer chromatography, using a 5:1 by volume mixture of chloroform and methanol as developing solvent, to yield 450 mg (54%) of white crystals of the monohydrate of the title compound melting at 108°–110° C., $[\alpha]^{25} = -22.0°$ (C=0.5, methanol).

Elemental analysis: Calculated for $C_{40}H_{54}N_6O_7$: C, 65.73%; H, 7.45%; N, 11.49%. Found: C, 65.56%; H, 7.32%; N, 11.20%.

EXAMPLE 16

4(S)-[N-Benzyloxycarbonyl-3-(1-naphthyl)-L-alanyl-L-leucyl]amino-3(S)-hydroxy-6-methyl-N-[S-(−)-2-methylbutyl]heptanamide (Compound No. 207)

(a)

4(S)-[N-benzyloxycarbonyl-L-leucyl]amino-3(S)-hydroxy-6-methyl-N-[S-(−)-2-methylbutyl]heptanamide 280 mg (1 mmole) of 4(S)-amino-3(S)-hydroxy-6-methyl-N-[S-(−)-2-methylbutyl]heptanamide hydrochloride were dissolved in 5 ml of methylene chloride, and 111 mg (1.1 mmole) of N-methylmorpholine were added to the solution, whilst ice cooling, to neutralize it. 398 mg (1.1 mmole) of N-benzyloxycarbonyl-L-leucine N-hydroxysuccinimide ester were then added, and the mixture was stirred overnight at room temperature. 0.5 ml of N,N′-dimethylaminopropylamine was then added, and the mixture was stirred for 1 hour at room temperature to allow the amine to react with any excess of active ester. The reaction product was then condensed by evaporation under reduced pressure, and 1N hydrochloric acid was added to the residue. The oily substance isolated by this addition was extracted with ethyl acetate. The organic extract was washed with water, with a 5% w/v aqueous solution of sodium bicarbonate, and with a saturated aqueous solution of sodium chloride, and was then condensed by evaporation under reduced pressure. The resulting solid residue was then purified by silica gel column chromatography eluted with mixtures of benzene and ethyl acetate ranging from 4:1 to 2:1 by volume. The fraction containing the desired compound was collected and condensed by evaporation under reduced pressure. Diethyl ether was added with thorough grinding to the condensate, and then the precipitate was collected by filtration to yield 297 mg of the title compound as a colorless powder melting at 146°–149° C.

Elemental analysis: Calculated for $C_{27}H_{45}N_3O_5$: C, 65.95%; H, 9.23%; N, 8.55%. Found: C, 65.88%; H, 9.30%; N, 8.66%.

(b) Compound No. 207

The benzyloxycarbonyl group was removed from 246 mg (0.5 mmole) of the compound prepared as described in (a) above by catalytic hydrogenation using 5% w/v palladium-on-carbon as a catalyst according to the method described in Example 15(b), giving L-leucyl-4(S)-amino-3(S)-hydroxy-6-methyl-N-[S-(−)-2-methylbutyl]heptanamide hydrochloride. This was then dissolved in 2 ml of dimethylformamide, neutralized with 55 mg (0.5 mmole) of N-methylmorpholine, and stirred at 0° C. for 2.5 hours.

Meanwhile, 175 mg (0.5 mmole) of N-benzyloxycarbonyl-3-(1-naphthyl)-L-alanine and 61 mg (0.6 mmole) of N-methylmorpholine were dissolved in 10 ml of anhydrous tetrahydrofuran, and the solution was cooled down to −5° C. Whilst cooling, 65 mg (0.6 mmole) of ethyl chlorocarbonate was added dropwise to the solution, which was then stirred for 15 minutes.

The above-mentioned solution of L-leucyl-4(S)-amino-3(S)-hydroxy-6-methyl-N-[S-(−)-2-methylbutyl]heptanamide hydrochloride was then added and the mixture was left standing overnight at room temperature. The product was then condensed by evaporation under reduced pressure. Water was added to the residue, and the resulting precipitate was collected by filtration. The precipitate was thoroughly washed on the glass filter with a 1:1 by volume mixture of diethyl ether and ethyl acetate and then collected thereon by filtration, to yield 265 mg of the title compound as a colorless powder melting at 226°–229° C., $[\alpha]^{23} - 69.7°$ (C=0.3, dimethylformamide).

Elemental analysis: Calculated for $C_{40}H_{56}N_4O_6 \cdot \frac{1}{2} H_2O$: C, 68.84%; H, 8.23%; N, 8.03%. Found: C, 68.83%; H, 8.19%; N, 8.22%.

EXAMPLE 17

N-{4(S)-[N-Benzyloxycarbonyl-3-(1-naphthyl)-L-alanyl-L-leucyl]amino-3(S)-hydroxy-6-methylheptanoyl}-L-isoleucinol (Compound No. 208)

(a)

N-Benzyloxycarbonyl-3-(1-naphthyl)-L-alanyl-L-leucine hydrazide 3.49 g (10 mmole) of N-benzyloxycarbonyl-3-(1-naphthyl)-L-alanine and 1.21 g (12 mmole) of N-methylmorpholine were dissolved in 30 ml of anhydrous tetrahydrofuran, and then, whilst cooling the solution at −5° C., 1.30 g (12 mmole) of ethyl chlorocarbonate was added dropwise, with stirring, over a period of 15 minutes. 2.35 g (12 mmole) of L-leucine ethyl ester hydrochloride [which had been suspended in 10 ml of methylene chloride and neutralized with 1.21 g (12 mmole) of N-methylmorpholine] were added. The mixture was stirred for 2 hours with ice cooling, and then left standing overnight at room temperature. It was then condensed by evaporation under reduced pressure. Water was added to the residue, and the precipitating oily substance was extracted with ethyl acetate. The organic extract was washed with 1N hydrochloric acid, water, a 5% w/v aqueous solution of sodium bicarbonate and a saturated aqueous solution of sodium chloride, in that order, and then dried over anhydrous sodium sulfate. The solvent was distilled off under reduced pressure. The N-benzyloxycarbonyl-3-(1-naphthyl)-L-alanyl-L-leucine ethyl ester thus obtained in a syrupy form was dissolved in 30 ml of dimethylformamide, and 5.06 g (100 mmole) of hydrazine hydrate were added to the solution. The mixture was stirred for 36 hours at room temperature. The reaction product was then condensed by evaporation under reduced pressure, and water was added to the residue. The colorless crystals produced were collected by filtration, thoroughly washed with water and dried in a desiccator to yield 4.23 g of the title compound melting at 200°-204° C.

Elemental analysis: Calculated for $C_{27}H_{32}N_4O_4$: C, 68.04%; H, 6.77%; N, 11.76%. Found: C, 68.32%; H, 6.73%; N, 11.90%.

(b) N-{4(S)-[N-Benzyloxycarbonyl-3-(1-naphthyl)-L-alanyl-L-leucyl]amino-3(S)-hydroxy-6-methylheptanoyl}-L-isoleucinol 477 mg (1 mmole) of the hydrazide produced as described in step (a) above were dissolved in 8 ml of dimethylformamide, and the solution was cooled to −60° C. 0.84 ml of 4.0N hydrogen chloride in dioxane and 0.18 ml of isoamyl nitrite were added. The reaction temperature was then raised to −20° C. with stirring for 10 minutes. Disappearance of the hydrazide was confirmed, and then the temperature of the product was lowered again to −60° C. 0.45 g of N-methylmorpholine was added to neutralize the solution and yield a solution of N-benzyloxycarbonyl-3-(1-naphthyl)-L-alanyl-L-leucine hydrazide.

Meanwhile, the t-butoxycarbonyl group was removed from 412 mg (1.1 mmole) of 4(S)-t-butoxycarbonylamino-3(S)-hydroxy-6-methylheptanoyl-L-isoleucinol with 6N hydrogen chloride in dioxane, as described in Example 1(b), to yield 4(S)-amino-3(S)-hydroxy-6-methylheptanoyl-L-isoleucinol hydrochloride. This product was dissolved in 5 ml of dimethylformamide, and the resulting solution was added to the above-mentioned hydrazide solution, and the mixture was stirred at 4° C. for 7 days. The solvent was distilled off under reduced pressure. Water was added to the residue, and the oily substance produced was extracted with ethyl acetate. The organic extract was washed with 1N hydrochloric acid, water, a 5% w/v aqueous solution of sodium bicarbonate and a saturated aqueous solution of sodium chloride, in that order, and dried over anhydrous sodium sulfate. It was then condensed by evaporation under reduced pressure. The syrupy residue was purified by silica gel preparative thin layer chromatography, using a 5:1 by volume mixture of chloroform and methanol as the developing solvent. The active fractions extracted with ethyl acetate. The extract was washed with water and with a saturated aqueous solution of sodium chloride, dried, and then condensed by evaporation under reduced pressure. On adding diethyl ether to the residues, the condensate solidified, and this was finely ground and then collected by filtration to yield 402 mg of the title compound as a colorless powder melting at 206°-212° C., $[\alpha]^{23}-95.0°$ (C=0.3, methanol).

Elemental analysis: Calculated for $C_{41}H_{58}N_4O_7$: C, 68.49%; H, 8.13%; N, 7.29%. Found: C, 68.46%; H, 7.94%; N, 7.87%.

EXAMPLE 18

N-{4(S)-[N-Benzyloxycarbonyl-3-(1-naphthyl)-L-alanyl-3-(2-thienyl)-DL-alanyl]amino-3(S)-hydroxy-6-methylheptanoyl}-L-isoleucinol (Compound No. 218)

(a) 3-(2-Thienyl)-DL-alanine methyl ester hydrochloride 3.78 g (0.0318 mole) of thionyl chloride were added dropwise at −5° C. to 10.2 g (0.318 mole) of methanol. After 5 minutes, 3.3 g (0.0159 mole) of 3-(2-thienyl)-DL-alanine hydrochloride were added gradually to this solution, whilst keeping the temperature at −5° C. The mixture was then stirred for 3 hours at this temperature, and then left standing for 24 hours at room temperature. The reaction product was then condensed by evaporation under reduced pressure, and ethanol was added to the residue. The mixture was then condensed by evaporation under reduced pressure and 3.53 g (yield 100%) of 3-(2-thienyl)-DL-alanine methyl ester hydrochloride melting at 110°-112° C. were obtained as the residue.

(b) N-Benzyloxycarbonyl-3-(1-naphthyl)-L-alanyl-3-(2-thienyl)-DL-alanine methyl ester A mixed solution of 1.11 g (5 mmole) of 3-(2-thienyl)-DL-alanine methyl ester hydrochloride and 1.75 g (5 mmole) of N-benzyloxycarbonyl-3-(1-naphthyl)-L-alanine in 15 ml of dimethylformamide was cooled with ice water, and then 1.11 g (11 mmole) of triethylamine was added with stirring. After that, 0.83 g (5 mmole) of diethyl phosphorocyanidate was added, and the mixture was stirred for 3 hours at room temperature. Subsequently, the reaction product was poured into ice water, and the mixture was extracted with ethyl acetate. The extract was washed with water, then dried, and finally purified by thin layer chromatography, yielding 1.9 g (73.6%) of N-benzyloxycarbonyl-3-(1-naphthyl)-L-alanyl-3-(2-thienyl)-DL-alanine methyl ester melting at 140°-141° C.

(c) N-Benzyloxycarbonyl-3-(1-naphthyl)-L-alanyl-3-(2-thienyl)-DL-alanine hydrazide A mixed solution of 1.0 g (194 mmole) of N-benzyloxycarbonyl-3-(1-naphthyl)-L-alanyl-3-(2-thienyl)-DL-alanine methyl ester and 0.64 g (0.2 mmole) of 80% hydrazine hydrate in 10 ml of dimethylformamide was stirred for 2 hours at room temperature and then left standing overnight at room temperature. Dimethylformamide was removed by evaporation under reduced pressure. Water was added to the residue, and the mixture was stirred to form a powdery precipitate, which was collected by filtration, washed with a mixture of diethyl ether and hexane and dried to yield 1.0 g (100%) of N-benzyloxycarbonyl-3-(1-naphthyl)-L-alanyl-3-(2-thienyl)-DL-alanine hydrazide melting at 163°-164° C.

(d) Compound No. 218

517 mg (1 mmole) of N-benzyloxycarbonyl-3-(1-naphthyl)-L-alanyl-3-(2-thienyl)-DL-alanine hydrazide were dissolved in 10 ml of dimethylformamide, and the solution was cooled down to −60° C. 0.85 ml (3.4 mmole) of 4N hydrogen chloride in dioxane was then added. The temperature of this mixture was elevated to −20° C., and then 0.16 ml (1.19 mmole) of isoamyl nitrile was added and the mixture was stirred for 10 minutes. The reaction product was again cooled down to −60° C., and 0.42 ml (3.82 mmole) of N-methylmorpholine was added for neutralization. Subsequently, 370 mg (1.2 mmole) of 4(S)-amino-3(S)-hydroxy-6-methylheptanoyl-L-isoleucinol hydrochloride were added, and the mixture was stirred for 30 minutes. The reaction product was stirred overnight at 0° C., condensed by evaporation under reduced pressure and purified by thin layer chromatography, using as developing solvent a 99:1 by volume mixture of chloroform and methanol, to yield 100 mg (13.2%) of the title compound melting at 160°-162° C., $[\alpha]^{23}-61.7°$ (C=0.3, dimethylformamide).

Elemental analysis: Calculated for $C_{42}H_{54}N_4O_7S$: C, 66.47%; H, 7.17%; N, 7.38%; S, 4.22%. Found: C, 66.22%; H, 6.99%; N, 7.39%; S, 4.42%.

EXAMPLE 19

N-{4(S)-[N-Benzyloxycarbonyl-3-(1-naphthyl)-L-alanyl-3-(4-thiazolyl)-DL-alanyl]amino-3(S)-hydroxy-6-methylheptanoyl}-L-isoleucinol (Compound No. 228)

(a)
N-Benzyloxycarbonyl-3-(1-naphthyl)-L-alanyl-3-(4-thiazolyl)-DL-alanine hydrazide 2.90 g (8.30 mmole) of N-benzyloxycarbonyl-3-(1-naphthyl)-L-alanine and 2.15 g (8.30 mmole) of 3-(4-thiazolyl)-DL-alanine methyl ester dihydrochloride were suspended in 30 ml of anhydrous tetrahydrofuran. Whilst ice cooling, 1.51 ml (9.95 mmole) of diethyl phosphorocyanidate and 3.82 ml (27.4 mmole) of triethylamine were added dropwise under a nitrogen gas stream, and the mixture was stirred overnight at room temperature. The reaction product was condensed by evaporation under reduced pressure. Ethyl acetate was added to the residue, and the mixture was washed with water and then dried over anhydrous magnesium sulfate. The dried product was condensed by evaporation under reduced pressure, and the residue was purified by silica gel column chromatography eluted with a 10:1 by volume mixture of chloroform and methanol, to yield 2.62 g (61%) of N-benzyloxycarbonyl-3-(1-naphthyl)-L-alanyl-3-(4-thiazolyl)-DL-alanine methyl ester.

2.10 g (4.06 mmole) of this ester were dissolved in 20 ml of dimethylformamide, and then 2.00 g (40.0 mmole) of hydrazine hydrate were added; the mixture was stirred overnight at room temperature. This reaction product was condensed by evaporation under reduced pressure, and then water was added to the residue. The precipitating crystals were collected by filtration, washed with hexane and diethyl ether and dried, to yield 1.90 g (90.5%) of the title compound.

(b)
N-{4(S)-[N-Benzyloxycarbonyl-3-(1-naphthyl)-L-alanyl-3-(4-thiazolyl)-DL-alanyl]amino-3(S)-hydroxy-6-methylheptanoyl}-L-isoleucinol 400 mg (0.77 mmole) of N-benzyloxycarbonyl-3-(1-naphthyl)-L-alanyl-3-(4-thiazolyl)-DL-alanine hydrazide were suspended in 10 ml of dimethylformamide, and this suspension was cooled down to $-60°$ C., at which temperature 0.66 ml of 4N hydrogen chloride in dioxane was added. The reaction temperature was raised to $-20°$ C., and then 0.13 ml (0.97 mmole) of isoamyl nitrite was added, and the mixture was stirred for 10 minutes. Disappearance of the hydrazide was confirmed, and then the mixture was again cooled down to $-60°$ C., and 0.33 ml (3.00 mmole) of N-methylmorpholine was added for neutralization, followed by 328 mg (1.02 mmole) of 4(S)-amino-3(S)-hydroxy-6-methylheptanoyl-L-isoleucinol hydrochloride and 0.12 ml (1.09 mmole) of N-methylmorpholine. The solvent was distilled off under reduced pressure and the residue was purified by silica gel preparative thin layer chromatography using a 5:1 by volume mixture of chloroform and methanol as developing solvent, to yield 310 mg (52%) of the monohydrate of the title compound as white crystals melting at 167°–169° C., $[\alpha]^{23} -31.3°$ (C=0.3, methanol).

Elemental analysis: Calculated for $C_{41}H_{53}N_5O_7S \cdot H_2O$: C, 63.29%; H, 7.13%; N, 9.00%; S, 4.12%. Found: C, 63.38%; H, 6.84%; N, 9.14%; S, 4.12%.

EXAMPLE 20

4(S)-{N-Benzyloxycarbonyl-3-(1-naphthyl)-L-alanyl-3-(4-thiazolyl)-DL-alanyl}amino-3(S)-hydroxy-6-methyl-N-[2(RS)-phenylpropyl]heptanamide (Compound No. 243)

400 mg (0.77 mmole) of N-benzyloxycarbonyl-3-(1-naphthyl)-L-alanyl-3-(4-thiazolyl)-DL-alanine hydrazide (synthesized as described in Example 16) were suspended in 10 ml of dimethylformamide, and the suspension was cooled down to $-60°$ C. 0.66 ml of 4N hydrogen chloride in dioxane was added, and the reaction temperature was raised to $-20°$ C. 0.13 ml (0.97 mmole) of isoamyl nitrite was added, and the mixture was stirred for 10 minutes. Disappearance of the hydrazide was confirmed, and then the reaction mixture was again cooled down to $-60°$ C., and then 0.33 ml (3.00 mmole) of N-methylmorpholine was added for neutralization.

Meanwhile, 4(S)-t-butoxycarbonylamino-3(S)-hydroxy-6-methylheptanoic acid and 1-amino-2(RS)-phenylpropane were converted into the corresponding amides with diethyl phosphorocyanidate and triethylamine. Further, the t-butoxycarbonyl group was removed with 6N hydrogen chloride in a dioxane as described in Example 1(b), to synthesize 4(S)-amino-3(S)-hydroxy-6-methyl-N-[2(RS)-phenylpropyl]heptanamide hydrochloride.

335 mg (1.02 mmole) of this compound and 0.12 ml (1.09 mmole) of N-methylmorpholine were added to the above-mentioned reaction mixture, and the mixture was stirred at 4° C. overnight. The solvent was distilled off, and the residue was purified by silica gel preparative thin layer chromatography using a 5:1 by volume mixture of chloroform and methanol as the developing solvent, to yield 325 mg (53%) of the monohydrate of the title compound in the form of white crystals melting at 144°–146° C., $[\alpha]^{23} -35.0°$ (C=0.3, methanol).

Elemental analysis: Calculated for $C_{44}H_{51}N_5O_6S \cdot H_2O$: C, 66.39%; H, 6.71%; N, 8.80%; S, 4.03%. Found: C, 66.86%; H, 6.49%; N, 9.06; S, 4.10%.

EXAMPLE 21

4(S)-[N-Benzyloxycarbonyl-3-(1-naphthyl)-L-alanyl-3-(4-thiazolyl)-DL-alanyl]amino-3(S)-hydroxy-6-methyl-N-[2-(2-pyridyl)ethyl]heptanamide (Compound No. 241)

400 mg (0.77 mmole) of N-benzyloxycarbonyl-3-(1-naphthyl)-L-alanyl-3-(4-thiazolyl)-DL-alanine hydrazide (synthesized as described in Example 16) were suspended in 10 ml of dimethylformamide, and the suspension was cooled down to $-60°$ C. 0.66 ml of 4N hydrogen chloride in dioxane was added to the suspension, and the reaction temperature was raised to $-20°$ C. At this temperature, 0.13 ml (0.97 mmole) of isoamyl nitrite was added, and the mixture was stirred for 10 minutes. Disappearance of the hydrazide was confirmed, and then the mixture was again cooled down to $-60°$ C., at which temperature 0.33 ml (3.00 mmole) of N-methylmorpholine was added for neutralization.

Meanwhile, 4(S)-t-butoxycarbonylamino-3(S)-hydroxy-6-methylheptanoic acid and 2-(2-pyridyl)ethylamine were converted into an amide with diethyl phosphorocyanidate and triethylamine, and the t-butoxycarbonyl group was removed with 6N hydrogen chloride in dioxane as described in Example 1(b), to give 4(S)-amino-3(S)-hydroxy-6-methyl-N-[2-(2-pyridyl)ethyl]heptanamide dihydrochloride.

359 mg (1.02 mmole) of this compound and 0.22 ml (2.00 mmole) of N-methylmorpholine were added to the above-mentioned reaction mixture, and the mixture was stirred overnight at 4° C. The solvent was distilled off under reduced pressure, and the residue was purified by silica gel preparative thin layer chromatography, using a 5:1 by volume mixture of chloroform and methanol as the developing solvent, to yield 301 mg (49%) of the 1.5 hydrate of the title compound in the form of pale brown crystals melting at 134°–136° C., $[\alpha]^{23} -34.7°$ (C=0.3, methanol).

Elemental analysis Calculated for $C_{42}H_{48}N_6O_6S.1.5H_2O$: C, 63.69%; H, 6.49%; N, 10.61%; S, 4.05%. Found: C, 63.50%; H, 6.14%; N, 10.48%; S, 4.16%.

EXAMPLE 22

4(S)-[N-Benzyloxycarbonyl-3-(1-naphthyl)-L-alanyl-3-(4-thiazolyl)-DL-alanyl]amino-3(S)-hydroxy-6-methyl-N-(2-morpholinoethyl)heptanamide (Compound No. 242)

400 mg (0.77 mmole) of N-benzyloxycarbonyl-3-(1-naphthyl)-L-alanyl-3-(4-thiazolyl)-DL-alanine hydrazide (synthesized as described in Example 16) was suspended in 10 ml of dimethylformamide, and the suspension was cooled down to −60° C., at which temperature 0.66 ml of 4N hydrogen chloride in dioxane was added to the suspension. The reaction temperature was then raised to −20° C., at which temperature 0.13 ml (0.97 mmole) of isoamyl nitrite was added to the suspension which was then stirred for 10 minutes. Disappearance of the hydrazide was confirmed, and then the suspension was again cooled down to −60° C., at which temperature 0.33 ml (3.00 mmole) of N-methylmorpholine was added to the suspension for neutralization.

Meanwhile, 4(S)-t-butoxycarbonylamino-3(S)-hydroxy-6-methylheptanoic acid and (2-morpholinoethyl)amine were converted into an amide with diethyl phosphorocyanidate and triethylamine. The t-butoxycarbonyl group was then removed with 6N hydrogen chloride in dioxane, as described in Example 1(b), to give 4(S)-amino-3(S)-hydroxy-6-methyl-N-(2-morpholinoethyl)heptanamide dihydrochloride.

350 mg (0.97 mmole) of this compound and 0.22 ml (2.00 mmole) of N-methylmorpholine were added to the above-mentioned reaction mixture, and the mixture was stirred overnight at 4° C. The solvent was distilled off under reduced pressure, and the residue was purified by silica gel preparative thin layer chromatography, using a 5:1 by volume mixture of chloroform and methanol as the developing solvent, to yield 290 mg (47%) of the 1.5 hydrate of the title compound in the form of white crystals, melting at 132°–136° C., $[\alpha]^{23} -34.3°$ (C=0.3, methanol).

Elemental analysis: Calculated for $C_{41}H_{52}N_6S.1.5H_2O$: C, 61.55%; H, 6.93%; N, 10.50%; S, 4.00%. Found: C, 61.10%; H, 6.30%; N, 10.47%; S, 4.14%.

EXAMPLE 23

N-{(S)-[N-Benzyloxycarbonyl-3-(1-naphthyl)-L-alanyl-3-(2-pyridyl)-DL-alanyl]amino-3(S)-hydroxy-6-methyl-heptanoyl}-L-isoleucinol (Compound No. 259)

(a) N-Benzyloxycarbonyl-3-(1-naphthyl)-L-alanyl-3-(2-pyridyl)-DL-alanine hydrazide 3.00 g (8.59 mmole) of N-benzyloxycarbonyl-3-(1-naphthyl)-L-alanine and 1.40 g (7.77 mmole) of 3-(2-pyridyl)-DL-alanine methyl ester were dissolved in 30 ml of anhydrous tetrahydrofuran, and then 1.3 ml (8.57 mmole) of diethyl phosphorocyanidate and 1.2 ml (8.60 mmole) of triethylamine were added dropwise under a nitrogen gas stream. The mixture was stirred overnight at room temperature.

The mixture was then condensed by evaporation under reduced pressure. Ethyl acetate was added to the residue, and the mixture was washed with water, dried over anhydrous magnesium sulfate and condensed by evaporation under reduced pressure. The residue was purified by silica gel column chromatography eluted with a 10:1 by volume mixture of chloroform and methanol, to yield 3.05 g (76.8%) of N-benzyloxycarbonyl-3-(1-naphthyl)-L-alanyl-3-(2-pyridyl)-DL-alanine methyl ester.

3.00 g (5.86 mmole) of this compound were dissolved in 20 ml of dimethylformamide, and then 2.80 g (55.9 mmole) of hydrazine monohydrate were added to the solution, and the mixture was stirred overnight at room temperature. The reaction product was condensed by evaporation under reduced pressure, and water was added to the residue. The crystals produced were collected by filtration, washed with hexane and diethyl ether and dried to yield 2.93 g (97.7%) of the title compound.

(b) Compound No. 259

512 mg (1.00 mmole) of N-benzyloxycarbonyl-3-(1-naphthyl)-L-alanyl-3-(2-pyridyl)-DL-alanine hydrazide were suspended in 10 ml of dimethylformamide, and the suspension was cooled down to −60° C., at which temperature 0.85 ml of 4N hydrogen chloride in dioxane was added. The reaction temperature of this mixture was then raised to −20° C., at which temperature 0.16 ml (1.19 mmole) of isoamyl nitrite was added, and the mixture was stirred for 10 minutes. Disappearance of the hydrazide was confirmed, and then the suspension was again cooled down to −60° C., at which temperature 0.42 ml (3.82 mmole) of N-methylmorpholine was added for neutralization. 386 mg (1.20 mmole) of 4(S)-amino-3(S)-hydroxy-6-methylheptanoyl-L-isoleucinol hydrochloride and 0.13 ml (1.18 mmole) of N-methylmorpholine were added to the mixture, which was stirred overnight at 4° C.

The solvent was then distilled off under reduced pressure, and the residue was purified by silica gel preparative thin layer chromatography, using a 5:1 by volume mixture of chloroform and methanol as the developing solvent, to yield 300 mg (38%) of the 1.5 hydrate of the title compound in the form of pale brown crystals melting at 153°–155° C., $[\alpha]^{23} -49.7°$ (C=0.3, methanol).

Elemental analysis: Calculated for $C_{43}H_{55}N_5O_7.1.5H_2O$: C, 66.13%; H, 7.49%; N, 8.97%. Found: C, 66.14%, H, 7.22%; N, 8.93%.

EXAMPLE 24

4(S)-[N-Benzyloxycarbonyl-3-(1-naphthyl)-L-alanyl-3-(2-pyridyl)-DL-alanyl]amino-3(S)-hydroxy-6-methyl-N-[2(RS)-phenylpropyl]heptanamide (Compound No. 263)

512 mg (1.00 mmole) of N-benzyloxycarbonyl-3-(1-naphthyl)-L-alanyl-3-(2-pyridyl)-DL-alanine hydrazide (synthesized as described in Example 23) were suspended in 10 ml of dimethylformamide, and the suspension was cooled down to −60° C., at which temperature 0.85 ml of 4N hydrogen chloride in dioxane was added. The reaction temperature was then raised to −20° C., at which temperature 0.16 ml (1.19 mmole) of isoamyl nitrite was added to the mixture and stirred for 10 minutes. Disappearance of the hydrazide was confirmed, and then the mixture was again cooled down to −60° C., and 0.42 ml (3.82 mmole) of N-methylmorpholine was added to the reaction mixture for neutralization.

395 mg (1.20 mmole) of 4(S)-amino-3(S)-hydroxy-6-methyl-N-[2(RS)-phenylpropyl]heptanamide hydrochloride and 0.18 ml (1.64 mmole) of N-methylmorpholine were then added to the reaction mixture, which was then stirred overnight at 4° C. The solvent was distilled off, and the residue was purified by silica gel preparative thin layer chromatography, using a 5:1 by volume mixture of chloroform and methanol, to yield 326 mg (41%) of the 1.5 hydrate of the title compound in the form of pale brown crystals melting at 141°–145° C., $[\alpha]^{23} -36.7°$ (C=0.3, methanol).

Elemental analysis: Calculated for $C_{46}H_{53}N_5O_6 \cdot 1.5\text{-}H_2O$: C, 69.15%; H, 7.06%; N, 8.77%. Found: C, 69.10%; H, 6.65%; N, 9.04%.

EXAMPLE 25

4(S)-[N-Benzyloxycarbonyl-3-(1-naphthyl)-L-alanyl-3-(2-pyridyl)-DL-alanyl]amino-3(S)-hydroxy-6-methyl-N-[2-(2-pyridyl)ethyl]heptanamide (Compound No. 261)

The title compound was obtained by the same processes and treatments as in Example 24, melting at 128°–133° C., $[\alpha]^{23} -34.3°$ (C=0.3, methanol).

Elemental analysis: Calculated for $C_{44}H_{52}N_6O_7$: C, 68.02%; H, 6.75%; N, 10.82%. Found: C, 67.35%; H, 6.77%; N, 10.56%.

What is claimed is:

1. A compound of the formula (I):

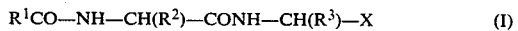

$$R^1CO\text{—}NH\text{—}CH(R^2)\text{—}CONH\text{—}CH(R^3)\text{—}X \quad (I)$$

wherein:

$R^1$ represents a group of formula $R^{13}\text{—}CH(NHR^{12})\text{—}$ in which:

$R^{12}$ represents a 2-(2-methoxyethoxy)ethoxycarbonyl, benzyloxycarbonyl, p-methoxybenzyloxycarbonyl, t-butoxycarbonyl, 9-fluorenylmethoxycarbonyl, 4-phenylbutyryl or 3-(3-nitropyrid-2-yldithio)propionyl, $R^{13}$ represents a benzyl group, a benzyl group having at least one substituent selected from the group consisting of $C_1\text{--}C_4$ alkyl groups and $C_1\text{--}C_4$ alkoxy groups, a 1-naphthylmethyl group, a 3-indolylmethyl group, a 5-quinolymethyl group, a 4-quinolylmethyl group, a 2-pyridylmethyl group, a 3-pyridylmethyl group or a 4-pyridylmethyl group;

$R^2$ represents a $C_1\text{--}C_{10}$ alkyl group, an allyl group, a propargyl group, a cyclopropylmethyl group, a cyclopentylmethyl group, a cyclohexylmethyl group, a benzyl group, a 3-indolylmethyl group, a 2-thienylmethyl group, a 4-thiazolylmethyl group, a 2-thiazolylmethyl group, a 4-methyl-5-thiazolylmethyl group, a 2-, 3- and 4-pyridylmethyl group or a 4-imidazolylmethyl group;

$R^3$ represents an isobutyl, sec-butyl, cyclopropylmethyl, cyclopentylmethyl, or cyclohexylmethyl group;

X represents a group of $\text{—}CH(A\text{—}R^4)OH$, in which:

A represents a single bond or an alkylene group;

$R^4$ represents a protected carboxy group, a carbamoyl group, an N-substituted carbamoyl group, a carbazoyl group, an N-substituted carbazoyl group or an acyl group; provided that, when A represents an alkylene group and when $R^2$ represents a 4-imidazolylmethyl group, $R^4$ does not represent a carbamoyl group or formyl group; and pharmaceutically acceptable salts thereof.

2. A compound as claimed in claim 1, wherein:

$R^2$ represents an imidazolylmethyl group and is attached to a carbon atom having the S-configuration;

$R^3$ represents an isobutyl or sec-butyl group and;

$R^4$ represents a carboxy, N-substituted carbamoyl, carbazoyl, N-substituted carbazoyl or carboxylic acyl group having at least 2 carbon atoms.

3. N-(2-methylbutyl)-4(S)-[N-benzyloxycarbonyl-3-(1-naphthyl)-L-alanyl-L-leucyl]amino-3(S)-hydroxy-6-methylheptanamide of the formula of claim 1.

4. N-{4(S)-[N-benzyloxycarbonyl-3-(1-naphthyl)-L-alanyl-L-leucyl]amino-3(S)-hydroxy-6-methylheptanoyl}-L-isoleucinol of the formula of claim 1.

5. N-{4(S)-[N-benzyloxycarbonyl-3-(1-naphthyl)-L-alanyl-3-(2-thienyl)-DL-alanyl]amino-3(S)-hydroxy-6-methyl-heptanoyl}-L-isoleucinol of the formula of claim 1.

6. N-(2-methylbutyl)-4(S)-[N-benzyloxycarbonyl-3-(1-naphthyl)-L-alanyl-3-(1,3-thiazol-4-yl)-DL-alanyl]amino-3(S)-hydroxy-6-methylheptanamide of the formula of claim 1.

7. N-{4(S)-[N-benzyloxycarbonyl-3-(1-naphthyl)-L-alanyl-3-(1,3-thiazol-4-yl)-DL-alanyl]amino-3(S)-hydroxy-6-methylheptanoyl}-L-isoleucinol of the formula of claim 1.

8. 4(S)-[N-benzyloxycarbonyl-3-(1-naphthyl)-L-alanyl-3-(4-thiazolyl)-DL-alanyl]amino-3(S)-hydroxy-6-methyl-N-(2-morpholinoethyl)heptanamide of the formula of claim 1.

9. N-{4(S)-[N-benzyloxycarbonyl-3-(1-naphthyl)-L-alanyl-3-(2-pyridyl)-L-alanyl]amino-3(S)-hydroxy-6-methylheptanoyl}-L-isoleucinol of the formula of claim 1.

10. N-(2-methylbutyl)-4(S)-{N-[2-(2-methoxyethoxy)ethoxycarbonyl]-3-(1-naphthyl)-L-alanyl-L-histidyl-}amino-3(S)-hydroxy-6-methylheptanamide of the formula of claim 1.

11. N-ethyl-4(S)-[N-benzyloxycarbonyl-3-(1-naphthyl)-L-alanyl-L-histidyl]amino-3(S)-hydroxy-6-methylheptanamide of the formula of claim 1.

12. N-sec-butyl-4(S)-[N-benzyloxycarbonyl-3-(1-naphthyl)-L-alanyl-L-histidyl]amino-3(S)-hydroxy-6-methylheptanamide of the formula of claim 1.

13. N-isobutyl-4(S)-[N-benzyloxycarbonyl-3-(1-naphthyl)-L-alanyl-L-histidyl]amino-3(S)-hydroxy-6-methylheptanamide of the formula of claim 1.

14. 4(S)-[N-benzyloxycarbonyl-3-(1-naphthyl)-L-alanyl-L-histidyl]amino-3(S)-hydroxy-6-methyl-N-(2-methylbutyl)heptanamide of the formula of claim 1.

15. N-{4(S)-[N-benzyloxycarbonyl-3-(1-naphthyl)-L-alanyl-L-histidyl]amino-3(S)-hydroxy-6-methylheptanoyl}-L-isoleucinol of the formula of claim 1.

16. 1-{4(S)-[N-benzyloxycarbonyl-3-(1-naphthyl)-L-alanyl-L-histidyl]amino-3(S)-hydroxy-6-methylheptanoyl}-L-leucinol of the formula of claim 1.

17. 2-[2-{4(S)-[N-benzyloxycarbonyl-3-(1-naphthyl)-L-alanyl-L-histidyl]amino-3(S)-hydroxy-6-methylheptanamido}ethyl]-1-methylpyrrolidine of the formula of claim 1.

18. 3-{4(S)-[N-benzyloxycarbonyl-3-(1-naphthyl)-L-alanyl-L-histidyl]amino-3(S)-hydroxy-6-methylheptanamido}-6-methylheptan-1,3-diol of the formula of claim 1.

19. N-(1-ethyl-2-pyrrolidinylmethyl)-4(S)-[N-benzyloxycarbonyl-3-(1-naphthyl)-L-alanyl-L-histidyl]amino-3(S)-hydroxy-6-methylheptanamide of the formula of claim 1.

20. A method of treating angiotensin-induced hypertension in a mammal by administering to said mammal an effective amount of a renin inhibitor, wherein said renin inhibitor is selected from the group consisting of compounds of formula (I) and pharmaceutically acceptable salts thereof as defined in claim 1.

21. A method as claimed in claim 20, wherein:
$R^2$ represents an imidazolylmethyl group and is attached to a carbon atom having the S-configuration;
$R^3$ represents an isobutyl or sec-butyl group; and
$R^4$ represents a carboxy, N-substituted carbamoyl, carbazoyl, N-substituted carbazoyl or carboxylic acyl group having at least 2 carbon atoms.

22. A method as claimed in claim 20, wherein said renin inhibitor is selected from the group consisting of:
N-(2-methylbutyl)-4(S)-[N-benzyloxycarbonyl-3-(1-naphthyl)-L-alanyl-L-leucyl]amino-3(S)-hydroxy-6-methylheptanamide
N-{4(S)-[N-benzyloxycarbonyl-3-(1-naphthyl)-L-alanyl-L-leucyl]amino-3(S)-hydroxy-6-methylheptanoyl}-L-isoleucinol
N-{4(S)-[N-benzyloxycarbonyl-3-(1-naphthyl)-L-alanyl-3-(2-thienyl)-DL-alanyl]amino-3(S)-hydroxy-6-methylheptanoyl}-L-isoleucinol
N-(2-methylbutyl)-4(S)-[N-benzyloxycarbonyl-3-(1-naphthyl)-L-alanyl-3-(1,3-thiazol-4-yl)-DL-alanyl]amino-3(S)-hydroxy-6-methylheptanamide
N-{4(S)-[N-benzyloxycarbonyl-3-(1-naphthyl)-L-alanyl-3-(1,3-thiazol-4-yl)-DL-alanyl]amino-3(S)-hydroxy-6-methylheptanoyl}-L-isoleucinol
4(S)-[N-benzyloxycarbonyl-3-(1-naphthyl)-L-alanyl-3-(4-thiazolyl)-DL-alanyl]amino-3(S)-hydroxy-6-methyl-N-(2-morpholinoethyl)heptanamide
N-{4(S)-[N-benzyloxycarbonyl-3-(1-naphthyl)-L-alanyl-3-(2-pyridyl)-L-alanyl]amino-3(S)-hydroxy-6-methylheptanoyl}-L-isoleucinol
N-(2-methylbutyl)-4(S)-{N-[2-(2-methoxyethoxy)ethoxycarbonyl]-3-(1-naphthyl)-L-alanyl-L-histidyl}amino-3(S)-hydroxy-6-methylheptanamide
N-ethyl-4(S)-[N-benzyloxycarbonyl-3-(1-naphthyl)-L-alanyl-L-histidyl]amino-3(S)-hydroxy-6-methylheptanamide
N-sec-butyl-4(S)-[N-benzyloxycarbonyl-3-(1-naphthyl)-L-alanyl-L-histidyl]amino-3(S)-hydroxy-6-methylheptanamide
N-isobutyl-4(S)-[N-benzyloxycarbonyl-3-(1-naphthyl)-L-alanyl-L-histidyl]amino-3(S)-hydroxy-6-methylheptanamide
4(S)-[N-benzyloxycarbonyl-3-(1-naphthyl)-L-alanyl-L-histidyl]amino-3(S)-hydroxy-6-methyl-N-(2-methylbutyl)heptanamide
N-{4(S)-[N-benzyloxycarbonyl-3-(1-naphthyl)-L-alanyl-L-histidyl]amino-3(S)-hydroxy-6-methylheptanoyl}-L-isoleucinol
1-{4(S)-[N-benzyloxycarbonyl-3-(1-naphthyl)-L-alanyl-L-histidyl]amino-3(S)-hydroxy-6-methylheptanoyl}-L-leucinol
2-[2-{4(S)-[N-benzyloxycarbonyl-3-(1-naphthyl)-L-alanyl-L-histidyl]amino-3(S)-hydroxy-6-methylheptanamido}ethyl]-1-methylpyrrolidine
3-{4(S)-[N-benzyloxycarbonyl-3-(1-naphthyl)-L-alanyl-L-histidyl]amino-3(S)-hydroxy-6-methylheptanamido}-6-methylheptan-1,3-diol
N-(1-ethyl-2-pyrrolidinylmethyl)-4(S)-[N-benzyloxycarbonyl-3-(1-naphthyl)-L-alanyl-L-histidyl]amino-3(S)-hydroxy-6-methylheptanamide.

23. A method as claimed in claim 20, wherein said mammal is human.

* * * * *